(12) United States Patent
Neerup et al.

(10) Patent No.: US 9,089,538 B2
(45) Date of Patent: Jul. 28, 2015

(54) PEPTIDE CONJUGATES OF GLP-1 RECEPTOR AGONISTS AND GASTRIN AND THEIR USE

(75) Inventors: Trine Skovlund Ryge Neerup, Frederikssund (DK); Torben Østerlund, Lund (SE); Jakob Lind Tolborg, Herlev (DK); Keld Fosgerau, Vanløse (DK); Ulrika Mårtensson, Lund (SE); Marianne Brorson, Søborg (DK); Kamilla Rolsted, Slagelse (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 13/642,349

(22) PCT Filed: Apr. 27, 2011

(86) PCT No.: PCT/DK2011/050133
§ 371 (c)(1),
(2), (4) Date: Feb. 13, 2013

(87) PCT Pub. No.: WO2011/134471
PCT Pub. Date: Nov. 3, 2011

(65) Prior Publication Data
US 2013/0143793 A1 Jun. 6, 2013

Related U.S. Application Data

(60) Provisional application No. 61/395,119, filed on May 7, 2010, provisional application No. 61/470,170, filed on Mar. 31, 2011.

(30) Foreign Application Priority Data

Apr. 27, 2010 (DK) .................................. 2010 00379
Oct. 15, 2010 (DK) .................................. 2010 00941
Mar. 4, 2011 (DK) .................................. 2011 00149

(51) Int. Cl.
*A61K 38/00* (2006.01)
*A61K 38/26* (2006.01)
*A61K 45/06* (2006.01)
*C07K 14/575* (2006.01)
*C07K 14/595* (2006.01)
*C07K 14/605* (2006.01)
*C07K 14/46* (2006.01)

(52) U.S. Cl.
CPC ................ *A61K 38/26* (2013.01); *A61K 45/06* (2013.01); *C07K 14/463* (2013.01); *C07K 14/57563* (2013.01); *C07K 14/595* (2013.01); *C07K 14/605* (2013.01); *A61K 38/00* (2013.01)

(58) Field of Classification Search
CPC ....... A61K 38/00; A61K 38/26; A61K 45/06; B62B 5/0083; C07K 14/463; C07K 14/57563; C07K 14/595; C07K 14/605
See application file for complete search history.

(56) References Cited

U.S. PATENT DOCUMENTS

| | | | |
|---|---|---|---|
| 4,288,627 | A | 9/1981 | Kubicek |
| 5,118,666 | A | 6/1992 | Habener |
| 5,120,712 | A | 6/1992 | Habener |
| 5,424,286 | A | 6/1995 | Eng |
| 5,512,549 | A | 4/1996 | Chen et al. |
| 5,523,449 | A | 6/1996 | Prasad et al. |
| 5,545,618 | A | 8/1996 | Buckley et al. |
| 5,614,492 | A | 3/1997 | Habener |
| 5,631,224 | A | 5/1997 | Efendic et al. |
| 5,670,360 | A | 9/1997 | Thorens |
| 5,795,861 | A | 8/1998 | Kolterman et al. |
| 5,846,747 | A | 12/1998 | Thorens et al. |
| 5,846,937 | A | 12/1998 | Drucker |
| 6,006,753 | A | 12/1999 | Efendic |
| 6,051,689 | A | 4/2000 | Thorens |
| 6,110,703 | A | 8/2000 | Egel-Mitani et al. |
| 6,114,304 | A | 9/2000 | Kolterman et al. |
| 6,136,784 | A | 10/2000 | L'Italien et al. |
| 6,191,102 | B1 | 2/2001 | DiMarchi et al. |
| 6,268,343 | B1 | 7/2001 | Knudsen et al. |
| 6,271,241 | B1 | 8/2001 | DeSimone et al. |
| 6,277,819 | B1 | 8/2001 | Efendic |
| 6,284,725 | B1 | 9/2001 | Coolidge et al. |
| 6,329,336 | B1 | 12/2001 | Bridon et al. |
| 6,344,180 | B1 | 2/2002 | Holst et al. |
| 6,358,924 | B1 | 3/2002 | Hoffmann |
| 6,384,016 | B1 | 5/2002 | Kaarsholm |
| 6,388,053 | B1 | 5/2002 | Galloway et al. |
| 6,410,508 | B1 | 6/2002 | Isales et al. |
| 6,410,511 | B2 | 6/2002 | L'Italien et al. |
| 6,451,974 | B1 | 9/2002 | Hansen |
| 6,458,924 | B2 | 10/2002 | Knudsen et al. |

(Continued)

FOREIGN PATENT DOCUMENTS

| EP | 1076066 A1 | 2/2001 |
|---|---|---|
| EP | 1196444 B1 | 6/2003 |

(Continued)

OTHER PUBLICATIONS

U.S. Appl. No. 14/095,667, Larsen et al.
U.S. Appl. No. 14/116,268, Just et al.
Cleland et al., "The development of stable protein formulations: a close look at protein aggregation, deamidation, and oxidation," Crit Rev Ther Drug Carrier Syst. 10(4):307-77 (1993).
Gunn et al., "Central glucagon-like peptide-I in the control of feeding," Biochem Soc Trans. 24(2):581-4 (1996).
Manning et al., "Stability of protein pharmaceuticals," Pharm Res. 6(11):903-18 (1989).
Meyer et al., Chapter 4: Effects of conformation on the Chemical Stability of Pharmaceutically Relevent Polypeptides. *Rational design of stable protein formulations.* Ed. Carpenter et al, 85-6 (2002).

(Continued)

*Primary Examiner* — Thomas S Heard
(74) *Attorney, Agent, or Firm* — Clark & Elbing LLP; Kristina Bieker-Brady

(57) ABSTRACT

The present invention relates, inter alia, to certain peptide conjugates, and to the use of the conjugates in the treatment of a variety of diseases or disorders, including diabetes (type 1 and/or type 2) and diabetes-related diseases or disorders.

31 Claims, 11 Drawing Sheets

(56) References Cited

U.S. PATENT DOCUMENTS

| | | |
|---|---|---|
| 6,506,724 B1 | 1/2003 | Hiles et al. |
| 6,528,486 B1 | 3/2003 | Larsen et al. |
| 6,703,359 B1 | 3/2004 | Young et al. |
| 6,767,887 B1 | 7/2004 | Hoffmann et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 7,056,734 B1 | 6/2006 | Egan et al. |
| 7,115,569 B2 | 10/2006 | Beeley et al. |
| 7,138,375 B2 | 11/2006 | Beeley et al. |
| 7,153,825 B2 | 12/2006 | Young et al. |
| 7,157,555 B1 | 1/2007 | Beeley et al. |
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |
| 7,348,404 B2 | 3/2008 | Holm et al. |
| 7,399,489 B2 | 7/2008 | Kolterman et al. |
| 7,407,932 B2 | 8/2008 | Young et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,741,269 B2 | 6/2010 | Young et al. |
| 7,858,740 B2 | 12/2010 | Beeley et al. |
| 7,928,065 B2 | 4/2011 | Young et al. |
| 7,935,786 B2 | 5/2011 | Larsen |
| 8,026,210 B2 | 9/2011 | Young et al. |
| 8,057,822 B2 | 11/2011 | Prickett et al. |
| 8,097,698 B2 | 1/2012 | Knudsen et al. |
| 8,263,550 B2 | 9/2012 | Beeley et al. |
| 8,288,338 B2 | 10/2012 | Young et al. |
| 8,445,647 B2 | 5/2013 | Prickett et al. |
| 8,642,727 B2 | 2/2014 | Larsen et al. |
| 2002/0137666 A1 | 9/2002 | Beeley et al. |
| 2004/0106547 A1 | 6/2004 | Larsen et al. |
| 2006/0057137 A1 | 3/2006 | Steiness |
| 2006/0194719 A1 | 8/2006 | Ebbehoj et al. |
| 2006/0293232 A1 | 12/2006 | Levy et al. |
| 2007/0111940 A1 | 5/2007 | Larsen et al. |
| 2009/0088369 A1 | 4/2009 | Steiness |
| 2011/0144008 A1 | 6/2011 | Larsen et al. |
| 2011/0245165 A1 | 10/2011 | Larsen et al. |
| 2011/0312878 A1 | 12/2011 | Larsen |
| 2014/0080757 A1 | 3/2014 | Tolborg et al. |
| 2014/0187483 A1 | 7/2014 | Steiness |

FOREIGN PATENT DOCUMENTS

| | | |
|---|---|---|
| EP | 1329458 A2 | 7/2003 |
| EP | 1421950 A1 | 5/2004 |
| EP | 2028192 A1 | 2/2009 |
| EP | 1525219 B1 | 5/2009 |
| EP | 2112161 A2 | 10/2009 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-97/46584 A1 | 12/1997 |
| WO | WO-98/05351 A1 | 2/1998 |
| WO | WO-98/08531 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |
| WO | WO-98/50351 A1 | 11/1998 |
| WO | WO-99/07404 A1 | 2/1999 |
| WO | WO-99/25727 A2 | 5/1999 |
| WO | WO-99/25728 A1 | 5/1999 |
| WO | WO-99/40788 A1 | 8/1999 |
| WO | WO-99/43707 A1 | 9/1999 |
| WO | WO-99/43708 A1 | 9/1999 |
| WO | WO-99/46283 A1 | 9/1999 |
| WO | WO-99/49788 A1 | 10/1999 |
| WO | WO-99/64060 A1 | 12/1999 |
| WO | WO-00/09666 A2 | 2/2000 |
| WO | WO-00/41546 A2 | 7/2000 |
| WO | WO-00/41548 A2 | 7/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | WO-01/04156 A1 | 1/2001 |
| WO | WO-01/32158 A2 | 5/2001 |
| WO | WO-02/34285 A2 | 5/2002 |
| WO | WO-03/022304 A1 | 3/2003 |
| WO | WO-2004/005342 A1 | 1/2004 |
| WO | WO-2005/072045 A2 | 8/2005 |
| WO | WO-2007/095737 A1 | 8/2007 |
| WO | WO-2007/100535 A2 | 9/2007 |
| WO | WO-2008/071010 A1 | 6/2008 |
| WO | WO-2008/071972 A1 | 6/2008 |
| WO | WO-2008/101017 A2 | 8/2008 |
| WO | WO-2008/152403 A1 | 12/2008 |
| WO | WO-2008/155257 A1 | 12/2008 |
| WO | WO-2009/077737 A2 | 6/2009 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/096052 A1 | 8/2010 |
| WO | WO-2011/084808 A2 | 7/2011 |
| WO | WO-2011/088837 A1 | 7/2011 |
| WO | WO-2011/134471 A1 | 11/2011 |

OTHER PUBLICATIONS

Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem 67(5):1982-91 (1996).

Parkes et al., "Insulinotropic actions of exendin-4 and glucagon-like peptide-1 in vivo and in vitro," Metabolism. 50(5):583-589 (2001).

Pocai et al., "Glucagon-like peptide 1/glucagon receptor dual agonism reverses obesity in mice" Diabetes. 58(10):2258-66 (2009).

Poon et al., "Exenatide improves glycemic control and reduces body weight in subjects with type 2 diabetes: a dose-ranging study," Diabetes Technol Ther. 7(3):467-77 (2005).

Pridal et al., "Absorption of glucagon-like peptide-1 can be protracted by zinc or protamine," Int J Pharm 136:53-59 (1996).

Raufman et al. "Exendin-3, a novel peptide from Heloderma horridum venom, interacts with vasoactive intestinal peptide receptors and a newly described receptor on dispersed acini from guinea pig pancreas," J Biol Chem. 266(5):2897-902 (1991).

Raufman et al, "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).

Suarez-Pinzon et al., "Combination therapy with epidermal growth factor and gastrin increases beta-cell mass and reverses hyperglycemia in diabetic NOD mice," Diabetes. 54(9):2596-601 (2005).

Tang-Christensen et al., "Central administration of GLP-1-(7-36) amide inhibits food and water intake in rats," Am J. Physiol. 271(4 Pt 2):R848-56 (1996).

(56) References Cited

OTHER PUBLICATIONS

Turton et al., "A role for glucagon-like peptide-1 in the central regulation of feeding," Nature 379(6560):69-72 (1996).
Underwood et al., "Crystal structure of glucagon-like peptide-1 in complex with the extracellular domain of the glucagon-like peptide-1 receptor," J Biol Chem. 285(1):723-30 (2010).
Wettergren et al., "Truncated GLP-1 (proglucagon 78-107-amide) inhibits gastric and pancreatic functions in man," Dig Dis Sci. 38(4):665-73 (1993).
U.S. Appl. No. 60/132,018, filed Apr. 30, 1999 (99 pages).
Action Closing Prosecution in Inter Partes Reexam U.S. Appl. No. 95/000,276, mailed Mar. 17, 2011 (25 pages).
Decision in Inter Partes Reexam for U.S. Appl. No. 95/000,276, filed Nov. 25, 2013 (29 pages).
European Medicines Agency, European Public Assessment Report (EPAR) for European Application 03762471.5, updated in Jan. 2006 (11 pages).
European Search Opinion and Extended European Search Report for European Patent Application No. 08016668.9, dated Jan. 27, 2009 (5 pages).
European Search Report for European Patent Application No. 09002937, dated Mar. 15, 2010 (5 pages).
Notice of Opposition for European Patent No. 1525219, dated Feb. 26, 2010 (24 pages).
European Search Report for European Patent Application No. 99610043, dated Jan. 18, 2000 (2 pages).
International Preliminary Examination Report for International Application No. PCT/DK03/00463, dated Sep. 20, 2004 (5 pages).
International Search Report and Written Opinion for International Application No. PCT/IB2012/001090, mailed Jan. 25, 2013 (15 pages).
International Search Report for International Application No. PCT/DK03/00463, dated Oct. 22, 2003 (7 pages).
International Search Report and Written Opinion for International Patent Application No. PCT/EP2012/071766, mailed Feb. 15, 2013 (10 pages).
International Search Report for International Application No. PCT/DK00/00393, mailed Nov. 8, 2000 (3 pages).
International Search Report for International Application No. PCT/DK2011/050018, mailed May 30, 2011 (4 pages).
Partial European Search Report for European Patent Application No. 99610043, dated Jan. 18, 2000 (4 pages).
Partial European Search Report for European Patent Application No. 03005786, dated Oct. 23, 2003 (6 pages).
Extended European Search Report for European Patent Application No. 11774431.8, dated Sep. 30, 2013 (11 pages).
Ally et al., "Rapid determination of creatine, phosphocreatine, purine bases and nucleotides (ATP, ADP, AMP, GTP, GDP) in heart biopsies by gradient ion-pair reversed-phase liquid chromatography," *J. Chromatogr* 575:19-27, 1992.
Bailey et al., "Glucagon-like peptide-1 and the entero-insular axis in obese hyperglycaemic (ob/ob) mice," *Life. Sci.* 40:521-525, 1987.
Ban et al., "Cardioprotective and vasodilatory actions of glucagon-like peptide 1 receptor are mediated through both glucagon-like peptide 1 receptor-dependent and -independent pathways," *Circulation* 117:2340-2350, 2008.
Bedford et al., "Amino acid structure and 'difficult sequences' in solid phase peptide synthesis," *Int. J. Peptide Protein Res.* 40: 300-307, 1992.
Behme et al., "Glucagon-like peptide 1 improved glycemic control in Type 1 diabetes," *BMC Endocrinol. Disord* 3:1-9, 2003.
Burcelin et al., "Long-lasting antidiabetic effect of a dipeptidyl peptidase IV-resistant analog of glucagon-like peptide-1," *Metabolism* 48:252-258, 1999.
Buse, "Progressive use of medical therapies in type 2 diabetes," *Diabetes Spectrum* 13:211-220, 2000.
Buse et al., "The effect of epinephrine, glucagon, and the nutritional state on the oxidation of branched chain amino acids and pyruvate by isolated hearts and diaphragms of the rat," *J Biol Chem.* 248:697-706, 1973.
Byrne et al., "Inhibitory effects of hyperglycaemia on fed jejunal motility: potential role of hyperinsulinaemia," *European Journal of Clinical Investigation* 28:72-78, 1998.
Carpenter et al., "Rational design of stable lyophilized protein formulations: some practical advice," *Pharm Res.* 14:969-975, 1997.
Chen et al., "Evidence that the diabetes gene encodes the leptin receptor: identification of a mutation in the leptin receptor gene in db/db mice," *Cell* 84:491-495, 1996.
Chen et al., "Tissue-specific expression of unique mRNAs that encode proglucagon-derived peptides or exendin 4 in the lizard," *The Journal of Biological Chemistry* 272:4108-4115, 1997.
Cohen et al., "Oxyntomodulin Suppresses Appetite and Reduces Food Intake in Humans," *Journal of Clinical Endocrinology & Metabolism* 88:4696-4701, 2003.
Coleman, "Effects of parabiosis of obese with diabetes and normal mice," *Diabetologia* 9:294-298, 1973.
D'Alessio et al., "Glucagon-like peptide 1 enhances glucose tolerance both by stimulation of insulin release and by increasing insulin-independent glucose disposal," *J. Clin. Invest* 93:2263-2266, 1994.
Dakin et al., "Peripheral oxyntomodulin reduces food intake and body weight gain in rats," *Endocrinology* 145:2687-2695, 2004.
De Boer et al., "The *tac* promoter: a functional hybrid derived from the *trp* and *lac* promoters," *Proc. Natl. Acad. Sci. USA* 80:21-25, 1983.
Deacon et al., "Dipeptidyl peptidase IV inhibition potentiates the insulinotropic effect of glucagon-like-peptide 1 in the anesthetized pig," *Diabetes* 47:764-769, 1998.
Deacon et al., "Dipeptidyl peptidase IV resistant analogues of glucagon-like peptide-1 which have extended metabolic stability and improved biological activity," *Diabetologia* 41:271-278, 1998.
Delgado et al., "The uses and properties of PEG-linked proteins," *Crit. Rev. Ther. Drug. Carrier Syst.* 9:249-304, 1992.
Dickstein et al., "ESC Guidelines for the diagnosis and treatment of acute and chronic heart failure 2008: the Task Force for the Diagnosis and Treatment of Acute and Chronic Heart Failure 2008 of the European Society of Cardiology. Developed in collaboration with the Heart Failure Association of the ESC (HFA) and endorsed by the European Society of Intensive Care Medicine (ESICM)," *Eur. Heart J.* 29:2388-2442, 2008.
Drucker, "Glucagon-Like Peptides," *Diabetes* 47:159-169, 1998.
Edvell et al., "Initiation of increased pancreatic islet growth in young normoglycemic mice (Umeå +/?)," *Endocrinology* 140:778-783, 1999.
Ehrlich, "DNA cloning in *Bacillus subtilis*," *Proc. Natl. Acad. Sci, USA* 75:1433-1436, 1978.
EMEA Humalog Information: European Public Assessment Report (EPAR) and Scientific Discussions, 2006.
Eng et al., "Isolation and characterization of exendin-4, an exedin-3 analogue, from *Heloderma suspectum* venom," *J. Biol. Chem.* 267:7402-7405, 1992.
Farah et al., "Studies on the pharmacology of glucagon," *J Pharmacol Exp Ther.* 129:49-55, 1960.
Fineman et al., "AC2993 (Synthetic Exendin-4) added to existing metformin (Met) and/or Sulfonylurea (SFU) treatment improved glycemic control in patients with type 2 diabetes (DM2) during 28 days of treatment," Diabetes 51 (Supplement 2):A85, Abstract 343-OR, Abstrct Book 62nd Scientific Sessions, Jun. 14-18, 2002.
Francis et al., "PEGylation of cytokines and other therapeutic proteins and peptides: the importance of biological optimisation of coupling techniques," *Int. J. Hematol.* 68:1-18, 1998.
Göke et al., "Distribution of GLP-1 binding sites in the rat brain: Evidence that exendin-4 is a ligand of brain GLP-1 binding sites," *European Journal of Neuroscience* 7:2294-2300, 1995.
Göke et al., "Exendin-4 is a high potency agonist and truncated exendin-(9-39)-amide an antagonist at the glucagon-like peptide 1-(7-36)-amide receptor of insulin-secreting β-cells," *J. Biol. Chem.* 268:19650-19655, 1993.
Gombotz et al. "Biodegradable Polymers for Protein and Peptide Drug Delivery," *Bioconjugate Chem.* 6:332-351, 1995.
Greig et al., "Once daily injection of exendin-4 to diabetic mice achieves long-term beneficial effects on blood glucose concentrations," *Diabetologia* 42:45-50, 1999.

(56) References Cited

OTHER PUBLICATIONS

Grieve et al., "Emerging cardiovascular actions of the incretin hormone glucagon-like peptide-1: Potential therapeutic benefits beyond glycaemic control?," *British Journal of Pharmacology* 157:1340-1351, 2009.
Guo et al., "3'-end-forming signals of yeast mRNA," *Mol Cell Biol.* 15:5983-5990, 1995.
Haffner et al., "Intensive lifestyle intervention or metformin on inflammation and coagulation in participants with impaired glucose tolerance," *Diabetes* 54:1566-1572, 2005.
Hamad et al., "Pharmacologic therapy of chronic heart failure," *American Journal of Cardiovascular Drugs* 7235-248, 2007.
Harikae, "The Effects of a Behavioral program in the obese NIDDM Patients-Observations on daily activity degree of obesity, and blood sugar control," *Bulletin of the School of Nursing, Yamaguchi Prefectural University* 2:1-12, 1998 (Abstract in English).
Heinrich et al., "Pre-proglucagon messenger ribonucleic acid: nucleotide and encoded amino acid sequences of the rat pancreatic complementary deoxyribonucleic acid," *Endocrinology* 115:2176-2181, 1984.
Hoist, "Enteroglucagon," *Annu. Rev. Physiol.* 59:257-271, 1997.
Hoist, "Glucagon-like peptide-1, a gastrointestinal hormone with a pharmaceutical potential," *Curr. Med. Chem.* 6:1005-1017, 1999.
Hoist, "The physiology of glucagon-like peptide 1," *Physiol Rev.* 87: 1409-1439, 2007.
Hudecz et al., "Synthesis, Conformation, Biodistribution, and in Vitro Cytotoxicity of Daunomycin-Branched Polypeptide Conjugates," *Bioconjugate Chem.* 3:49-57, 1992.
Hui et al, "The short half-life of glucagon-like-peptide-1 in plasma does not reflect its long-lasting beneficial effects," *Eur. J. Endocrinol.* 146:863-869, 2002.
Ingwall et al., "Is the failing heart energy starved? On using chemical energy to support cardiac function," *Circ Res.* 95:135-145, 2004.
International Search Report for International Application No. PCT/DK2011/050133 mailed Oct. 6, 2011 (5 pages).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation," *Circulation* 119:1977-2016, 2009.
Juntti-Berggren et al., "The antidiabetogenic effect of GLP-1 is maintained during a 7-day treatment period and improves diabetic dyslipoproteinemia in NIDDM patients," *Diabetes Care* 19:1200-1206, 1996.
Korc, "Islet growth factors: curing diabetes and preventing chronic pancreatitis?," *J. Clin. Invest.* 92:1113-1114, 1993.
Krchnák et al., "Aggregation of resin-bound peptides using solid-phase peptide synthesis," *Int. J. Peptide Protein Res.* 42:450-454, 1993.
Larsen et al., "Sequence-assisted peptide synthesis (SAPS)," *J. Peptide Res.* 52:470-476, 1998.
Leiter et al., "Influence of dietary carbohydrate on the induction of diabetes in C57BL/KsJ-*db/db* diabetes mice," *J. Nutr.* 113:184-195, 1983.
Levey et al., "Activation of adenyl cyclase by glucagon in cat and human heart," *Circ Res.* 24:151-156, 1969.
Lopaschuk et al., "Measurements of fatty acid and carbohydrate metabolism in the isolated working rat heart," *Molecular and Cellular Biochemistry* 172:137-147, 1997.
López-Delgado et al., "Effects of glucagon-like peptide 1 on the kinetics of glycogen synthase *a* in hepatocytes from normal and diabetic rats," *Endocrinology* 139:2811-2817, 1998.
Loyter et al., "Mechanisms of DNA uptake by mammalian cells: fate of exogenously added DNA monitored by the use of fluorescent dyes," *Proc. Natl. Acad. Sci. USA* 79:422-426, 1982.
Matthes et al., "Simultaneous rapid chemical synthesis of over one hundred oligonucleotides on a microscale," *EMBO J* 3:801-805, 1984.

Mayer et al., "Effect of glucagon on clyclic 3',5'-AMP, phosphorylase activity and contractility of heart muscle of the rat," *Circulation Research* 26:225-233, 1970.
Meurer et al., "Properties of native and in vitro glycosylated forms of the glucagon-like peptide-1 receptor antagonist exendin (9-39)," *Metabolism* 48:716-724, 1999.
Mojsov, "Structural requirements for biological activity of glucagon-like peptide-I," *Int. J. Pept Protein Res.* 40:333-343, 1992.
Nauck et al., "Glucagon-like peptide 1 and its potential in the treatment of non-insulin-dependent diabetes mellitus," *Horm. Metab. Res.* 29:411-416, 1997.
Neubauer et al., "Myocardial phosphocreatine-to-ATP ratio is a predictor of mortality in patients with dilated cardiomyopathy," *Circulation* 96:2190-2196, 1997.
Neumann et al., "Gene transfer into mouse lyoma cells by electroporation in high electric fields," *EMBO J.* 1:841-845, 1982.
Nikolaidis et al., "Active metabolite of GLP-1 mediates myocardial glucose uptake and improves left ventricular performance in conscious dogs with dilated cardiomyopathy," *Am J Physiol Heart Circ Physiol.* 289:H2401-H2408, 2005.
Nikolaidis et al., "Recombinant glucagon-like peptide-1 increases myocardial glucose uptake and improves left ventricular performance in conscious dogs with pacing-induced dilated cardiomyopathy," *Circulation* 110:955-961, 2004.
Orskov, "Glucagon-like peptide-1, a new hormone of the entero-insular axis," *Diabetologia* 35:701-711, 1992.
Owens et al., "Insulins today and beyond," *The Lancet* 358:739-746, 2001.
Parkes et al., "Insulinotropic actions of exendin-4 and glucagon-like peptide-1 in vivo and in vitro," *Metabolism* 50:583-589, 2001.
Pederson et al., "Improved glucose tolerance in Zucker Fatty Rats by oral administration of the dipeptidyl peptidase IV inhibitor isoleucine thiazolidide," *Diabetes* 47:1253-1258, 1998.
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002, *Diabetologia* 45 (Suppl. 1):A147, Abstract No. 447, 2002.
Pohl et al., "Molecular cloning of the helodermin and exendin-4 cDNAs in the lizard," *The Journal of Biological Chemistry* 273:9778-9784, 1998.
Pratesi et al., "Poly-L-aspartic acid as a carrier for doxorubicin: a comparative in vivo study of free and polymer-bound drug," *Br. J. Cancer* 52:841-848, 1985.
Raufman, "Bioactive peptides from lizard venoms," *Reg. Peptides* 61:1-18, 1996.
Ritzel et al., "A synthetic glucagon-like peptide-1 analog with improved plasma stability," *Journal of Endocrinology* 159:93-102, 1998.
Roach et al., "Improved postprandial glycemic control during treatment with humalog Mix25, a novel protamine-based insulin lispro formulation," *Diabetes Care* 22: 1258-1261, 1999.
Robberecht et al., "Comparative efficacy of seven synthetic glucagon analogs, modified in position 1, 2, and/or 12, on liver and heart adenylate cyclase from rat," *Peptides* 7:109-112, 1986.
Rolin et al., "The long-acting GLP-1 derivative NN2211 ameliorates glycemia and increases β-cell mass in diabetic mice," *Am. J. Physiol. Endocrinol. Metab.* 283:E745-E752, 2002.
Rooman et al., "Gastrin stimulates β-cell neogenesis and increases islet mass from transdifferentiated but not from normal exocrine pancreas tissue," *Diabetes.* 51:686-690, 2002.
Saraceni et al., "Effects of glucagon-like peptide-1 and long acting analogues on cardiovascular and metabolic function," *Drugs R.D.*, 8: 145-153, 2007.
Sowden et al., "Oxyntomodulin increases intrinsic heart rate in mice independent of the glucagon-like peptide-1 receptor," *American Journal of Physiology-Regulatory Integrative and Comparative Physiology* 292: R962-R970, 2007.
Stoffers et al., "Insulinotropic glucagon-like peptide 1 agonists stimulate expression of homeodomain protein IDX-1 and increases islet size in mouse pancreas," *Diabetes* 49:741-748, 2000.

(56) References Cited

OTHER PUBLICATIONS

Suarez-Pinzon et al., "Combination therapy with glucagon-like peptide-1 and gastrin restores normoglycemia in diabetic NOD mice," *Diabetes* 57:3281-3288, 2008.

Thorkildsen et al., "ZP10—A New GLP-1 agonist that increases insulin mRNA expression," Nedergaard Symposium, Odense, Denmark, Jan. 24, 2002 (abstract only).

Thorkildsen et al., "ZP10—A New GLP-1 agonist that increases insulin mRNA expression," Nedergaard Symposium, Odense, Denmark, Jan. 24, 2002 (Poster presentation).

Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002, Poster presentation.

Tomita et al., "Pancreatic islets of obese hyperglycemic mice (ob/ob)," *Pancreas.* 7:367-375, 1992.

Tourrel et al., "Persistent improvement of type 2 diabetes in the Goto-Kakizaki Rat model by expansion of the β-cell mass during the prediabetic period with glucagon-like peptide-1 or exendin-4," *Diabetes* 51:1443-1452, 2002.

Tsukada et al., "An anti-α-fetoprotein antibody-daunorubicin conjugate with a novel poly-L-glutamic acid derivative as intermediate drug carrier," *J. Natl. Cancer Inst.* 73:721-729, 1984.

Uesaka et al., "Glucagon-like peptide isolated from the eel intestine: Effects on atrial beating," *Journal of Experimental Biology* 204:3019-3026, 2001.

Uttenthal et al., "Molecular forms of glucagon-like peptide-1 in human pancreas and glucagonomas," *J. Clin. Endocrinol. Metabol.* 61:472-479, 1985.

Villa-Kamaroff et al., "A bacterial clone synthesizing proinsulin," *Proc. Natl. Acad. Sci. USA* 75:3727-3731, 1978.

Wang et al., "Glucagon-like peptide-1 treatment delays the onset of diabetes in 8 week-old db/db mice," *Diabetologia* 45:1263-1273, 2002.

White, "A review of potential cardiovascular uses of intravenous glucagon administration," *J Clin Pharmacol.* 39:442-447, 1999.

Wiberg et al., "Replication and expression in mammalian cells of transfected DNA; description of an improved erythrocyte ghost fusion technique," *Nucleic Acids Res.* 11:7287-7302, 1983.

Xu et al., "Exendin-4 stimulates both β-cell replication and neogenesis, resulting in increased β-cell mass and improved glucose tolerance in diabetic rats," *Diabetes* 48:2270-2276, 1999.

Yabe et al., "Quantitative measurements of cardiac phosphorus metabolites in coronary artery disease by $^{31}$P magnetic resonance spectroscopy," *Circulation* 92:15-23, 1995.

Young et al., "Glucose-lowering and insulin-sensitizing actions of exendin-4: Studies in obese diabetic (ob/ob, db/db) mice, diabetic fatty zucker rats, and diabetic rhesus mondays (*Macaca mulatta*)," *Diabetes* 48:1026-1034, 1999.

Young et al., "Physiological and genetic factors affecting transformation of *Bacillus subtilis*," *J Bacteriol.* 81:823-829, 1961.

Zalipsky, "Functionalized poly(ethylene glycol) for preparation of biologically relevant conjugates," *Bioconjugate Chem.* 6:150-165, 1995.

Zander et al., "Additive glucose-lowering effects of glucagon-like peptide-1 and metformin in type 2 diabetes," *Diabetes Care* 24:720-725, 2001.

Zhao et al., "Direct effects of glucagon-like peptide-1 on myocardial contractility and glucose uptake in normal and postischemic isolated rat hearts," *J Pharmacol Exp Ther.* 317:1106-1113, 2006.

Zhou et al., "Glucagon-like peptide-1 and exendin-4 convert pancreatic AR42J cells into glucagon- and insulin-producing cells," *Diabetes* 48: 2358-2366, 1999.

Statistics: *p<0.05 by 1-way ANOVA with
Dunnett's multiple comparison test vs. vehicle

SEQUENCE LISTING

<160> NUMBER OF SEQ ID NOS: 116

<210> SEQ ID NO 1
<211> LENGTH: 58
<212> TYPE: PRT
<213> ORGANISM: Artificial
<220> FEATURE:

```
<223> OTHER INFORMATION: Synthetic peptide sequence
<220> FEATURE:
<221> NAME/KEY: MISC_FEATURE
<222> LOCATION: (40)..(41)
<223> OTHER INFORMATION: Xaa = Peg3

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Xaa Gln Gly Pro Trp Leu Glu Glu
        35                  40                  45

Glu Glu Glu Ala Tyr Gly Trp Leu Asp Phe
    50                  55

<210> SEQ ID NO 2
<211> LENGTH: 56
<212> TYPE: PRT
<213> ORGANISM: Artificial
<220> FEATURE:
<223> OTHER INFORMATION: Synthetic peptide sequence

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gln Gly Pro Trp Leu Glu Glu Glu Glu
        35                  40                  45

Glu Ala Tyr Gly Trp Leu Asp Phe
    50                  55

<210> SEQ ID NO 3
<211> LENGTH: 57
<212> TYPE: PRT
<213> ORGANISM: Artificial
<220> FEATURE:
<223> OTHER INFORMATION: Synthetic peptide sequence

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys Gln Gly Pro Trp Leu Glu Glu Glu
        35                  40                  45

Glu Glu Ala Tyr Gly Trp Leu Asp Phe
    50                  55

<210> SEQ ID NO 4
<211> LENGTH: 59
<212> TYPE: PRT
<213> ORGANISM: Artificial
<220> FEATURE:
<223> OTHER INFORMATION: Synthetic peptide sequence

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

```
Ser Gly Ala Pro Pro Ser Ala Ala Ala Gln Gly Pro Trp Leu Glu
        35                  40                  45

Glu Glu Glu Glu Ala Tyr Gly Trp Leu Asp Phe
    50                  55

<210> SEQ ID NO 5
<211> LENGTH: 59
<212> TYPE: PRT
<213> ORGANISM: Artificial
<220> FEATURE:
<223> OTHER INFORMATION: Synthetic peptide sequence

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Ser Lys Lys Gln Gly Pro Trp Leu Glu
        35                  40                  45

Glu Glu Glu Glu Ala Tyr Gly Trp Leu Asp Phe
    50                  55

<210> SEQ ID NO 6
<211> LENGTH: 60
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(40)
<223> OTHER INFORMATION: Xaa = Peg3

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Ser Lys Lys Gln Gly Pro Trp Leu
        35                  40                  45

Glu Glu Glu Glu Glu Ala Tyr Gly Trp Leu Asp Phe
    50                  55                  60

<210> SEQ ID NO 7
<211> LENGTH: 60
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(40)
<223> OTHER INFORMATION: Xaa = 8AOC

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Ser Lys Lys Gln Gly Pro Trp Leu
        35                  40                  45

Glu Glu Glu Glu Glu Ala Tyr Gly Trp Leu Asp Phe
```

<210> SEQ ID NO 8
<211> LENGTH: 60
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(40)
<223> OTHER INFORMATION: Xaa = DBF = 4-(2-aminoethyl)-6-dibenzofuran-
      propanoyl

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Ser Lys Lys Gln Gly Pro Trp Leu
        35                  40                  45

Glu Glu Glu Glu Glu Ala Tyr Gly Trp Leu Asp Phe
    50                  55                  60

<210> SEQ ID NO 9
<211> LENGTH: 58
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(41)
<223> OTHER INFORMATION: Xaa = 8AOC

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Xaa Gln Gly Pro Trp Leu Glu Glu
        35                  40                  45

Glu Glu Glu Ala Tyr Gly Trp Leu Asp Phe
    50                  55

<210> SEQ ID NO 10
<211> LENGTH: 45
<212> TYPE: PRT
<213> ORGANISM: Artificial
<220> FEATURE:
<223> OTHER INFORMATION: Synthetic peptide sequence

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Tyr Gly Trp Leu Asp Phe
        35                  40                  45

<210> SEQ ID NO 11
<211> LENGTH: 46
<212> TYPE: PRT
<213> ORGANISM: Artificial

```
<220> FEATURE:
<223> OTHER INFORMATION: Synthetic peptide sequence

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys Tyr Gly Trp Leu Asp Phe
        35                  40                  45

<210> SEQ ID NO 12
<211> LENGTH: 48
<212> TYPE: PRT
<213> ORGANISM: Artificial
<220> FEATURE:
<223> OTHER INFORMATION: Synthetic peptide sequence

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Ala Ala Ala Tyr Gly Trp Leu Asp Phe
        35                  40                  45

<210> SEQ ID NO 13
<211> LENGTH: 48
<212> TYPE: PRT
<213> ORGANISM: Artificial
<220> FEATURE:
<223> OTHER INFORMATION: Synthetic peptide sequence

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Ser Lys Lys Tyr Gly Trp Leu Asp Phe
        35                  40                  45

<210> SEQ ID NO 14
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(40)
<223> OTHER INFORMATION: Xaa = Peg3

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Ser Lys Lys Tyr Gly Trp Leu Asp
        35                  40                  45

Phe

<210> SEQ ID NO 15
```

```
<211> LENGTH: 47
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(41)
<223> OTHER INFORMATION: Xaa = Peg3

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Xaa Tyr Gly Trp Leu Asp Phe
        35                  40                  45

<210> SEQ ID NO 16
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(40)
<223> OTHER INFORMATION: Xaa = 8AOC

<400> SEQUENCE: 16

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Ser Lys Lys Tyr Gly Trp Leu Asp
        35                  40                  45

Phe

<210> SEQ ID NO 17
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (40)..(40)
<223> OTHER INFORMATION: Xaa = DBF = 4-(2-aminoethyl)-6-dibenzofuran-
      propanoyl

<400> SEQUENCE: 17

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Ser Lys Lys Tyr Gly Trp Leu Asp
        35                  40                  45

Phe

<210> SEQ ID NO 18
<211> LENGTH: 47
<212> TYPE: PRT
<213> ORGANISM: Artificial
<220> FEATURE:
<223> OTHER INFORMATION: Synthetic peptide sequence
```

```
<220> FEATURE:
<221> NAME/KEY: MISC_FEATURE
<222> LOCATION: (40)..(41)
<223> OTHER INFORMATION: Xaa = 8AOC

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Xaa Tyr Gly Trp Leu Asp Phe
        35                  40                  45

<210> SEQ ID NO 19
<211> LENGTH: 45
<212> TYPE: PRT
<213> ORGANISM: Artificial
<220> FEATURE:
<223> OTHER INFORMATION: Synthetic peptide sequence

<400> SEQUENCE: 19

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gln Gly Pro Trp
            20                  25                  30

Leu Glu Glu Glu Glu Ala Tyr Gly Trp Leu Asp Phe
        35                  40                  45

<210> SEQ ID NO 20
<211> LENGTH: 46
<212> TYPE: PRT
<213> ORGANISM: Artificial
<220> FEATURE:
<223> OTHER INFORMATION: Synthetic peptide sequence

<400> SEQUENCE: 20

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Lys Gln Gly Pro
            20                  25                  30

Trp Leu Glu Glu Glu Glu Glu Ala Tyr Gly Trp Leu Asp Phe
        35                  40                  45

<210> SEQ ID NO 21
<211> LENGTH: 48
<212> TYPE: PRT
<213> ORGANISM: Artificial
<220> FEATURE:
<223> OTHER INFORMATION: Synthetic peptide sequence

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Ala Ala Gln
            20                  25                  30

Gly Pro Trp Leu Glu Glu Glu Glu Glu Ala Tyr Gly Trp Leu Asp Phe
        35                  40                  45

<210> SEQ ID NO 22
<211> LENGTH: 48
<212> TYPE: PRT
<213> ORGANISM: Artificial
<220> FEATURE:
```

-continued

<223> OTHER INFORMATION: Synthetic peptide sequence

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ser Lys Lys Gln
            20                  25                  30

Gly Pro Trp Leu Glu Glu Glu Glu Ala Tyr Gly Trp Leu Asp Phe
        35                  40                  45

<210> SEQ ID NO 23
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa = Peg3

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Ser Lys Lys
            20                  25                  30

Gln Gly Pro Trp Leu Glu Glu Glu Glu Ala Tyr Gly Trp Leu Asp
        35                  40                  45

Phe

<210> SEQ ID NO 24
<211> LENGTH: 47
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Gln Gly
            20                  25                  30

Pro Trp Leu Glu Glu Glu Glu Ala Tyr Gly Trp Leu Asp Phe
        35                  40                  45

<210> SEQ ID NO 25
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa = 8AOC

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Ser Lys Lys

```
                20                  25                  30
Gln Gly Pro Trp Leu Glu Glu Glu Glu Ala Tyr Gly Trp Leu Asp
         35                  40                  45

Phe

<210> SEQ ID NO 26
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa = DBF = 4-(2-aminoethyl)-6-dibenzofuran-
      propanoyl

<400> SEQUENCE: 26

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Ser Lys Lys
                20                  25                  30

Gln Gly Pro Trp Leu Glu Glu Glu Glu Ala Tyr Gly Trp Leu Asp
         35                  40                  45

Phe

<210> SEQ ID NO 27
<211> LENGTH: 47
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = 8AOC

<400> SEQUENCE: 27

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Xaa Gln Gly
                20                  25                  30

Pro Trp Leu Glu Glu Glu Glu Ala Tyr Gly Trp Leu Asp Phe
         35                  40                  45

<210> SEQ ID NO 28
<211> LENGTH: 34
<212> TYPE: PRT
<213> ORGANISM: Artificial
<220> FEATURE:
<223> OTHER INFORMATION: Synthetic peptide sequence

<400> SEQUENCE: 28

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Tyr Gly Trp Leu
                20                  25                  30

Asp Phe

<210> SEQ ID NO 29
<211> LENGTH: 35
<212> TYPE: PRT
<213> ORGANISM: Artificial
```

<220> FEATURE:
<223> OTHER INFORMATION: Synthetic peptide sequence

<400> SEQUENCE: 29

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Lys Tyr Gly Trp
            20                  25                  30
Leu Asp Phe
        35

<210> SEQ ID NO 30
<211> LENGTH: 37
<212> TYPE: PRT
<213> ORGANISM: Artificial
<220> FEATURE:
<223> OTHER INFORMATION: Synthetic peptide sequence

<400> SEQUENCE: 30

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Ala Ala Ala Tyr
            20                  25                  30
Gly Trp Leu Asp Phe
        35

<210> SEQ ID NO 31
<211> LENGTH: 37
<212> TYPE: PRT
<213> ORGANISM: Artificial
<220> FEATURE:
<223> OTHER INFORMATION: Synthetic peptide sequence

<400> SEQUENCE: 31

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Ser Lys Lys Tyr
            20                  25                  30
Gly Trp Leu Asp Phe
        35

<210> SEQ ID NO 32
<211> LENGTH: 38
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa= Peg3

<400> SEQUENCE: 32

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Xaa Ser Lys Lys
            20                  25                  30
Tyr Gly Trp Leu Asp Phe
        35

<210> SEQ ID NO 33
<211> LENGTH: 36
<212> TYPE: PRT

```
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 33

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Tyr Gly
            20                  25                  30

Trp Leu Asp Phe
        35

<210> SEQ ID NO 34
<211> LENGTH: 38
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa = 8AOC

<400> SEQUENCE: 34

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Ser Lys Lys
            20                  25                  30

Tyr Gly Trp Leu Asp Phe
        35

<210> SEQ ID NO 35
<211> LENGTH: 38
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa = DBF = 4-(2-aminoethyl)-6-dibenzofuran-
      propanoyl

<400> SEQUENCE: 35

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Ser Lys Lys
            20                  25                  30

Tyr Gly Trp Leu Asp Phe
        35

<210> SEQ ID NO 36
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = 8AOC

<400> SEQUENCE: 36
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Tyr Gly
            20                  25                  30

Trp Leu Asp Phe
        35

<210> SEQ ID NO 37
<211> LENGTH: 47
<212> TYPE: PRT
<213> ORGANISM: Artificial
<220> FEATURE:
<223> OTHER INFORMATION: Synthetic peptide sequence

<400> SEQUENCE: 37

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gln Gly
            20                  25                  30

Pro Trp Leu Glu Glu Glu Glu Glu Ala Tyr Gly Trp Leu Asp Phe
        35                  40                  45

<210> SEQ ID NO 38
<211> LENGTH: 48
<212> TYPE: PRT
<213> ORGANISM: Artificial
<220> FEATURE:
<223> OTHER INFORMATION: Synthetic peptide sequence

<400> SEQUENCE: 38

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys Gln
            20                  25                  30

Gly Pro Trp Leu Glu Glu Glu Glu Glu Ala Tyr Gly Trp Leu Asp Phe
        35                  40                  45

<210> SEQ ID NO 39
<211> LENGTH: 50
<212> TYPE: PRT
<213> ORGANISM: Artificial
<220> FEATURE:
<223> OTHER INFORMATION: Synthetic peptide sequence

<400> SEQUENCE: 39

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ala Ala
            20                  25                  30

Ala Gln Gly Pro Trp Leu Glu Glu Glu Glu Ala Tyr Gly Trp Leu
        35                  40                  45

Asp Phe
    50

<210> SEQ ID NO 40
<211> LENGTH: 50
<212> TYPE: PRT
<213> ORGANISM: Artificial
<220> FEATURE:
<223> OTHER INFORMATION: Synthetic peptide sequence

<400> SEQUENCE: 40

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ser Lys
                20                  25                  30

Lys Gln Gly Pro Trp Leu Glu Glu Glu Glu Ala Tyr Gly Trp Leu
            35                  40                  45

Asp Phe
    50

<210> SEQ ID NO 41
<211> LENGTH: 51
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(31)
<223> OTHER INFORMATION: Xaa = Peg3

<400> SEQUENCE: 41

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Ser
                20                  25                  30

Lys Lys Gln Gly Pro Trp Leu Glu Glu Glu Glu Ala Tyr Gly Trp
            35                  40                  45

Leu Asp Phe
    50

<210> SEQ ID NO 42
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(32)
<223> OTHER INFORMATION: Xaa = Peg3

<400> SEQUENCE: 42

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Xaa
                20                  25                  30

Gln Gly Pro Trp Leu Glu Glu Glu Glu Ala Tyr Gly Trp Leu Asp
            35                  40                  45

Phe

<210> SEQ ID NO 43
<211> LENGTH: 51
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(31)
<223> OTHER INFORMATION: Xaa = 8AOC

<400> SEQUENCE: 43

His Ala Glu Gly Thr Phe Thr Ser Asp Val Ser Ser Tyr Leu Glu Gly
```

```
1               5                   10                  15
Gln Ala Ala Lys Glu Phe Ile Ala Trp Leu Val Lys Gly Arg Xaa Ser
                20                  25                  30

Lys Lys Gln Gly Pro Trp Leu Glu Glu Glu Glu Ala Tyr Gly Trp
        35                  40                  45

Leu Asp Phe
    50

<210> SEQ ID NO 44
<211> LENGTH: 51
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(31)
<223> OTHER INFORMATION: Xaa = DBF = 4-(2-aminoethyl)-6-dibenzofuran-
      propanoyl

<400> SEQUENCE: 44

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Ser
                20                  25                  30

Lys Lys Gln Gly Pro Trp Leu Glu Glu Glu Glu Ala Tyr Gly Trp
        35                  40                  45

Leu Asp Phe
    50

<210> SEQ ID NO 45
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(32)
<223> OTHER INFORMATION: Xaa = 8AOC

<400> SEQUENCE: 45

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Xaa
                20                  25                  30

Gln Gly Pro Trp Leu Glu Glu Glu Glu Ala Tyr Gly Trp Leu Asp
        35                  40                  45

Phe

<210> SEQ ID NO 46
<211> LENGTH: 36
<212> TYPE: PRT
<213> ORGANISM: Artificial
<220> FEATURE:
<223> OTHER INFORMATION: Synthetic peptide sequence

<400> SEQUENCE: 46

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Tyr Gly
                20                  25                  30
```

```
Trp Leu Asp Phe
        35

<210> SEQ ID NO 47
<211> LENGTH: 37
<212> TYPE: PRT
<213> ORGANISM: Artificial
<220> FEATURE:
<223> OTHER INFORMATION: Synthetic peptide sequence

<400> SEQUENCE: 47

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys Tyr
            20                  25                  30

Gly Trp Leu Asp Phe
        35

<210> SEQ ID NO 48
<211> LENGTH: 39
<212> TYPE: PRT
<213> ORGANISM: Artificial
<220> FEATURE:
<223> OTHER INFORMATION: Synthetic peptide sequence

<400> SEQUENCE: 48

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ala Ala
            20                  25                  30

Ala Tyr Gly Trp Leu Asp Phe
        35

<210> SEQ ID NO 49
<211> LENGTH: 39
<212> TYPE: PRT
<213> ORGANISM: Artificial
<220> FEATURE:
<223> OTHER INFORMATION: Synthetic peptide sequence

<400> SEQUENCE: 49

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ser Lys
            20                  25                  30

Lys Tyr Gly Trp Leu Asp Phe
        35

<210> SEQ ID NO 50
<211> LENGTH: 40
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(31)
<223> OTHER INFORMATION: Xaa = Peg3

<400> SEQUENCE: 50

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Ser
            20                  25                  30
```

Lys Lys Tyr Gly Trp Leu Asp Phe
            35                  40

<210> SEQ ID NO 51
<211> LENGTH: 38
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(32)
<223> OTHER INFORMATION: Xaa = Peg3

<400> SEQUENCE: 51

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Xaa
            20                  25                  30

Tyr Gly Trp Leu Asp Phe
            35

<210> SEQ ID NO 52
<211> LENGTH: 40
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(31)
<223> OTHER INFORMATION: Xaa = 8AOC

<400> SEQUENCE: 52

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Ser
            20                  25                  30

Lys Lys Tyr Gly Trp Leu Asp Phe
            35                  40

<210> SEQ ID NO 53
<211> LENGTH: 40
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(31)
<223> OTHER INFORMATION: Xaa = DBF = 4-(2-aminoethyl)-6-dibenzofuran-
      propanoyl

<400> SEQUENCE: 53

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Ser
            20                  25                  30

Lys Lys Tyr Gly Trp Leu Asp Phe
            35                  40

<210> SEQ ID NO 54
<211> LENGTH: 38
<212> TYPE: PRT
<213> ORGANISM: Artificial

-continued

<220> FEATURE:
<223> OTHER INFORMATION: Synthetic peptide sequence
<220> FEATURE:
<221> NAME/KEY: MISC_FEATURE
<222> LOCATION: (31)..(32)
<223> OTHER INFORMATION: Xaa = 8AOC

<400> SEQUENCE: 54

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa Xaa
            20                  25                  30

Tyr Gly Trp Leu Asp Phe
        35

<210> SEQ ID NO 55
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 55

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Gly Trp
            20                  25                  30

Leu Asp Phe
        35

<210> SEQ ID NO 56
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 56

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Ala Gly
            20                  25                  30

Trp Leu Asp Phe
        35

<210> SEQ ID NO 57
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 57

His Gly Glu Gly Thr Phe Thr Ser Asp Leu Ser Lys Gln Met Glu Glu

```
1               5                   10                  15
Glu Ala Val Arg Leu Phe Ile Glu Trp Leu Lys Asn Xaa Xaa Tyr Ala
            20                  25                  30

Trp Leu Asp Phe
        35

<210> SEQ ID NO 58
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 58

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Xaa Tyr Gly Trp
            20                  25                  30

Leu Asp Phe
        35

<210> SEQ ID NO 59
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 59

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Trp Leu
            20                  25                  30

Asp Phe

<210> SEQ ID NO 60
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 60

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Xaa Xaa Tyr Gly
            20                  25                  30

Trp Leu Asp Phe
        35

<210> SEQ ID NO 61
<211> LENGTH: 36
```

```
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (12)..(12)
<223> OTHER INFORMATION: Xaa = Orn
<220> FEATURE:
<221> NAME/KEY: MISC_FEATURE
<222> LOCATION: (29)..(30)
<223> OTHER INFORMATION: Xaa = Peg3

<400> SEQUENCE: 61

His Gly Glu Gly Thr Phe Thr Ser Asp Leu Ser Xaa Gln Met Glu Glu
1               5                   10                  15

Glu Ala Val Arg Leu Phe Ile Glu Trp Leu Lys Asn Xaa Xaa Tyr Gly
            20                  25                  30

Trp Leu Asp Phe
        35

<210> SEQ ID NO 62
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (27)..(27)
<223> OTHER INFORMATION: Xaa = Orn
<220> FEATURE:
<221> NAME/KEY: MISC_FEATURE
<222> LOCATION: (29)..(30)
<223> OTHER INFORMATION: Xaa = Peg3

<400> SEQUENCE: 62

His Gly Glu Gly Thr Phe Thr Ser Asp Leu Ser Lys Gln Met Glu Glu
1               5                   10                  15

Glu Ala Val Arg Leu Phe Ile Glu Trp Leu Xaa Asn Xaa Xaa Tyr Gly
            20                  25                  30

Trp Leu Asp Phe
        35

<210> SEQ ID NO 63
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 63

His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Xaa Xaa Tyr Gly
            20                  25                  30

Trp Leu Asp Phe
        35

<210> SEQ ID NO 64
<211> LENGTH: 36
<212> TYPE: PRT
<213> ORGANISM: Artificial
```

```
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 64

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asp Xaa Xaa Tyr Gly
             20                  25                  30

Trp Leu Asp Phe
         35

<210> SEQ ID NO 65
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 65

His Gly Glu Gly Thr Phe Thr Ser Asp Leu Ser Lys Tyr Met Glu Glu
 1               5                  10                  15

Glu Ala Val Arg Leu Phe Ile Glu Trp Leu Lys Asn Xaa Xaa Tyr Gly
             20                  25                  30

Trp Leu Asp Phe
         35

<210> SEQ ID NO 66
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (20)..(20)
<223> OTHER INFORMATION: Xaa = Orn
<220> FEATURE:
<221> NAME/KEY: MISC_FEATURE
<222> LOCATION: (29)..(30)
<223> OTHER INFORMATION: Xaa = Peg3

<400> SEQUENCE: 66

His Gly Glu Gly Thr Phe Thr Ser Asp Leu Ser Lys Gln Met Glu Glu
 1               5                  10                  15

Glu Ala Val Xaa Leu Phe Ile Glu Trp Leu Lys Asn Xaa Xaa Tyr Gly
             20                  25                  30

Trp Leu Asp Phe
         35

<210> SEQ ID NO 67
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa = Peg3
```

<400> SEQUENCE: 67

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Tyr Gly Trp
            20                  25                  30

Leu Asp Phe
        35

<210> SEQ ID NO 68
<211> LENGTH: 34
<212> TYPE: PRT
<213> ORGANISM: Artificial
<220> FEATURE:
<223> OTHER INFORMATION: Synthetic peptide sequence

<400> SEQUENCE: 68

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Tyr Gly Trp Leu
            20                  25                  30

Asp Phe

<210> SEQ ID NO 69
<211> LENGTH: 38
<212> TYPE: PRT
<213> ORGANISM: Artificial
<220> FEATURE:
<223> OTHER INFORMATION: Synthetic peptide sequence

<400> SEQUENCE: 69

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Glu Glu Glu Glu Ala
            20                  25                  30

Tyr Gly Trp Leu Asp Phe
        35

<210> SEQ ID NO 70
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 70

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Tyr Gly Trp Leu
            20                  25                  30

Asp Phe

<210> SEQ ID NO 71
<211> LENGTH: 33
<212> TYPE: PRT
<213> ORGANISM: Artificial
<220> FEATURE:
<223> OTHER INFORMATION: Synthetic peptide sequence
<220> FEATURE:

<221> NAME/KEY: MISC_FEATURE
<222> LOCATION: (28)..(28)
<223> OTHER INFORMATION: Xaa = Peg3

<400> SEQUENCE: 71

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Trp Leu Asp
            20                  25                  30

Phe

<210> SEQ ID NO 72
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (27)..(27)
<223> OTHER INFORMATION: Xaa = Peg3

<400> SEQUENCE: 72

His Gly Glu Gly Thr Phe Thr Ser Asp Leu Ser Lys Gln Met Glu Glu
1               5                   10                  15

Glu Ala Val Arg Leu Phe Ile Glu Trp Leu Xaa Gly Trp Leu Asp Phe
            20                  25                  30

<210> SEQ ID NO 73
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 73

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Trp Leu Asp Phe
            20                  25                  30

<210> SEQ ID NO 74
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 74

His Gly Glu Gly Thr Phe Thr Ser Asp Leu Ser Lys Tyr Leu Glu Glu
1               5                   10                  15

Glu Ala Val Arg Leu Phe Ile Glu Trp Leu Lys Xaa Xaa Tyr Gly Trp
            20                  25                  30

Leu Asp Phe
        35

<210> SEQ ID NO 75

```
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 75

His Gly Glu Gly Thr Phe Thr Ser Asp Leu Ser Lys Tyr Met Glu Glu
1               5                   10                  15

Glu Ala Val Arg Leu Phe Ile Glu Phe Leu Lys Xaa Xaa Tyr Gly Trp
            20                  25                  30

Leu Asp Phe
        35

<210> SEQ ID NO 76
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 76

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Xaa Xaa Tyr Gly Trp
            20                  25                  30

Leu Asp Phe
        35

<210> SEQ ID NO 77
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 77

His Gly Glu Gly Thr Phe Thr Ser Asp Leu Ser Lys Tyr Leu Glu Glu
1               5                   10                  15

Glu Ala Val Arg Leu Phe Ile Glu Phe Leu Lys Xaa Xaa Tyr Gly Trp
            20                  25                  30

Leu Asp Phe
        35

<210> SEQ ID NO 78
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3
```

```
<400> SEQUENCE: 78

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Tyr Gly
            20                  25                  30

Trp Leu Asp Phe
        35

<210> SEQ ID NO 79
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 79

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Xaa Xaa Tyr Gly
            20                  25                  30

Trp Leu Asp Phe
        35

<210> SEQ ID NO 80
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 80

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Xaa Xaa Tyr Gly
            20                  25                  30

Trp Leu Asp Phe
        35

<210> SEQ ID NO 81
<211> LENGTH: 36
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(30)
<223> OTHER INFORMATION: Xaa = Peg3

<400> SEQUENCE: 81

His Gly Glu Gly Thr Phe Thr Ser Asp Leu Ser Lys Gln Met Glu Lys
1               5                   10                  15

Glu Ala Val Arg Leu Phe Ile Glu Trp Leu Lys Asn Xaa Xaa Tyr Gly
            20                  25                  30

Trp Leu Asp Phe
        35
```

<210> SEQ ID NO 82
<211> LENGTH: 37
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (29)..(29)
<223> OTHER INFORMATION: Xaa = Peg3
<220> FEATURE:
<221> NAME/KEY: MISC_FEATURE
<222> LOCATION: (31)..(31)
<223> OTHER INFORMATION: Xaa = Peg3

<400> SEQUENCE: 82

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Lys Xaa Tyr
            20                  25                  30

Gly Trp Leu Asp Phe
        35

<210> SEQ ID NO 83
<211> LENGTH: 34
<212> TYPE: PRT
<213> ORGANISM: Artificial
<220> FEATURE:
<223> OTHER INFORMATION: Synthetic peptide sequence

<400> SEQUENCE: 83

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Tyr Gly Trp Thr
            20                  25                  30

Asp Phe

<210> SEQ ID NO 84
<211> LENGTH: 34
<212> TYPE: PRT
<213> ORGANISM: Artificial
<220> FEATURE:
<223> OTHER INFORMATION: Synthetic peptide sequence

<400> SEQUENCE: 84

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Tyr Gly Trp Phe
            20                  25                  30

Asp Phe

<210> SEQ ID NO 85
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (31)..(31)
<223> OTHER INFORMATION: Xaa = 1Nal

<400> SEQUENCE: 85

His Gly Glu Gly Thr Phe Thr Ser Asp Leu Ser Lys Gln Leu Glu Glu

```
                1               5                  10                 15
Glu Ala Val Arg Leu Phe Ile Glu Trp Leu Lys Asn Tyr Gly Xaa Leu
                20                 25                 30

Asp Phe
```

<210> SEQ ID NO 86
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (32)..(32)
<223> OTHER INFORMATION: Xaa = Nle

<400> SEQUENCE: 86

```
His Gly Glu Gly Thr Phe Thr Ser Asp Leu Ser Lys Gln Leu Glu Glu
1               5                  10                 15

Glu Ala Val Arg Leu Phe Ile Glu Trp Leu Lys Asn Tyr Gly Trp Xaa
                20                 25                 30

Asp Phe
```

<210> SEQ ID NO 87
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (34)..(34)
<223> OTHER INFORMATION: Xaa = 3-(3-PYRIDYL)-ALANYL

<400> SEQUENCE: 87

```
His Gly Glu Gly Thr Phe Thr Ser Asp Leu Ser Lys Gln Leu Glu Glu
1               5                  10                 15

Glu Ala Val Arg Leu Phe Ile Glu Trp Leu Lys Asn Tyr Gly Trp Leu
                20                 25                 30

Asp Xaa
```

<210> SEQ ID NO 88
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 88

```
His Gly Glu Gly Thr Phe Thr Ser Glu Leu Ser Lys Tyr Leu Glu Glu
1               5                  10                 15

Glu Ala Val Arg Leu Phe Ile Glu Phe Leu Lys Xaa Xaa Tyr Gly Trp
                20                 25                 30

Leu Asp Phe
        35
```

<210> SEQ ID NO 89
<211> LENGTH: 35
<212> TYPE: PRT
<213> ORGANISM: Artificial

<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 89

His Gly Glu Gly Thr Phe Thr Ser Asp Leu Ser Lys Tyr Leu Glu Glu
1               5                   10                  15

Glu Ala Val Arg Leu Phe Ile Glu Phe Leu Lys Xaa Xaa Tyr Gly Phe
            20                  25                  30

Leu Asp Phe
        35

<210> SEQ ID NO 90
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Peg3

<400> SEQUENCE: 90

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Tyr Gly Phe
            20                  25                  30

Leu Asp Phe
        35

<210> SEQ ID NO 91
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 91

His Gly Glu Gly Thr Phe Thr Ser Asp Leu Ser Lys Tyr Leu Glu Glu
1               5                   10                  15

Glu Ala Val Arg Leu Phe Ile Glu Phe Leu Arg Xaa Tyr Gly Trp Leu
            20                  25                  30

Asp Phe

<210> SEQ ID NO 92
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 92

His Gly Glu Gly Thr Phe Thr Ser Asp Leu Ser Arg Tyr Leu Glu Lys
1               5                   10                  15

```
Glu Ala Val Arg Leu Phe Ile Glu Phe Leu Arg Xaa Tyr Gly Trp Leu
        20                  25                  30

Asp Phe

<210> SEQ ID NO 93
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 93

His Gly Glu Gly Thr Phe Thr Ser Asp Leu Ser Arg Tyr Leu Glu Glu
 1               5                  10                  15

Glu Ala Val Lys Leu Phe Ile Glu Phe Leu Arg Xaa Tyr Gly Trp Leu
        20                  25                  30

Asp Phe

<210> SEQ ID NO 94
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 94

His Gly Glu Gly Thr Phe Thr Ser Asp Leu Ser Arg Tyr Leu Glu Glu
 1               5                  10                  15

Glu Ala Val Arg Leu Phe Ile Lys Phe Leu Arg Xaa Tyr Gly Trp Leu
        20                  25                  30

Asp Phe

<210> SEQ ID NO 95
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 95

His Gly Glu Gly Thr Phe Thr Ser Asp Leu Ser Arg Tyr Leu Glu Glu
 1               5                  10                  15

Glu Ala Val Arg Leu Phe Ile Glu Phe Leu Lys Xaa Tyr Gly Trp Leu
        20                  25                  30

Asp Phe

<210> SEQ ID NO 96
<211> LENGTH: 31
<212> TYPE: PRT
<213> ORGANISM: Artificial
<220> FEATURE:
<223> OTHER INFORMATION: Synthetic peptide sequence
```

```
<400> SEQUENCE: 96

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Trp Leu Asp Phe
            20                  25                  30

<210> SEQ ID NO 97
<211> LENGTH: 32
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 97

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Trp Leu Asp Phe
            20                  25                  30

<210> SEQ ID NO 98
<211> LENGTH: 33
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Orn
<220> FEATURE:
<221> NAME/KEY: MISC_FEATURE
<222> LOCATION: (29)..(29)
<223> OTHER INFORMATION: Xaa = Peg3

<400> SEQUENCE: 98

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Trp Leu Asp
            20                  25                  30

Phe

<210> SEQ ID NO 99
<211> LENGTH: 33
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3
<220> FEATURE:
<221> NAME/KEY: MISC_FEATURE
<222> LOCATION: (29)..(29)
<223> OTHER INFORMATION: Xaa = Orn

<400> SEQUENCE: 99

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Trp Leu Asp
            20                  25                  30
```

Phe

```
<210> SEQ ID NO 100
<211> LENGTH: 33
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Orn

<400> SEQUENCE: 100
```

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Trp Leu Asp
            20                  25                  30

Phe

```
<210> SEQ ID NO 101
<211> LENGTH: 33
<212> TYPE: PRT
<213> ORGANISM: Artificial
<220> FEATURE:
<223> OTHER INFORMATION: Synthetic peptide sequence

<400> SEQUENCE: 101
```

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Tyr Gly Trp Leu Asp
            20                  25                  30

Phe

```
<210> SEQ ID NO 102
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3

<400> SEQUENCE: 102
```

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Tyr Gly Trp Leu
            20                  25                  30

Asp Phe

```
<210> SEQ ID NO 103
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Orn
<220> FEATURE:
<221> NAME/KEY: MISC_FEATURE
<222> LOCATION: (29)..(29)
<223> OTHER INFORMATION: Xaa = Peg3
```

<400> SEQUENCE: 103

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Tyr Gly Trp
            20                  25                  30

Leu Asp Phe
        35

<210> SEQ ID NO 104
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = Peg3
<220> FEATURE:
<221> NAME/KEY: MISC_FEATURE
<222> LOCATION: (29)..(29)
<223> OTHER INFORMATION: Xaa = Orn

<400> SEQUENCE: 104

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Tyr Gly Trp
            20                  25                  30

Leu Asp Phe
        35

<210> SEQ ID NO 105
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(29)
<223> OTHER INFORMATION: Xaa = Orn

<400> SEQUENCE: 105

His Gly Glu Gly Thr Phe Thr Ser Glu Leu Ser Lys Tyr Leu Glu Glu
1               5                   10                  15

Glu Ala Val Arg Leu Phe Ile Glu Phe Leu Lys Xaa Xaa Tyr Gly Trp
            20                  25                  30

Leu Asp Phe
        35

<210> SEQ ID NO 106
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (28)..(28)
<223> OTHER INFORMATION: Xaa = K(Hexadecanoyl-isoglu)
<220> FEATURE:
<221> NAME/KEY: MISC_FEATURE
<222> LOCATION: (32)..(33)
<223> OTHER INFORMATION: Xaa = Peg3

<400> SEQUENCE: 106

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Gly Arg Gly Xaa
            20                  25                  30

Xaa Tyr Gly Trp Leu Asp Phe
        35

<210> SEQ ID NO 107
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (20)..(20)
<223> OTHER INFORMATION: Xaa = K(Hexadecanoyl-isoglu)
<220> FEATURE:
<221> NAME/KEY: MISC_FEATURE
<222> LOCATION: (32)..(33)
<223> OTHER INFORMATION: Xaa = Peg3

<400> SEQUENCE: 107

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly Xaa
            20                  25                  30

Xaa Tyr Gly Trp Leu Asp Phe
        35

<210> SEQ ID NO 108
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (30)..(30)
<223> OTHER INFORMATION: Xaa = K(Hexadecanoyl-isoglu)
<220> FEATURE:
<221> NAME/KEY: MISC_FEATURE
<222> LOCATION: (32)..(33)
<223> OTHER INFORMATION: Xaa = Peg3

<400> SEQUENCE: 108

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Xaa Gly Xaa
            20                  25                  30

Xaa Tyr Gly Trp Leu Asp Phe
        35

<210> SEQ ID NO 109
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (20)..(20)
<223> OTHER INFORMATION: Xaa = K(Hexadecanoyl-isoglu)
<220> FEATURE:
<221> NAME/KEY: MISC_FEATURE
<222> LOCATION: (32)..(33)
<223> OTHER INFORMATION: Xaa = Peg3

<400> SEQUENCE: 109

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Lys Gly Arg Gly Xaa
            20                  25                  30

Xaa Tyr Gly Trp Leu Asp Phe
        35

<210> SEQ ID NO 110
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (30)..(30)
<223> OTHER INFORMATION: Xaa = K(Hexadecanoyl-isoglu)
<220> FEATURE:
<221> NAME/KEY: MISC_FEATURE
<222> LOCATION: (32)..(33)
<223> OTHER INFORMATION: Xaa = Peg3

<400> SEQUENCE: 110

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Xaa Gly Xaa
            20                  25                  30

Xaa Tyr Gly Trp Leu Asp Phe
        35

<210> SEQ ID NO 111
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(20)
<223> OTHER INFORMATION: Xaa = K(Hexadecanoyl-isoglu)
<220> FEATURE:
<221> NAME/KEY: MISC_FEATURE
<222> LOCATION: (32)..(33)
<223> OTHER INFORMATION: Xaa = Peg3

<400> SEQUENCE: 111

His Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly Xaa
            20                  25                  30

Xaa Tyr Gly Trp Leu Asp Phe
        35

<210> SEQ ID NO 112
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (32)..(33)
<223> OTHER INFORMATION: Xaa = Peg3

<400> SEQUENCE: 112

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Xaa
            20                  25                  30

Xaa Tyr Gly Trp Leu Asp Phe
            35
```

<210> SEQ ID NO 113
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (32)..(33)
<223> OTHER INFORMATION: Xaa = Peg3

<400> SEQUENCE: 113

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Xaa
            20                  25                  30

Xaa Tyr Gly Trp Leu Asp Phe
            35
```

<210> SEQ ID NO 114
<211> LENGTH: 31
<212> TYPE: PRT
<213> ORGANISM: Artificial
<220> FEATURE:
<223> OTHER INFORMATION: Synthetic peptide sequence

<400> SEQUENCE: 114

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 115
<211> LENGTH: 39
<212> TYPE: PRT
<213> ORGANISM: Artificial
<220> FEATURE:
<223> OTHER INFORMATION: Synthetic peptide sequence

<400> SEQUENCE: 115

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
            35
```

<210> SEQ ID NO 116
<211> LENGTH: 17

```
<212> TYPE: PRT
<213> ORGANISM: artificial
<220> FEATURE:
<223> OTHER INFORMATION: Synthetic peptide sequence
<220> FEATURE:
<221> NAME/KEY: MISC_FEATURE
<222> LOCATION: (15)..(15)
<223> OTHER INFORMATION: Xaa is selected from Leu, Nle, Phe and Thr

<400> SEQUENCE: 116

Gln Gly Pro Trp Leu Glu Glu Glu Glu Ala Tyr Gly Trp Xaa Asp
1               5                   10                  15

Phe
```

PEPTIDE CONJUGATES OF GLP-1 RECEPTOR AGONISTS AND GASTRIN AND THEIR USE

CROSS-REFERENCE TO RELATED APPLICATIONS

This application is the U.S. National Stage of the International Patent Application No. PCT/DK2011/050133, filed Apr. 27, 2011, which claims the benefit of Denmark Patent Application No. PA 2010 00379, filed Apr. 27, 2010, U.S. Provisional Application No. 61/395,119, filed May 7, 2010, Denmark Patent Application No. PA 2010 00941, filed Oct. 15, 2010, Denmark Patent Application No. PA 2011 00149, filed Mar. 4, 2011, and U.S. Provisional Application No. 61/470,170, filed Mar. 31, 2011.

The present application claims benefit of priority to U.S. Patent No. 61/395,119 and 61/470,170, the specifications of which are each incorporated herein by reference in its entirety.

FIELD OF THE INVENTION

The present invention relates, inter alia, to certain peptide conjugates, and to the use of the conjugates in the treatment of a variety of diseases or disorders, including diabetes (type 1 and/or type 2) and diabetes-related diseases or disorders.

BACKGROUND OF THE INVENTION

Diabetes, notably type 1 and type 2 diabetes, together with obesity, which is believed to be a major causal factor in development of, in particular, type 2 diabetes, constitute a growing and worldwide major health problem. Diseases or disorders that may develop as a consequence of untreated diabetes include cardiovascular and peripheral artery disease, micro- and macrovascular complications, stroke and possibly certain forms of cancer.

Diabetes is characterized by a defective physiological regulation of blood glucose levels, and among underlying conditions that may lead to diabetes are reduction in or loss of pancreatic β-cell mass and function, with attendant reduction in or loss of endogenous Insulin production, and/or Insulin resistance (reduced sensitivity to Insulin), i.e. reduction in or loss of the ability of endogenous Insulin to bring about adequate regulation of blood glucose levels.

A number of hormones that lower blood glucose levels are secreted by the gastrointestinal mucosa in response to the presence and absorption of nutrients in the gut. These include glucagon-like peptide-1 (GLP-1), glucose-dependent insulinotropic peptide (GIP) and Secretin.

GLP-1 [see, e.g., Ørskov, *Diabetologia* 35: 701-711 (1992)] is produced by tissue processing of proglucagon, a 180 amino acid peptide [see, e.g., Drucker, *Diabetes* 47: 159-169 (1998)]. The overall sequence of proglucagon contains the 29 amino acid sequence of glucagon, the 36 or 37 amino acid sequence of GLP-1, as well as the 34 amino acid sequence of glucagon-like peptide-2 (GLP-2; an intestinotrophic peptide). Human GLP-1(7-37) has the amino acid sequence HAEGTFTSDVSSYLEGQAAKEFI-AWLVKGRG (SEQ ID NO: 114).

GLP-1 has been identified as having a number of functions. It is a hormone that enhances glucose-stimulated Insulin secretion in normal humans (and therefore belongs to a group of hormones known as incretin hormones). In addition, GLP-1 lowers glucagon concentrations, delays gastric emptying, stimulates (pro)Insulin biosynthesis, and enhances Insulin sensitivity [see, e.g., Nauck, *Horm. Metab. Res.* 47: 1253-1258 (1997)]. GLP-1 also enhances the ability of pancreatic β-cells to sense and respond (by Insulin secretion) to glucose in subjects with impaired glucose tolerance [see, e.g., Byrne, *Eur. J. Clin. Invest.* 28: 72-78 (1998)]. The insulinotropic effect of GLP-1 in humans increases the rate of glucose disappearance and decreases endogenous glucose production, partly because of increase in Insulin levels and partly because of enhancement of Insulin sensitivity [see, e.g., D'Alessio, *Eur. J. Clin. Invest.* 28: 72-78 (1994)]. However, the short half-life of native GLP-1 in vivo has constituted a major pharmacological challenge in attempts to exploit the hormone as a drug. In humans and rats, GLP-1 is rapidly degraded by dipeptidyl peptidase-IV (DPP-IV) to GLP-1(9-36)amide, that acts as an endogenous GLP-1 receptor antagonist. Several strategies for circumventing this problem have been proposed, some of which employ inhibitors of DPP-IV, while others employ DPP-IV resistant analogues of GLP-1 (7-36)amide.

The so-called Exendins, which constitute another group of peptides that lower blood glucose levels, have some sequence similarity (53%) to GLP-1(7-36) [see, e.g., Goke et al., *J. Biol. Chem.* 268: 19650-19655 (1993)]. The Exendins are found in the saliva of Helodermatidae species (beaded lizards). Exendin-3 is present in the saliva of *Heloderma horridum* (Mexican beaded lizard), while Exendin-4 is present in the saliva of *Heloderma suspectum* (Gila monster). The amino acid sequence of Exendin-4, which differs from that of Exendin-3 at positions two and three, is HGEGTFTSDL-SKQMEEEAVRLFIEWLKNGGPSSGAPPPS-NH$_2$ (SEQ ID NO: 115).

Exendin-4 has been reported to be a potent GLP-1 receptor agonist on isolated rat insulinoma cells [Goke et al., loc. cit.]. WO 99/07404 discloses that Exendin-4 administered systemically lowers blood glucose levels by 40% in diabetic db/db mice, and a long-lasting blood glucose lowering effect of once-daily intraperitoneal injection of Exendin-4 in diabetic ob/ob mice has also been reported [Grieg et al., *Diabetologia* 42: 45-50 (1999)].

U.S. Pat. No. 5,424,286 and WO 98/05351 disclose that Exendin-3, Exendin-4 and Exendin agonists may be used for the treatment of diabetes, for reducing gastric motility and delaying gastric emptying, and for prevention of hyperglycemia, and WO 98/30231 further discloses that they may be used for reducing food intake.

The peptide hormone Gastrin is secreted from cells in the gastric mucosa and from G cells in the duodenum, and among the major physiological roles of the hormone in humans are stimulation of secretion of gastric acid (i.e. HCl) and aiding in gastric motility. Other identified effects of Gastrin include stimulation of cell growth, and there are indications that Gastrin may play a role in islet neogenesis, i.e. stimulation of Insulin-secreting β-cell growth in the pancreatic islets [see, e.g., Korc, M., *J. Clin. Invest.*, 92: 1113-1114 (1993); Rooman et al. *Diabetes* 51: 686-690 (2002)], and thereby contribute to regulation of blood glucose.

Gastrin shares receptors with another gastrointestinal peptide hormone, Cholecystokinin (CCK). The receptors CCK-A R and CCK-B R have different affinities for Gastrin and CCK variants. CCK-A R (or CCK R1) acts primarily as a receptor for sulfated CCK, whereas CCK-B R (or CCK R2) binds both CCK and Gastrin equally well. CCK-B R is considered to be the "Gastrin receptor" due to the higher levels of Gastrin compared to CCK in plasma [Foucaud et al. *Reg. Peptides* 145: 17-23 (2008)].

CCK-B R can initiate several intracellular pathways upon binding of ligand, which is considered to be the reason for the diverse physiological roles of CCK. A key pathway downstream of CCK-B R is the MAPK (mitogen activated protein kinases) or ERK (extra-cellular regulated kinases) pathway, which is also activated by several growth hormones. This is a key feature in the cell proliferation role of Gastrin. Since CCK-B R is expressed in the pancreas, Gastrin is able to contribute to cell proliferation and islet regeneration in this tissue.

In humans, Gastrin occurs primarily in three forms, viz. Gastrin34, Gastrin17 and Gastrin14 (with reference to the total number of amino acids in the sequence in question). Gastrin6 has also been identified. The shorter forms are generated by cleavage of C-terminally amidated Gastrin34; thus Gastrin17 consists of the C-terminally last 17 residues of Gastrin34 (corresponding to Progastrin (55-71), Gastrin14 the C-terminally last 14 residues (corresponding to Progastrin (58-71), and Gastrin6 only the C-terminally last 6 residues (corresponding to Progastrin(66-71). It is the amidated forms of Gastrin that bind with high affinity to CCK-B R and exert cell proliferative functions. In human Gastrin17 the N-terminal amino acid residue is a pyroglutamic acid (PyroGlu) residue. The amidated C-terminal 6 amino acids are the key receptor-binding residues of Gastrin.

WO 2005/072045 discloses, inter alia, combinations of "GLP-1 agonists" and "Gastrin compounds" reputedly having beneficial effects in the prevention and/or treatment of conditions and/or diseases for which either a "GLP-1 agonist" or a "Gastrin compound" have been demonstrated to have a therapeutic effect. WO 2007/095737 discloses, inter alia, analogous combinations of "Exendin agonists" and "Gastrin compounds" that reputedly likewise have beneficial effects in the prevention and/or treatment of conditions and/or diseases for which either "Exendin agonists" or "Gastrin compounds" have been demonstrated to have a therapeutic effect.

Data [deriving from studies employing non-obese diabetic (NOD) mice, widely employed as an animal model for human type 1 diabetes] presented in WO 2005/072045 appear to indicate that certain "GLP-1 agonist"/"Gastrin compound" combinations described therein may have a beneficial effect with respect to normalizing blood glucose levels in acutely diabetic NOD mice compared to the effect seen when employing the "GLP-1 agonist" (or the "Gastrin compound") in question alone. Data [likewise deriving from studies employing non-obese diabetic (NOD) mice] presented in WO 2007/095737 appear to indicate that certain "Exendin agonist"/"Gastrin compound" combinations described therein may have a beneficial effect with respect to normalizing blood glucose and Insulin levels in acutely diabetic NOD mice compared to the effect seen when employing the "Exendin agonist" (or the "Gastrin compound") in question alone, and that certain "GLP-1 receptor agonist"/Gastrin combinations described therein may have a beneficial effect with respect to inducing islet cell regeneration compared to the effect seen when employing the "GLP-1 receptor agonist" alone.

WO 2005/072045 and WO 2007/095737 also disclose the possibility of forming conjugates comprising a "GLP-1 agonist" or "Exendin agonist", respectively, and a "Gastrin compound" covalently coupled or linked (i.e. conjugated) to one another, optionally via an intermediate linker or spacer. As a suitable spacer is mentioned a mono- or disaccharide, an amino acid, a sulfate, a succinate, an acetate, or an oligomeric polymeric spacer or linker comprising one or more of such moieties. Contemplated methods by which conjugates of the types in question might be prepared are also described. However, no preparative or other data are provided in either of the latter documents in question to substantiate that any conjugate of the type in question had in fact been prepared and characterized—or tested with respect to its biological/physiological properties or activity—at the time of filing of the respective international application.

It may further be noted that neither WO 2005/072045 nor WO 2007/095737 provide any in vivo, in vitro or other data to substantiate that the "GLP-1 agonist"/"Gastrin compound" or "Exendin agonist"/"Gastrin compound" combinations, respectively, described and utilized therein might be beneficial in the treatment, for example, of type 2 diabetes.

SUMMARY OF THE INVENTION

It has now been found that certain conjugates comprising two covalently coupled or linked peptide moieties may exhibit unexpectedly high therapeutic activity in the treatment, for example, of diabetes (type 1 and/or type 2 diabetes), or of various other diabetes-related diseases or disorders, by comparison with the therapeutic activity of a combination of the two individual peptides in question.

In a broad aspect, the invention provides a peptide conjugate of a GLP-1 receptor agonist and Gastrin, in particular Gastrin with a substitution at position 15 selected from Leu, Nle, Phe and Thr. More particularly, the invention provides peptide conjugates of Exendin-4 and Gastrin as well as peptide conjugates of GLP-1 and Gastrin.

In a first aspect, the invention thus provides a peptide conjugate having the formula I

wherein
$R^1$ is H, $C_{1-4}$ alkyl, acetyl, formyl, benzoyl or trifluoroacetyl;
$R^2$ is OH or $NH_2$;
Z comprises the sequence of Exendin-4(1-39) having the sequence

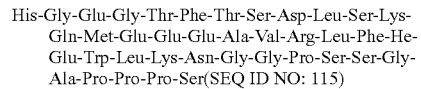

or an analogue thereof $Z_a$;
L is an optional linker moiety; and
Y comprises the sequence of Gastrin17 having the sequence Gln-Gly-Pro-Trp-Leu-Glu-Glu-Glu-Glu-Glu-Ala-Tyr-Gly-Trp-Y15-Asp-Phe (SEQ ID NO: 116)
wherein Y15 is selected from Leu, Nle, Phe and Thr
or an analogue thereof $Y_a$.

Further, the invention provides a peptide conjugate wherein:
(i) $Z_a$ has substitutions in up to 10 positions, and/or comprises a C-terminal truncation of 1 to 12 amino acids, with respect to the sequence of Exendin-4; and/or
(ii) $Y_a$ has substitutions in up to 5 positions with respect to the sequence of Gastrin17, and/or comprises an N-terminal truncation from 1 to 13 amino acids, with respect to the sequence of Gastrin17.

In one embodiment, the invention provides a peptide conjugate wherein
$Z_a$ is a peptide sequence having the formula IIa

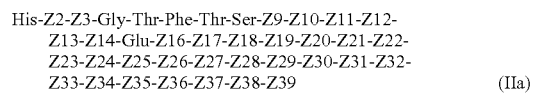

wherein
Z2 is selected from Gly, Ala, Ser, Aib, Thr, Leu and Ile;
Z3 is selected from Glu and Asp;

Z9 is selected from Asp and Glu;
Z10 is selected from Leu, Val, Ile and Ala;
Z11 is selected from Ser and Aib;
Z12 is selected from Ser, Gln, Arg, Cys, Lys, Glu and Orn;
Z13 is selected from Arg, Ser, Gln, Tyr and Glu;
Z14 is selected from Gly, Cys, Phe, Tyr, Trp, Lys, Met, Leu, Nle and Ile;
Z16 is selected from Asp, Gly, Aib, Glu, Lys and Cys;
Z17 is selected from Glu, Cys, Lys, Ser and Gln;
Z18 is selected from Ala and Aib;
Z19 is selected from Val, Leu, Ile and Ala;
Z20 is selected from Arg, Lys, Cys, Orn and Glu;
Z21 is selected from Leu and Glu;
Z22 is selected from Phe and Ala;
Z23 is selected from Ile and Leu;
Z24 is selected from Glu, Cys, Lys, Ala and Arg;
Z25 is selected from Trp, Cys, Lys and Phe;
Z26 is selected from Leu and Ile;
Z27 is selected from Ile, Val, Gln, Lys, Cys, Arg and Orn;
Z28 is selected from Asn, Ser, Asp, Aib, Gln, Lys, Cys, Arg, Tyr, bAla, Glu, Orn and Leu or is absent;
Z29 is selected from Gly, Aib and bAla or is absent;
Z30 is selected from Gly, Cys, Lys and Arg or is absent;
Z31 is selected from Pro, Ser and Asp or is absent;
Z32 is selected from Ser and Lys or is absent;
Z33 is Ser or is absent;
Z34 is selected from Gly and Lys or is absent;
Z35 is Ala or is absent;
Z36 is Pro or is absent;
Z37 is Pro or is absent;
Z38 is Pro or is absent;
Z39 is Ser or is absent;
L is a peptide sequence having the formula IIb $$L1\text{-}L2\text{-}L3\text{-}L4 \tag{IIb}$$

wherein
L1 is selected from Ser, Ala, Lys, Orn, bAla, 8Aoc, DBF, Peg3, Cys and Gln or is absent;
L2 is selected from Ser, Ala, Lys, Orn, bAla, 8Aoc, DBF, Peg3, Cys and Gln or is absent;
L3 is selected from Ser, Ala, Lys, Orn, bAla, 8Aoc, DBF, Peg3, Cys and Gln or is absent;
L4 is selected from Ser, Ala, Lys, Orn, bAla, 8Aoc, DBF, Peg3, Cys and Gln or is absent;
$Y_a$ is a peptide sequence having the formula IIc $$Y1\text{-}Y2\text{-}Y3\text{-}Y4\text{-}Y5\text{-}Y6\text{-}Y7\text{-}Y8\text{-}Y9\text{-}Y10\text{-}Y11\text{-}Y12\text{-}Y13\text{-}Y14\text{-}Y15\text{-}Asp\text{-}Y17 \tag{IIc}$$

wherein
Y1 is Gln or is absent;
Y2 is Gly or is absent;
Y3 is Pro or is absent;
Y4 is Trp or is absent;
Y5 is Leu or is absent;
Y6 is Glu or is absent;
Y7 is Glu or is absent;
Y8 is Glu or is absent;
Y9 is Glu or is absent;
Y10 is Glu or is absent;
Y11 is Ala or is absent;
Y12 is selected from Ala and Tyr or is absent;
Y13 is selected from Gly and Ala or is absent;
Y14 is selected from Trp, Phe, 1 NaI and Met;
Y15 is selected from Leu, Nle, Phe and Thr; and
Y17 is selected from Phe and 3-(3-Pyridyl)-alanine.

In another embodiment, the invention provides a peptide conjugate wherein
$Z_a$ is a peptide sequence having the formula IIIa $$\text{His-Gly-Glu-Gly-Thr-Phe-Thr-Ser-Z9-Leu-Ser-Z12-} \\ \text{Z13-Z14-Glu-Z16-Glu-Ala-Val-Z20-Leu-Phe-} \\ \text{Ile-Z24-Z25-Leu-Z27-Z28} \tag{IIIa}$$

wherein
Z9 is selected from Asp and Glu;
Z12 is selected from Lys, Arg and Orn;
Z13 is selected from Gln and Tyr;
Z14 is selected from Met and Leu;
Z16 is selected from Glu, Cys and Lys;
Z20 is selected from Arg, Lys and Orn;
Z24 is selected from Lys and Glu;
Z25 is selected from Trp, Lys, Cys and Phe;
Z27 is selected from Lys, Arg and Orn;
Z28 is selected from Asn and Asp or is absent;
L is a peptide sequence having the formula IIIb $$L1\text{-}L2\text{-}L3\text{-}L4 \tag{IIIb}$$

wherein
L1 is selected from Orn, Peg3, Cys, Lys and Gln or is absent;
L2 is selected from Orn, Peg3, Cys, Lys and Gln or is absent;
L3 is selected from Orn, Peg3, Cys, Lys and Gln or is absent;
L4 is selected from Orn, Peg3, Cys, Lys and Gln or is absent;
$Y_a$ is a peptide sequence having the formula IIIc $$Y12\text{-}Y13\text{-}Y14\text{-}Y15\text{-}Asp\text{-}Y17 \tag{IIIc}$$

wherein
Y12 is selected from Tyr and Ala or is absent;
Y13 is selected from Gly and Ala or is absent;
Y14 is selected from Trp, 1 NaI and Phe;
Y15 is selected from Leu, Nle, Thr and Phe; and
Y17 is selected from Phe and 3-(3-pyridyl)-alanine.

In a further embodiment, the invention provides a peptide conjugate wherein
$Z_a$ is a peptide sequence having the formula IVa $$\text{His-Gly-Glu-Gly-Thr-Phe-Thr-Ser-Z9-Leu-Ser-Z12-} \\ \text{Gln-Met-Glu-Z16-Glu-Ala-Val-Arg-Leu-Phe-Ile-} \\ \text{Glu-Trp-Leu-Z27-Z28} \tag{IVa}$$

wherein
Z9 is selected from Glu and Asp;
Z12 is selected from Lys and Orn;
Z16 is selected from Glu and Lys;
Z27 is selected from Lys and Orn;
Z28 is selected from Asn and Asp or is absent;
L is a peptide sequence having the formula IVb $$L1\text{-}L2\text{-}L3\text{-}L4 \tag{IVb}$$

wherein
L1 is selected from Orn, Peg3, Cys, Lys and Gln or is absent;
L2 is selected from Orn, Peg3, Cys, Lys and Gln or is absent;
L3 is selected from Orn, Peg3, Cys, Lys and Gln or is absent;
L4 is selected from Orn, Peg3, Cys, Lys and Gln or is absent;
$Y_a$ is a peptide sequence having the formula IVc $$Y12\text{-}Y13\text{-}Trp\text{-}Leu\text{-}Asp\text{-}Phe \tag{IVc}$$

wherein
Y12 is Tyr or is absent; and
Y13 is Gly or is absent.

In a still further embodiment, the invention provides a peptide conjugate wherein
$Z_a$ is a peptide sequence having the formula Va $$\text{His-Gly-Glu-Gly-Thr-Phe-Thr-Ser-Z9-Leu-Ser-Z12-} \\ \text{Tyr-Leu-Glu-Z16-Glu-Ala-Val-Arg-Leu-Phe-Ile-} \\ \text{Glu-Phe-Leu-Z27-Z28} \tag{Va}$$

wherein

Z9 is selected from Glu and Asp;
Z12 is selected from Lys and Orn;
Z16 is selected from Glu and Lys;
Z27 is selected from Lys and Orn;
Z28 is selected from Asn and Asp or is absent;
L is a peptide sequence having the formula Vb L1-L2-L3-L4 (Vb)

wherein
L1 is selected from Orn, Peg3, Cys, Lys and Gln or is absent;
L2 is selected from Orn, Peg3, Cys, Lys and Gln or is absent;
L3 is selected from Orn, Peg3, Cys, Lys and Gln or is absent;
L4 is selected from Orn, Peg3, Cys, Lys and Gln or is absent;
$Y_a$ is a peptide sequence having the formula Vc Y12-Y13-Trp-Leu-Asp-Phe (Vc)

wherein
Y12 is Tyr or is absent; and
Y13 is Gly or is absent.

Further, the invention provides a peptide conjugate wherein the peptide sequence of formula I comprises one or more intramolecular bridges.

Still further, the invention provides a peptide conjugate wherein said intramolecular bridge is formed between the side chains of two amino acid residues which are separated by three amino acids in the linear amino acid sequence of formula I.

In a specific embodiment, the invention provides a peptide conjugate wherein the intramolecular bridge is formed between the side chains of residue pairs x and x+3, x+4, x+5 etc.

In another specific embodiment, the invention provides a peptide conjugate wherein the intramolecular bridge is a lactam ring.

In a further specific embodiment, the invention provides a peptide conjugate wherein the intramolecular bridge involves a pair of residues wherein:
Z12 is Lys and Z16 is Glu; Z12 is Glu and Z16 is Lys;
Z16 is Glu and Z20 is Lys; Z16 is Lys and Z20 is Glu;
Z20 is Glu and Z24 is Lys; Z20 is Lys and Z24 is Glu;

In another aspect of the invention is provided a peptide conjugate having the formula VI:

$R^1$—X-L-Y—$R^2$ (VI)

wherein
$R^1$ is H, $C_{1-4}$ alkyl, acetyl, formyl, benzoyl or trifluoroacetyl;
$R^2$ is OH or $NH_2$;
X comprises the sequence of GLP-1(7-36) having the sequence His-Ala-Glu-Gly-Thr-Phe-Thr-Ser-Asp-Val-Ser-Ser-
Tyr-Leu-Glu-Gly-Gln-Ala-Ala-Lys-Glu-Phe-Ile-
Ala-Trp-Leu-Val-Lys-Gly-Arg(SEQ ID NO: 114)

or an analogue thereof Xa;
L is a linker containing up to 4 naturally or non-naturally amino acids or combinations thereof or is absent;
Y comprises the sequence of Gastrin-17 having the sequence Gln-Gly-Pro-Trp-Leu-Glu-Glu-Glu-Glu-Glu-Ala-Tyr-
Gly-Trp-Y15-Asp-Phe wherein Y15 is selected from Leu, Nle, Phe and Thr or an analogue thereof $Y_a$.

In one embodiment, the invention provides a peptide conjugate wherein (i) $X_a$ has substitutions in up to 5 positions and/or comprises a C-terminally truncation of 1-2 amino acids, with respect to the sequence of GLP-1; and/or (ii) $Y_a$ has substitutions in up to 5 positions with respect to the sequence of Gastrin17, and/or comprises an N-terminal truncation of 1 to 13 amino acids, with respect to the sequence of Gastrin17.

In another embodiment, the invention provides a peptide conjugate wherein
$X_a$ is a peptide sequence having the formula VIIa His-X8-Glu-Gly-Thr-Phe-Thr-Ser-Asp-Val-Ser-Ser-
Tyr-Leu-Glu-Gly-Gln-Ala-Ala-X26-Glu-Phe-Ile-
Ala-Trp-Leu-Val-X34-Gly-X36 (VIIa)

wherein
X8 is selected from Ala, Aib and Gly;
X26 is selected from Arg and Lys;
X34 is selected from Arg and Lys;
X36 is selected from Arg and Lys;
L is a peptide sequence having the formula VIIb L1-L2-L3-L4 (VIIb)

wherein
L1 is selected from Ser, Ala, Lys, Orn, bAla, 8Aoc, DBF, Peg3, Cys, Gln or is absent;
L2 is selected from Ser, Ala, Lys, Orn, bAla, 8Aoc, DBF, Peg3, Cys, Gln or is absent;
L3 is selected from Ser, Ala, Lys, Orn, bAla, 8Aoc, DBF, Peg3, Cys, Gln or is absent;
L4 is selected from Ser, Ala, Lys, Orn, bAla, 8Aoc, DBF, Peg3, Cys, Gln or is absent;
$Y_a$ is a peptide sequence having the formula VIIc Y1-Y2-Y3-Y4-Y5-Y6-Y7-Y8-Y9-Y10-Y11-Y12-
Y13-Y14-Y15-Asp-Y17 (VIIc)

wherein
Y1 is Gln or is absent;
Y2 is Gly or is absent;
Y3 is Pro or is absent;
Y4 is Trp or is absent;
Y5 is Leu or is absent;
Y6 is Glu or is absent;
Y7 is Glu or is absent;
Y8 is Glu or is absent;
Y9 is Glu or is absent;
Y10 is Glu or is absent;
Y11 is Ala or is absent;
Y12 is selected from Ala, Tyr or is absent;
Y13 is selected from Gly, Ala or is absent;
Y14 is selected from Trp, Phe, 1 NaI and Met;
Y15 is selected from Leu, Nle, Phe and Thr: and
Y17 is selected from Phe and 3-(3-pyridyl)-alanine.

In still another embodiment, the invention provides a peptide conjugate wherein
$X_a$ is a peptide sequence having the formula VIIIa His-X8-Glu-Gly-Thr-Phe-Thr-Ser-Asp-Val-Ser-Ser-
Tyr-Leu-Glu-Gly-Gln-Ala-Ala-X26-Glu-Phe-Ile-
Ala-Trp-Leu-Val-X34-Gly-X36 (VIIIa)

wherein
X8 is selected from Ala, Aib and Gly;
X26 is selected from Arg and Lys;
X34 is selected from Arg and Lys;
X36 is selected from Arg and Lys;
L is a peptide sequence having the formula VIIIb L1-L2-L3-L4 (VIIIb)

wherein
L1 is selected from Peg3, Orn, Cys, Lys, Gln or is absent;
L2 is selected from Ser, Ala, Orn, Cys, Lys, Gln or is absent;
L3 is selected from Lys, Ala, Cys, Orn, Gln or is absent;

L4 is selected from Lys, Orn, Ala, Peg3, Cys, Lys, Gln or is absent;

$Y_a$ is a peptide sequence having the formula VIIIc

Y12-Y13-Y14-Y15-Asp-Phe (VIIIc)

wherein
Y12 is selected from Tyr, Ala or is absent;
Y13 is selected from Gly, Ala or is absent;
Y14 is selected from Trp and Phe; and
Y15 is selected from Leu, Thr and Phe.

In a specific embodiment, the invention provides a peptide conjugate wherein $X_a$ is a peptide sequence having the formula IXa His-X8-Glu-Gly-Thr-Phe-Thr-Ser-Asp-Val-Ser-Ser-Tyr-Leu-Glu-Gly-Gln-Ala-Ala-X26-Glu-Phe-Ile-Ala-Trp-Leu-Val-X34-Gly-X36 (IXa)

wherein
X8 is selected from Ala, Aib and Gly;
X26 is selected from Arg and Lys;
X34 is selected from Arg and Lys;
X36 is selected from Arg and Lys;
L is a peptide sequence having the formula IXb L1-L2-L3-L4 (IXb)

wherein
L1 is selected from Orn, Peg3, Cys, Lys and Gln or is absent;
L2 is selected from Orn, Peg3, Cys, Lys and Gln or is absent;
L3 is selected from Orn, Peg3, Cys, Lys and Gln or is absent;
L4 is selected from Orn, Peg3, Cys, Lys and Gln or is absent;
$Y_a$ is a peptide sequence having the formula IXc Y12-Y13-Trp-Leu-Asp-Phe (IXc)

wherein
Y12 is Tyr or is absent; and
Y13 is Gly or is absent.

In a further specific embodiment, the invention provides a peptide conjugate wherein at least one of Lys or Cys is further conjugated to a lipophilic substituent.

A a further aspect of the invention relates to a peptide conjugate having the formula:

| | |
|---|---|
| Exendin-4(1-39)-Peg3-Peg3-[Gln1,Leu15]Gastrin17, | (1) |
| Exendin-4(1-39)-[Gln1,Leu15]Gastrin17, | (2) |
| Exendin-4(1-39)-K-[Gln1,Leu15]Gastrin17, | (3) |
| Exendin-4(1-39)-AAA-[Gln1,Leu15]Gastrin17, | (4) |
| Exendin-4(1-39)-SKK-[Gln1,Leu15]Gastrin17, | (5) |
| Exendin-4(1-39)-Peg3-SKK-[Gln1,Leu15]Gastrin17, | (6) |
| Exendin-4(1-39)-8Aoc-SKK-[Gln1,Leu15]Gastrin17, | (7) |
| Exendin-4(1-39)-DBF-SKK-[Gln1,Leu15]Gastrin17, | (8) |
| Exendin-4(1-39)-8Aoc-8Aoc-[Gln1,Leu15]Gastrin17, | (9) |
| Exendin-4(1-39)-[Leu4]Gastrin6, | (10) |
| Exendin-4(1-39)-K-[Leu4]Gastrin6, | (11) |
| Exendin-4(1-39)-AAA-[Leu4]Gastrin6, | (12) |
| Exendin-4(1-39)-SKK-[Leu4]Gastrin6, | (13) |
| Exendin-4(1-39)-Peg3-SKK-[Leu4]Gastrin6, | (14) |
| Exendin-4(1-39)-Peg3-Peg3-[Leu4]Gastrin6, | (15) |
| Exendin-4(1-39)-8Aoc-SKK-[Leu4]Gastrin6, | (16) |
| Exendin-4(1-39)-DBF-SKK-[Leu4]Gastrin6, | (17) |
| Exendin-4(1-39)-8Aoc-8Aoc-[Leu4]Gastrin6, | (18) |
| Exendin-4(1-28)-[Gln1,Leu15]Gastrin17, | (19) |
| Exendin-4(1-28)-K-[Gln1,Leu15]Gastrin17, | (20) |
| Exendin-4(1-28)-AAA-[Gln1,Leu15]Gastrin17, | (21) |
| Exendin-4(1-28)-SKK-[Gln1,Leu15]Gastrin17, | (22) |
| Exendin-4(1-28)-Peg3-SKK-[Gln1,Leu15]Gastrin17, | (23) |
| Exendin-4(1-28)-Peg3-Peg3-[Gln1,Leu15]Gastrin17, | (24) |
| Exendin-4(1-28)-8Aoc-SKK-[Gln1,Leu15]Gastrin17, | (25) |
| Exendin-4(1-28)-DBF-SKK-[Gln1,Leu15]Gastrin17, | (26) |
| Exendin-4(1-28)-8Aoc-8Aoc-[Gln1,Leu15]Gastrin17, | (27) |
| Exendin-4(1-28)-[Leu4]Gastrin6, | (28) |
| Exendin-4(1-28)-K-[Leu4]Gastrin6, | (29) |
| Exendin-4(1-28)-AAA-[Leu4]Gastrin6, | (30) |
| Exendin-4(1-28)-SKK-[Leu4]Gastrin6, | (31) |
| Exendin-4(1-28)-Peg3-SKK-[Leu4]Gastrin6, | (32) |
| Exendin-4(1-28)-Peg3-Peg3-[Leu4]Gastrin6, | (33) |
| Exendin-4(1-28)-8Aoc-SKK-[Leu4]Gastrin6, | (34) |
| Exendin-4(1-28)-DBF-SKK-[Leu4]Gastrin6, | (35) |
| Exendin-4(1-28)-8Aoc-8Aoc-[Leu4]Gastrin6, | (36) |
| GLP-1(7-36)-[Gln1,Leu15]Gastrin17, | (37) |
| GLP-1(7-36)-K-[Gln1,Leu15]Gastrin17, | (38) |
| GLP-1(7-36)-AAA-[Gln1,Leu15]Gastrin17, | (39) |
| GLP-1(7-36)-SKK-[Gln1,Leu15]Gastrin17, | (40) |
| GLP-1(7-36)-Peg3-SKK-[Gln1,Leu15]Gastrin17, | (41) |
| GLP-1(7-36)-Peg3-Peg3-[Gln1,Leu15]Gastrin17, | (42) |
| GLP-1(7-36)-8Aoc-SKK-[Gln1,Leu15]Gastrin17, | (43) |
| GLP-1(7-36)-DBF-SKK-[Gln1,Leu15]Gastrin17, | (44) |
| GLP-1(7-36)-8Aoc-8Aoc-[Gln1,Leu15]Gastrin17, | (45) |
| GLP-1(7-36)-[Leu4]Gastrin6, | (46) |
| GLP-1(7-36)-K-[Leu4]Gastrin6, | (47) |
| GLP-1(7-36)-AAA-[Leu4]Gastrin6, | (48) |
| GLP-1(7-36)-SKK-[Leu4]Gastrin6, | (49) |
| GLP-1(7-36)-Peg3-SKK-[Leu4]Gastrin6, | (50) |
| GLP-1(7-36)-Peg3-Peg3-[Leu4]Gastrin6, | (51) |

GLP-1(7-36)-8Aoc-SKK-[Leu4]Gastrin6, (52)

GLP-1(7-36)-DBF-SKK-[Leu4]Gastrin6 (53)

or

GLP-1(7-36)-8Aoc-8Aoc-[Leu4]Gastrin6, (54)

wherein each of the Exendin-4(1-39), the Exendin-4(1-28) and the GLP-1(7-36) peptide moieties is covalently attached (i.e. linked or coupled) to the remaining part of the respective conjugate molecule via its C-terminal, and each of the [Gln1, Leu15]Gastrin17 and [Leu4]Gastrin6 peptide moieties is covalently attached (i.e. linked or coupled) to the remaining part of the respective conjugate molecule via its N-terminal; or a pharmaceutically acceptable salt or solvate thereof.

In a specific aspect, the peptide conjugates of the invention may be manufactured by standard synthetic methods, by use of recombinant expression systems, or by any other suitable method. Thus, the conjugates may be synthesized in a number of ways, including, e.g., methods which comprise:
(a) synthesizing the peptide conjugate by means of standard solid-phase or liquid-phase methodology, either stepwise or by fragment assembly, and isolating and purifying the final peptide conjugate product;
(b) expressing a nucleic acid construct that encodes the peptide conjugate in a host cell and recovering the expression product from the host cell culture; or
(c) effecting cell-free in vitro expression of a nucleic acid construct that encodes the peptide conjugate, and recovering the expression product;
or by any combination of methods of (a), (b) or (c) to obtain fragments of the peptide conjugate, subsequently ligating the fragments to obtain the peptide conjugate, and recovering the peptide conjugate.

Among further aspects of the invention are methods of treatment of a variety of conditions, diseases or disorders [including diabetes (type 1 and type 2) and various diabetes-related conditions, diseases or disorders] comprising administration of a peptide conjugate of the invention (in free form or in the form of a pharmaceutically acceptable salt or solvate thereof), as well as pharmaceutical compositions comprising a peptide conjugate or pharmaceutically acceptable salt or solvate thereof of the invention.

In a specific aspect, the peptide conjugates of the present invention may also be useful as pharmaceutical agents for treatment of Insulin resistance, glucose intolerance, pre-diabetes, elevated fasting glucose levels, type 1 and/or type 2 diabetes, hypertension and/or dyslipidemia (or a combination of these metabolic risk factors), atherosclerosis, arteriosclerosis, coronary heart disease, peripheral artery disease and stroke. They may also be useful in preventing weight gain, promoting weight loss, reducing excess body weight and/or treating obesity (e.g. by control of appetite, feeding, food intake, calorie intake, and/or energy expenditure), including morbid obesity, as well as associated diseases, disorders and health conditions, including, but not limited to, obesity-linked inflammation, obesity-linked gallbladder disease and obesity-induced sleep apnea. Effects of the peptide conjugates of the invention on these conditions may be mediated in whole or in part via an effect on body weight, or may be independent thereof.

Further aspects of the invention will become apparent from the disclosure below.

DETAILED DESCRIPTION OF THE INVENTION

Figure 1A:
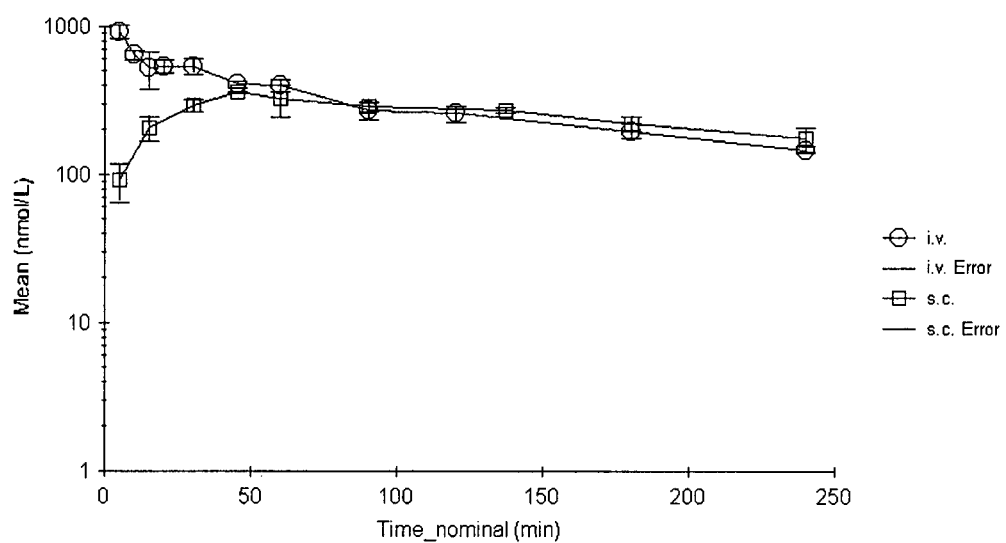
FIG. 1. Mean plasma concentration versus time (log-linear) after i.v. and s.c. administration of 100 nmol/kg to mice. A: Compound 33, B: Compound 1. Data represent mean±SD, n=3/datapoint.

As already indicated above, one aspect of the present invention relates to a peptide conjugate having the formula:

Exendin-4(1-39)-Peg3-Peg3-[Gln1,Leu15]Gastrin17, (1)

Exendin-4(1-39)-[Gln1,Leu15]Gastrin17, (2)

| | |
|---|---|
| Exendin-4(1-39)-K-[Gln1,Leu15]Gastrin17, | (3) |
| Exendin-4(1-39)-AAA-[Gln1,Leu15]Gastrin17, | (4) |
| Exendin-4(1-39)-SKK-[Gln1,Leu15]Gastrin17, | (5) |
| Exendin-4(1-39)-Peg3-SKK-[Gln1,Leu15]Gastrin17, | (6) |
| Exendin-4(1-39)-8Aoc-SKK-[Gln1,Leu15]Gastrin17, | (7) |
| Exendin-4(1-39)-DBF-SKK-[Gln1,Leu15]Gastrin17, | (8) |
| Exendin-4(1-39)-8Aoc-8Aoc-[Gln1,Leu15]Gastrin17, | (9) |
| Exendin-4(1-39)-[Leu4]Gastrin6, | (10) |
| Exendin-4(1-39)-K-[Leu4]Gastrin6, | (11) |
| Exendin-4(1-39)-AAA-[Leu4]Gastrin6, | (12) |
| Exendin-4(1-39)-SKK-[Leu4]Gastrin6, | (13) |
| Exendin-4(1-39)-Peg3-SKK-[Leu4]Gastrin6, | (14) |
| Exendin-4(1-39)-Peg3-Peg3-[Leu4]Gastrin6, | (15) |
| Exendin-4(1-39)-8Aoc-SKK-[Leu4]Gastrin6, | (16) |
| Exendin-4(1-39)-DBF-SKK-[Leu4]Gastrin6, | (17) |
| Exendin-4(1-39)-8Aoc-8Aoc-[Leu4]Gastrin6, | (18) |
| Exendin-4(1-28)-[Gln1,Leu15]Gastrin17, | (19) |
| Exendin-4(1-28)-K-[Gln1,Leu15]Gastrin17, | (20) |
| Exendin-4(1-28)-AAA-[Gln1,Leu15]Gastrin17, | (21) |
| Exendin-4(1-28)-SKK-[Gln1,Leu15]Gastrin17, | (22) |
| Exendin-4(1-28)-Peg3-SKK-[Gln1,Leu15]Gastrin17, | (23) |
| Exendin-4(1-28)-Peg3-Peg3-[Gln1,Leu15]Gastrin17, | (24) |
| Exendin-4(1-28)-8Aoc-SKK-[Gln1,Leu15]Gastrin17, | (25) |
| Exendin-4(1-28)-DBF-SKK-[Gln1,Leu15]Gastrin17, | (26) |
| Exendin-4(1-28)-8Aoc-8Aoc-[Gln1,Leu15]Gastrin17, | (27) |
| Exendin-4(1-28)-[Leu4]Gastrin6, | (28) |
| Exendin-4(1-28)-K-[Leu4]Gastrin6, | (29) |
| Exendin-4(1-28)-AAA-[Leu4]Gastrin6, | (30) |
| Exendin-4(1-28)-SKK-[Leu4]Gastrin6, | (31) |
| Exendin-4(1-28)-Peg3-SKK-[Leu4]Gastrin6, | (32) |
| Exendin-4(1-28)-Peg3-Peg3-[Leu4]Gastrin6, | (33) |
| Exendin-4(1-28)-8Aoc-SKK-[Leu4]Gastrin6, | (34) |
| Exendin-4(1-28)-DBF-SKK-[Leu4]Gastrin6, | (35) |
| Exendin-4(1-28)-8Aoc-8Aoc-[Leu4]Gastrin6, | (36) |
| GLP-1(7-36)-[Gln1,Leu15]Gastrin17, | (37) |
| GLP-1(7-36)-K-[Gln1,Leu15]Gastrin17, | (38) |
| GLP-1(7-36)-AAA-[Gln1,Leu15]Gastrin17, | (39) |
| GLP-1(7-36)-SKK-[Gln1,Leu15]Gastrin17, | (40) |
| GLP-1(7-36)-Peg3-SKK-[Gln1,Leu15]Gastrin17, | (41) |
| GLP-1(7-36)-Peg3-Peg3-[Gln1,Leu15]Gastrin17, | (42) |
| GLP-1(7-36)-8Aoc-SKK-[Gln1,Leu15]Gastrin17, | (43) |
| GLP-1(7-36)-DBF-SKK-[Gln1,Leu15]Gastrin17, | (44) |
| GLP-1(7-36)-8Aoc-8Aoc-[Gln1,Leu15]Gastrin17, | (45) |
| GLP-1(7-36)-[Leu4]Gastrin6, | (46) |
| GLP-1(7-36)-K-[Leu4]Gastrin6, | (47) |
| GLP-1(7-36)-AAA-[Leu4]Gastrin6, | (48) |
| GLP-1(7-36)-SKK-[Leu4]Gastrin6, | (49) |
| GLP-1(7-36)-Peg3-SKK-[Leu4]Gastrin6, | (50) |
| GLP-1(7-36)-Peg3-Peg3-[Leu4]Gastrin6, | (51) |
| GLP-1(7-36)-8Aoc-SKK-[Leu4]Gastrin6, | (52) |
| GLP-1(7-36)-DBF-SKK-[Leu4]Gastrin6 | (53) | or

| | |
|---|---|
| GLP-1(7-36)-8Aoc-8Aoc-[Leu4]Gastrin6, | (54) | wherein each of the Exendin-4(1-39), the Exendin-4(1-28) and the GLP-1(7-36) peptide moieties is covalently attached to the remaining part of the respective conjugate molecule via its C-terminal, and each of the [Gln1,Leu15]Gastrin17 and [Leu4]Gastrin6 peptide moieties is covalently attached to the remaining part of the respective conjugate molecule via its N-terminal;

or a pharmaceutically acceptable salt or solvate thereof.

In a further aspect, the present invention relates to a peptide conjugate having the formula:

| | |
|---|---|
| Exendin-4(1-28)-Peg3-Peg3-[Leu3]Gastrin5 | (55) |
| Exendin-4(1-28)-Peg3-Peg3-[Ala1,Leu4]Gastrin6 | (56) |
| Exendin-4(1-28)-Peg3-Peg3-[Ala2,Leu4]Gastrin6 | (57) |
| Exendin-4(1-27)-Peg3-Peg3-[Leu4]Gastrin6 | (58) |
| Exendin-4(1-28)-Peg3-Peg3-[Leu2]Gastrin4 | (59) |
| [Leu14]Exendin-4(1-28)-Peg3-Peg3-[Leu4]Gastrin6 | (60) |
| [Orn12]Exendin-4(1-28)-Peg3-Peg3-[Leu4]Gastrin6 | (61) |
| [Orn27]Exendin-4(1-28)-Peg3-Peg3-[Leu4]Gastrin6 | (62) |
| [Phe25]Exendin-4(1-28)-Peg3-Peg3-[Leu4]Gastrin6 | 63) |
| [Asp28]Exendin-4(1-28)-Peg3-Peg3-[Leu4]Gastrin6 | (64) |
| [Tyr13]Exendin-4(1-28)-Peg3-Peg3-[Leu4]Gastrin6 | (65) |
| [Orn20]Exendin-4(1-28)-Peg3-Peg3-[Leu4]Gastrin6 | (66) |
| Exendin-4(1-28)-Peg3-[Leu4]Gastrin6 | (67) |
| Exendin-4(1-28)-[Leu4]Gastrin6 | (68) |
| Exendin-4(1-27)-[Leu4]Gastrin11 | (69) |
| Exendin-4(1-27)-Peg3-[Leu4]Gastrin6 | (70) |

| | |
|---|---|
| Exendin-4(1-27)-Peg3-[Leu3]Gastrin5 | (71) |
| Exendin-4(1-26)-Peg3-[Leu3]Gastrin5 | (72) |
| Exendin-4(1-27)-Peg3-[Leu2]Gastrin4 | (73) |
| [Tyr13,Leu14]Exendin-4(1-27)-Peg3-Peg3-[Leu4]Gastrin6 | (74) |
| [Tyr13,Phe25]Exendin-4(1-27)-Peg3-Peg3-[Leu4]Gastrin6 | (75) |
| [Leu14,Phe25]Exendin-4(1-27)-Peg3-Peg3-[Leu4]Gastrin6 | (76) |
| [Tyr13,Leu14,Phe25]Exendin-4(1-27)-Peg3-Peg3-[Leu4]Gastrin6 | (77) |
| Side chain-cyclo([Lys12,Glu16]Exendin-4(1-28)-Peg3-Peg3-[Leu4]Gastrin6 | (78) |
| Side chain-cyclo([Glu16,Lys20]Exendin-4(1-28)-Peg3-Peg3-[Leu4]Gastrin6 | (79) |
| Side chain-cyclo([Lys20,Glu24]Exendin-4(1-28)-Peg3-Peg3-[Leu4]Gastrin6 | (80) |
| [Lys16]Exendin-4(1-28)-Peg3-Peg3-[Leu4]Gastrin6 | (81) |
| Exendin-4(1-28)-Peg3-K-Peg3-[Leu4]Gastrin6 | (82) |
| Exendin-4(1-28)-[Thr4]Gastrin6 | (83) |
| Exendin-4(1-28)-[Phe4]Gastrin6 | (84) |
| [Leu14]Exendin-4(1-28)-[Nle3,Leu4]Gastrin6 | (85) |
| [Leu14]Exendin-4(1-28)-[Nle4]Gastrin6 | (86) |
| [Leu14]Exendin-4(1-28)-[Leu4,[3-(3-Pyridyl)-Ala]6]Gastrin6 | (87) |
| [Glu9,Leu14,Phe25,Tyr13]Exendin-4(1-27)-Peg3-Peg3-[Leu4]Gastrin6 | (88) |
| [Leu14,Phe25,Tyr13]Exendin-4(1-27)-Peg3-Peg3-[Leu4,Phe3]Gastrin6 | (89) |
| [Glu9,Leu14,Phe25,Tyr13]Exendin-4(1-27)-Peg3-Peg3-[Leu4,Phe3]Gastrin6 | (90) |
| [Arg27,Leu14,Phe25,Tyr13]Exendin-4(1-27)-Peg3-[Leu4]Gastrin6 | (91) |
| [Arg12,27,Leu14,Lys16,Phe25,Tyr13]Exendin-4(1-27)-Peg3-[Leu4]Gastrin6 | (92) |
| [Arg12,27,Leu14,Lys20,Phe25,Tyr13]Exendin-4(1-27)-Peg3-[Leu4]Gastrin6 | (93) |
| [Arg12,27,Leu14,Lys24,Phe25,Tyr13]Exendin-4(1-27)-Peg3-[Leu4]Gastrin6 | (94) |
| [Arg12,Leu14,Phe25,Tyr13]Exendin-4(1-27)-Peg3-[Leu4]Gastrin6 | (95) |
| [Glu9,Leu14,Phe25,Tyr13]Exendin-4(1-27)-[Leu2]Gastrin4 | (96) |
| [Glu9,Leu14,Phe25,Tyr13]Exendin-4(1-27)-Peg3-[Leu2]Gastrin4 | (97) |
| [Glu9,Leu14,Phe25,Tyr13]Exendin-4(1-27)-Orn-Peg3-[Leu2]Gastrin4 | (98) |
| [Glu9,Leu14,Phe25,Tyr13]Exendin-4(1-27)-Peg3-Orn-[Leu2]Gastrin4 | (99) |
| [Glu9,Leu14,Phe25,Tyr13]Exendin-4(1-27)-Orn-Orn-[Leu2]Gastrin4 | (100) |
| [Glu9,Leu14,Phe25,Tyr13]Exendin-4(1-27)-[Leu4]Gastrin6 | (101) |
| [Glu9,Leu14,Phe25,Tyr13]Exendin-4(1-27)-Peg3-[Leu4]Gastrin6 | (102) |
| [Glu9,Leu14,Phe25,Tyr13]Exendin-4(1-27)-Orn-Peg3-[Leu4]Gastrin6 | (103) |
| [Glu9,Leu14,Phe25,Tyr13]Exendin-4(1-27)-Peg3-Orn-[Leu4]Gastrin6 | (104) |
| [Glu9,Leu14,Phe25,Tyr13]Exendin-4(1-27)-Orn-Orn-[Leu4]Gastrin6 | (105) |
| [Lys(Hexadecanoyl-isoGlu)34]GLP-1(7-37)-Peg3-Peg3-[Leu4]Gastrin6 | (106) |
| [Arg34,Lys(Hexadecanoyl-isoGlu)26]GLP-1(7-37)-Peg3-Peg3-[Leu4]Gastrin6 | (107) |
| [Arg26,34,Lys(Hexadecanoyl-isoGlu)36]GLP-1(7-37)-Peg3-Peg3-[Leu4]Gastrin6 | (108) |
| [Lys(Hexadecanoyl-isoGlu)26]GLP-1(7-37)-Peg3-Peg3-[Leu4]Gastrin6 | (109) |
| [Arg26,34,Gly8,Lys(Hexadecanoyl-isoGlu)36]GLP-1(7-37)-Peg3-Peg3-[Leu4]Gastrin6 | (110) |
| [Aib8,Arg34,Lys(Hexadecanoyl-isoGlu)26]GLP-1(7-37)-Peg3-Peg3-[Leu4]Gastrin6 | (111) |
| [Aib8,Arg34]GLP-1(7-37)-Peg3-Peg3-[Leu4]Gastrin6 | (112) |
| [Arg34]GLP-1(7-37)-Peg3-Peg3-[Leu4]Gastrin6 | (113) | or a pharmaceutically acceptable salt or solvate thereof.

The above formulae for the peptide conjugates of the invention, which are written employing conventional and widely used abbreviations/designations for the various peptide moieties in question [i.e. Exendin-4(1-39), Exendin-4(1-28) and GLP-1(7-36)] may be written in conventional full amino acid sequence form as follows (with linker moieties highlighted in bold font):

```
                                               (SEQ ID NO: 1)
H-HGEGTFTSDLSKQMEEEAVRLFIEWLKNGGPSSGAPPPS-Peg3-

Peg3-QGPWLEEEEEAYGWLDF-NH2
```

```
                                               (SEQ ID NO: 2)
H-HGEGTFTSDLSKQMEEEAVRLFIEWLKNGGPSSGAPPPSQGPWLEEEE

EAYGWLDF-NH2 (no linker)
```

```
                                               (SEQ ID NO: 3)
H-HGEGTFTSDLSKQMEEEAVRLFIEWLKNGGPSSGAPPPS-K-

QGPWLEEEEEAYGWLDF-NH2
```

```
                                               (SEQ ID NO: 4)
H-HGEGTFTSDLSKQMEEEAVRLFIEWLKNGGPSSGAPPPS-AAA-

QGPWLEEEEEAYGWLDF-NH2
```

-continued

```
                                              (SEQ ID NO: 5)
H-HGEGTFTSDLSKQMEEEAVRLFIEWLKNGGPSSGAPPPS-SKK-
QGPWLEEEEEAYGWLDF-NH₂

(SEQ ID NO: 6)
H-HGEGTFTSDLSKQMEEEAVRLFIEWLKNGGPSSGAPPPS-Peg3-
SKK-QGPWLEEEEEAYGWLDF-NH₂

(SEQ ID NO: 7)
H-HGEGTFTSDLSKQMEEEAVRLFIEWLKNGGPSSGAPPPS-8Aoc-
SKK-QGPWLEEEEEAYGWLDF-NH₂

(SEQ ID NO: 8)
H-HGEGTFTSDLSKQMEEEAVRLFIEWLKNGGPSSGAPPPS-DBF-SKK-
QGPWLEEEEEAYGWLDF-NH₂

(SEQ ID NO: 9)
H-HGEGTFTSDLSKQMEEEAVRLFIEWLKNGGPSSGAPPPS-8Aoc-
8Aoc-QGPWLEEEEEAYGWLDF-NH₂

(SEQ ID NO: 10)
H-HGEGTFTSDLSKQMEEEAVRLFIEWLKNGGPSSGAPPPSYGWLDF-
NH₂ (no linker)

(SEQ ID NO: 11)
H-HGEGTFTSDLSKQMEEEAVRLFIEWLKNGGPSSGAPPPS-K-
YGWLDF-NH₂

(SEQ ID NO: 12)
H-HGEGTFTSDLSKQMEEEAVRLFIEWLKNGGPSSGAPPPS-AAA-
YGWLDF-NH₂

(SEQ ID NO: 13)
H-HGEGTFTSDLSKQMEEEAVRLFIEWLKNGGPSSGAPPPS-SKK-
YGWLDF-NH₂

(SEQ ID NO: 14)
H-HGEGTFTSDLSKQMEEEAVRLFIEWLKNGGPSSGAPPPS-Peg3-
SKK-YGWLDF-NH₂

(SEQ ID NO: 15)
H-HGEGTFTSDLSKQMEEEAVRLFIEWLKNGGPSSGAPPPS-Peg3-
Peg3-YGWLDF-NH₂

(SEQ ID NO: 16)
H-HGEGTFTSDLSKQMEEEAVRLFIEWLKNGGPSSGAPPPS-8Aoc-
SKK-YGWLDF-NH₂

(SEQ ID NO: 17)
H-HGEGTFTSDLSKQMEEEAVRLFIEWLKNGGPSSGAPPPS-DBF-
SKK-YGWLDF-NH₂

(SEQ ID NO: 18)
H-HGEGTFTSDLSKQMEEEAVRLFIEWLKNGGPSSGAPPPS-8Aoc-
8Aoc-YGWLDF-NH₂

(SEQ ID NO: 19)
H-HGEGTFTSDLSKQMEEEAVRLFIEWLKNQGPWLEEEEEAYGWLDF-
NH₂ (no linker)

(SEQ ID NO: 20)
H-HGEGTFTSDLSKQMEEEAVRLFIEWLKN-K-QGPWLEEEEEAYGWLD
F-NH₂

(SEQ ID NO: 21)
H-HGEGTFTSDLSKQMEEEAVRLFIEWLKN-AAA-QGPWLEEEEEAYGWL
DF-NH₂

(SEQ ID NO: 22)
H-HGEGTFTSDLSKQMEEEAVRLFIEWLKN-SKK-QGPWLEEEEEAYGWL
DF-NH₂

(SEQ ID NO: 23)
H-HGEGTFTSDLSKQMEEEAVRLFIEWLKN-Peg3-SKK-
QGPWLEEEEEAYGWLDF-NH₂

(SEQ ID NO: 24)
H-HGEGTFTSDLSKQMEEEAVRLFIEWLKN-Peg3-Peg3-
QGPWLEEEEEAYGWLDF-NH₂

(SEQ ID NO: 25)
H-HGEGTFTSDLSKQMEEEAVRLFIEWLKN-8Aoc-SKK-
QGPWLEEEEEAYGWLDF-NH₂

(SEQ ID NO: 26)
H-HGEGTFTSDLSKQMEEEAVRLFIEWLKN-DBF-SKK-QGPWLEEEEEA
YGWLDF-NH₂

(SEQ ID NO: 27)
H-HGEGTFTSDLSKQMEEEAVRLFIEWLKN-8Aoc-8Aoc-
QGPWLEEEEEAYGWLDF-NH₂

(SEQ ID NO: 28)
H-HGEGTFTSDLSKQMEEEAVRLFIEWLKN-YGWLDF-NH₂ (no
linker)

(SEQ ID NO: 29)
H-HGEGTFTSDLSKQMEEEAVRLFIEWLKN-K-YGWLDF-NH₂

(SEQ ID NO: 30)
H-HGEGTFTSDLSKQMEEEAVRLFIEWLKN-AAA-YGWLDF-NH₂

(SEQ ID NO: 31)
H-HGEGTFTSDLSKQMEEEAVRLFIEWLKN-SKK-YGWLDF-NH₂

(SEQ ID NO: 32)
H-HGEGTFTSDLSKQMEEEAVRLFIEWLKN-Peg3-SKK-YGWLDF-NH₂

(SEQ ID NO: 33)
H-HGEGTFTSDLSKQMEEEAVRLFIEWLKN-Peg3-Peg3-YGWLDF-
NH₂

(SEQ ID NO: 34)
H-HGEGTFTSDLSKQMEEEAVRLFIEWLKN-8Aoc-SKK-YGWLDF-NH₂

(SEQ ID NO: 35)
H-HGEGTFTSDLSKQMEEEAVRLFIEWLKN-DBF-SKK-YGWLDF-NH₂

(SEQ ID NO: 36)
H-HGEGTFTSDLSKQMEEEAVRLFIEWLKN-8Aoc-8Aoc-YGWLDF-
NH₂

(SEQ ID NO: 37)
H-HAEGTFTSDVSSYLEGQAAKEFIAWLVKGRQGPWLEEEEEAYGWLDF-
NH₂ (no linker)

(SEQ ID NO: 38)
H-HAEGTFTSDVSSYLEGQAAKEFIAWLVKGR-K-QGPWLEEEEEAYGWL
DF-NH₂
```

-continued (SEQ ID NO: 39)
H-HAEGTFTSDVSSYLEGQAAKEFIAWLVKGR-AAA-QGPWLEEEEAYGWLDF-NH$_2$ (SEQ ID NO: 40)
H-HAEGTFTSDVSSYLEGQAAKEFIAWLVKGR-SKK-QGPWLEEEEAYGWLDF-NH$_2$ (SEQ ID NO: 41)
H-HAEGTFTSDVSSYLEGQAAKEFIAWLVKGR-Peg3-SKK-QGPWLEEEEAYGWLDF-NH$_2$ (SEQ ID NO: 42)
H-HAEGTFTSDVSSYLEGQAAKEFIAWLVKGR-Peg3-Peg3-QGPWLEEEEAYGWLDF-NH$_2$ (SEQ ID NO: 43)
H-HAEGTFTSDVSSYLEGQAAKEFIAWLVKGR-8Aoc-SKK-QGPWLEEEEAYGWLDF-NH$_2$ (SEQ ID NO: 44)
H-HAEGTFTSDVSSYLEGQAAKEFIAWLVKGR-DBF-SKK-QGPWLEEEEAYGWLDF-NH$_2$ (SEQ ID NO: 45)
H-HAEGTFTSDVSSYLEGQAAKEFIAWLVKGR-8Aoc-8Aoc-QGPWLEEEEAYGWLDF-NH$_2$ (SEQ ID NO: 46)
H-HAEGTFTSDVSSYLEGQAAKEFIAWLVKGRYGWLDF-NH2 (no linker)

(SEQ ID NO: 47)
H-HAEGTFTSDVSSYLEGQAAKEFIAWLVKGR-K-YGWLDF-NH$_2$ (SEQ ID NO: 48)
H-HAEGTFTSDVSSYLEGQAAKEFIAWLVKGR-AAA-YGWLDF-NH$_2$ (SEQ ID NO: 49)
H-HAEGTFTSDVSSYLEGQAAKEFIAWLVKGR-SKK-YGWLDF-NH$_2$ (SEQ ID NO: 50)
H-HAEGTFTSDVSSYLEGQAAKEFIAWLVKGR-Peg3-SKK-YGWLDF-NH$_2$ (SEQ ID NO: 51)
H-HAEGTFTSDVSSYLEGQAAKEFIAWLVKGR-Peg3-Peg3-YGWLDF-NH$_2$ (SEQ ID NO: 52)
H-HAEGTFTSDVSSYLEGQAAKEFIAWLVKGR-8Aoc-SKK-YGWLDF-NH$_2$ (SEQ ID NO: 53)
H-HAEGTFTSDVSSYLEGQAAKEFIAWLVKGR-DBF-SKK-YGWLDF-NH$_2$ (SEQ ID NO: 54)
H-HAEGTFTSDVSSYLEGQAAKEFIAWLVKGR-8Aoc-8Aoc-YGWLDF-NH$_2$ (SEQ ID NO: 55)
H-HGEGTFTSDLSKQMEEEAVRLFIEWLKN-Peg3-Peg3-GWLDF-NH2

(SEQ ID NO: 56)
H-HGEGTFTSDLSKQMEEEAVRLFIEWLKN-Peg3-Peg3-AGWLDF-NH2

(SEQ ID NO: 57)
H-HGEGTFTSDLSKQMEEEAVRLFI EWLKN-Peg3-Peg3-YAWLDF-NH2

(SEQ ID NO: 58)
H-HGEGTFTSDLSKQMEEEAVRLFIEWLK-Peg3-Peg3-YGWLDF-NH2

(SEQ ID NO: 59)
H-HGEGTFTSDLSKQMEEEAVRLFIEWLKN-Peg3-Peg3-WLDF-NH2

(SEQ ID NO: 60)
H-HGEGTFTSDLSKQLEEEAVRLFIEWLKN-Peg3-Peg3-YGWLDF-NH2

(SEQ ID NO: 61)
H-HGEGTFTSDLS-Orn-QMEEEAVRLFIEWLKN-Peg3-Peg3-YGWLDF-NH2

(SEQ ID NO: 62)
H-HGEGTFTSDLSKQMEEEAVRLFIEWL-Orn-N-Peg3-Peg3-YGWLDF-NH2

(SEQ ID NO: 63)
H-HGEGTFTSDLSKQMEEEAVRLFIEFLKN-Peg3-Peg3-YGWLDF-NH2

(SEQ ID NO: 64)
H-HGEGTFTSDLSKQMEEEAVRLFIEWLKD-Peg3-Peg3-YGWLDF-NH2

(SEQ ID NO: 65)
H-HGEGTFTSDLSKYMEEEAVRLFIEWLKN-Peg3-Peg3-YGWLDF-NH2

(SEQ ID NO: 66)
H-HGEGTFTSDLSKQMEEEAV-Orn-LFIEWLKN-Peg3-Peg3-YGWLDF-NH2

(SEQ ID NO: 67)
H-HGEGTFTSDLSKQMEEEAVRLFIEWLKN-Peg3-YGWLDF-NH2

(SEQ ID NO: 68)
H-HGEGTFTSDLSKQMEEEAVRLFIEWLKNYGWLDF-NH2

(SEQ ID NO: 69)
H-HGEGTFTSDLSKQMEEEAVRLFIEWLKEEEEAYGWLDF-NH2

(SEQ ID NO: 70)
H-HGEGTFTSDLSKQMEEEAVRLFIEWLK-Peg3-YGWLDF-NH2

(SEQ ID NO: 71)
H-HGEGTFTSDLSKQMEEEAVRLFIEWLK-Peg3-GWLDF-NH2

(SEQ ID NO: 72)
H-HGEGTFTSDLSKQMEEEAVRLFIEWL-Peg3-GWLDF-NH2

(SEQ ID NO: 73)
H-HGEGTFTSDLSKQMEEEAVRLFIEWLK-Peg3-WLDF-NH2

(SEQ ID NO: 74)
H-HGEGTFTSDLSKYLEEEAVRLFIEWLK-Peg3-Peg3-YGWLDF-NH2

(SEQ ID NO: 75)
H-HGEGTFTSDLSKYMEEEAVRLFIEFLK-Peg3-Peg3-YGWLDF-NH2

(SEQ ID NO: 76)
H-HGEGTFTSDLSKQLEEEAVRLFIEFLK-Peg3-Peg3-YGWLDF-NH2

(SEQ ID NO: 77)
H-HGEGTFTSDLSKYLEEEAVRLFIEFLK-Peg3-Peg3-YGWLDF-NH2

```
(SEQ ID NO: 78)
H-HGEGTFTSDLS-KQ-QME-EQ-EAVRLFIEWLKN-Peg3-Peg3-
YGWLDF-NH2

(SEQ ID NO: 79)
H-HGEGTFTSDLSKQME-EQ-EAV-KQ-LFIEWLKN-Peg3-Peg3-
YGWLDF-NH2

(SEQ ID NO: 80)
H-HGEGTFTSDLSKQMEEEAV-KQ-LFI-EQ-WLKN-Peg3-Peg3-
YGWLDF-NH2

(SEQ ID NO: 81)
H-HGEGTFTSDLSKQMEKEAVRLFIEWLKN-Peg3-Peg3-YGWLDF-
NH2

(SEQ ID NO: 82)
H-HGEGTFTSDLSKQMEEEAVRLFIEWLKN-Peg3-K-Peg3-YGWLDF-
NH2

(SEQ ID NO: 83)
H-HGEGTFTSDLSKQMEEEAVRLFIEWLKNYGWTDF-NH2

(SEQ ID NO: 84)
H-HGEGTFTSDLSKQMEEEAVRLFIEWLKNYGWFDF-NH2

(SEQ ID NO: 85)
H-HGEGTFTSDLSKQLEEEAVRLFIEWLKNYG-1Nal-LDF-NH2

(SEQ ID NO: 86)
H-HGEGTFTSDLSKQLEEEAVRLFIEWLKNYGW-Nle-DF-NH2

(SEQ ID NO: 87)
H-HGEGTFTSDLSKQLEEEAVRLFIEWLKNYGWLD[3-(3-Pyridyl)-
alanyl]-NH2

(SEQ ID NO: 88)
H-HGEGTFTSELSKYLEEEAVRLFIEFLK-Peg3-Peg3-YGWLDF-NH2

(SEQ ID NO: 89)
H-HGEGTFTSDLSKYLEEEAVRLFIEFLK-Peg3-Peg3-YGFLDF-NH2

(SEQ ID NO: 90)
H-HGEGTFTSELSKYLEEEAVRLFIEFLK-Peg3-Peg3-YGFLDF-NH2

(SEQ ID NO: 91)
H-HGEGTFTSDLSKYLEEEAVRLFIEFLR-Peg3-YGWLDF-NH2

(SEQ ID NO: 92)
H-HGEGTFTSDLSRYLEKEAVRLFIEFLR-Peg3-YGWLDF-NH2

(SEQ ID NO: 93)
H-HGEGTFTSDLSRYLEEEAVKLFIEFLR-Peg3-YGWLDF-NH2

(SEQ ID NO: 94)
H-HGEGTFTSDLSRYLEEEAVRLFIKFLR-Peg3-YGWLDF-NH2

(SEQ ID NO: 95)
H-HGEGTFTSDLSRYLEEEAVRLFIEFLK-Peg3-YGWLDF-NH2

(SEQ ID NO: 96)
H-HGEGTFTSELSKYLEEEAVRLFIEFLKWLDF-NH2

(SEQ ID NO: 97)
H-HGEGTFTSELSKYLEEEAVRLFIEFLK-Peg3-WLDF-NH2

(SEQ ID NO: 98)
H-HGEGTFTSELSKYLEEEAVRLFIEFLK-Orn-Peg3-WLDF-NH2

(SEQ ID NO: 99)
H-HGEGTFTSELSKYLEEEAVRLFIEFLK-Peg3-Orn-WLDF-NH2

(SEQ ID NO: 100)
H-HGEGTFTSELSKYLEEEAVRLFIEFLK-Orn-Orn-WLDF-NH2

(SEQ ID NO: 101)
H-HGEGTFTSELSKYLEEEAVRLFIEFLKYGWLDF-NH2

(SEQ ID NO: 102)
H-HGEGTFTSELSKYLEEEAVRLFIEFLK-Peg3-YGWLDF-NH2

(SEQ ID NO: 103)
H-HGEGTFTSELSKYLEEEAVRLFIEFLK-Orn-Peg3-YGWLDF-NH2

(SEQ ID NO: 104)
H-HGEGTFTSELSKYLEEEAVRLFIEFLK-Peg3-Orn-YGWLDF-NH2

(SEQ ID NO: 105)
H-HGEGTFTSELSKYLEEEAVRLFIEFLK-Orn-Orn-YGWLDF-NH2

(SEQ ID NO: 106)
H-HAEGTFTSDVSSYLEGQAAKEFIAWLV-K(Hexadecanoyl-
isoGlu)-GRG-Peg3-Peg3-YGWLDF-NH2

(SEQ ID NO: 107)
H-HAEGTFTSDVSSYLEGQAA-K(Hexadecanoyl-isoGlu)-
EFIAWLVRGRG-Peg3-Peg3-YGWLDF-NH2

(SEQ ID NO: 108)
H-HAEGTFTSDVSSYLEGQAAREFIAWLVRG-K(Hexadecanoyl-
isoGlu)-G-Peg3-Peg3-YGWLDF-NH2

(SEQ ID NO: 109)
H-HAEGTFTSDVSSYLEGQAA-K(Hexadecanoyl-isoGlu)-
EFIAWLVKGRG-Peg3-Peg3-YGWLDF-NH2

(SEQ ID NO: 110)
H-HGEGTFTSDVSSYLEGQAAREFIAWLVRG-K(Hexadecanoyl-
isoGlu)-G-Peg3-Peg3-YGWLDF-NH2

(SEQ ID NO: 111)
H-H-Aib-EGTFTSDVSSYLEGQAA-K(Hexadecanoyl-isoGlu)-
EFIAWLVRGRG-Peg3-Peg3-YGWLDF-NH2

(SEQ ID NO: 112)
H-H-Aib-EGTFTSDVSSYLEGQAAKEFIAWLVRGRG-Peg3-Peg3-
YGWLDF-NH2

(SEQ ID NO: 113)
H-HAEGTFTSDVSSYLEGQAAKEFIAWLVRGRG-Peg3-Peg3-
YGWLDF-NH2
``` wherein the abbreviations Peg3, 8Aoc, DBF, 1NaI, bAla, Orn, DPR, Dbu, Gaba and Aib represent the following non-naturally occurring amino acid moieties:

Peg3: —NH—CH$_2$—CH$_2$—O—CH$_2$—CH$_2$—O—CH$_2$—C(O)— (derived from 8-amino-3,6-dioxaoctanoic acid);

8Aoc: —NH—CH$_2$—CH$_2$—CH$_2$—CH$_2$—CH$_2$—CH$_2$—CH$_2$—C(O)— (derived from 8-aminooctanoic acid)I;

DBF:

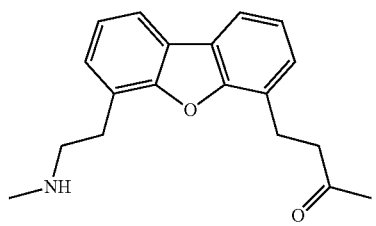 [SMILES: CNCCc1cccc2c1oc1c(CCC(C)=O)cccc12]

[derived from 4-(2-aminoethyl)-6-dibenzofuranpropanoic acid];
1 Nal: 1-napthylalanine
bAla: beta-alanine
Gaba: γ-aminobutanoic acid
Aib: α-Amino-isobutanoic acid
Dbu: Diaminobutanoic acid
DPR: Diaminopropionic acid
Orn: Ornitine Thus, with regard to the orientation of the linker moiety in a peptide conjugate of the invention, the linker moiety -Peg3-Peg3-, for example, designates the chemical moiety

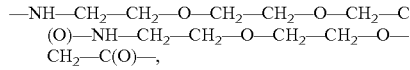

the —NH— . . . moiety to the left of the linker moiety in question being covalently attached to the Exendin-4- or GLP-1-derived moiety of the peptide conjugate in question, and the . . . —C(O)— moiety to the right of the linker moiety in question being attached to the Gastrin-derived moiety of the peptide conjugate in question.

With regard to the remaining specified linker moieties, -K- designates a lysine amino acid residue, -AAA- designates a -Ala-Ala-Ala- tripeptide residue and -SKK- designates a -Ser-Lys-Lys- tripeptide residue.

In some of the peptide conjugates of the invention, listed above, it is to be understood that the GLP-1(7-36) peptide sequence moiety is derived from the sequence of human GLP-1 (hGLP-1) sequence or is an analogue thereof.

In some other of the peptide conjugates of the invention, listed above, it is to be understood that the Exendin-4(1-39) peptide sequence moiety is derived from the sequence of the *Heloderma suspectum* Exendin-4 sequence or is an analogue thereof.

Likewise, the [Gln1,Leu15]Gastrin17 and [Leu4]Gastrin6 moieties in the conjugates are derived from human Gastrin.

It is to be understood that SEQ ID NO: 1 equals Compound 1, SEQ ID NO: 2 equals Compound 2 etc.

It is to be understood that each one of the above peptide conjugates 1-54 individually, i.e. compound 1 or compound 2 or compound 3 . . . (etc., up to compound 54), and each one of the further peptide conjugates 55-113 disclosed below (See Table 2 and 3 in Example 2), individually, i.e. compound 55 or compound 56 . . . (etc. up to compound 113), or a pharmaceutically acceptable salt or solvate thereof, constitutes a further, individual aspect of the present invention.

In the context of the present invention, unless amino acids are referred to by their full name (e.g. alanine, arginine, etc.), they are designated by their conventional three-letter and/or single-letter abbreviations (e.g. Ala or A for alanine, Arg or R for arginine, etc.).

The term "peptide conjugate" in the context of the present invention refers to a molecule in which a first peptide moiety is attached (i.e. coupled or linked), either directly or via a linking (i.e. bridging or spacing) chemical moiety, by means of covalent chemical bonding to a second peptide moiety.

Compounds of the invention may carry one or more intramolecular lactam bridges within the peptide sequence. Each such bridge in compounds listed in Table 2 (referred to by the prefix "side-chain-cyclo") is formed between a side chain containing a carboxylic acid and another side chain containing an amine. The two amino acid residues are typically separated by three amino acids in the linear sequence.

In peptide conjugates of the invention, exendin-4 or $Z_a$ may have at least 75% identity to native exendin-4, eg. at least 80, 85, 90 or 95%.

In the peptide conjugates of the invention, gastrin or $Y_a$ may have at least 70% identity to native gastrin, eg. at least 75, 80, 85, 90 or 95%. In the peptide conjugates of the invention, GLP-1 or $X_a$ may have at least 85% identity to native GLP-1, eg. at least 90 or 95%.

In an embodiment, the polypeptide of the invention may comprise the amino acid sequence set forth in any one of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112 and 113 or a functional fragment/variant thereof that is at least about 80%, 85%, 90%, 95%, 97%, 98%, 99%, 99.5% identical to one or more of the recited sequences, or functional fragments/variants thereof that have at most 20, 15, 10, 9, 8, 7, 6, 5, 4, 3, 2, or 1 amino acid substitutions compared to one or more of the recited sequences, with or without the signal sequence, with or without substitution of one or more cysteine residues with another residue, such as a serine, and contiguous segments thereof of at least 2 amino acids in length.

In an embodiment, the polypeptide of the invention (i) shares at least 99% amino acid sequence identity to any one of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112 and 113, or to a portion thereof; or (ii) comprises at least 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 contiguous amino acids of any one of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112 and 113; or (iii) both.

The term "pharmaceutically acceptable salt" in the context of the present invention (pharmaceutically acceptable salt of a peptide conjugate of the invention) is intended to indicate a salt which is not harmful to a patient or subject to which the salt in question is administered. It may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type $N(R^1)$ $(R^2)(R^3)$ $(R^4)^+$, where $R^1$, $R^2$, $R^3$ and $R^4$ independently will typically designate hydrogen, optionally substituted $C_{1-6}$-alkyl or optionally substituted $C_{2-6}$-alkenyl. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", $3^{rd}$ edition, James Swarbrick (Ed.), Informa Healthcare USA (Inc.), NY, USA, 2007, and in *J. Pharm. Sci.* 66: 2 (1977).

The term "solvate" in the context of the present invention refers to a complex of defined stoichiometry formed between a solute (in casu, a peptide conjugate or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Another aspect of the present invention relates to a peptide conjugate or pharmaceutically acceptable salt thereof according to the invention, for use as a medicament. In a further aspect, the medicament in question is a medicament for use in the treatment, in a subject in need thereof, of one or more of the following diseases or disorders and associated conditions:

type 1 diabetes, type 2 diabetes, pre-diabetes, Insulin resistance syndrome, impaired glucose tolerance (IGT), disease states associated with elevated blood glucose levels, hyperglycemia, hypertension, atherogenic dyslipidemia, arteriosclerosis (e.g. atherosclerosis), coronary heart disease, peripheral artery disease, stroke, microvascular disease, gastric disease, metabolic syndrome, cancer (e.g. colon cancer), inflammatory bowel disease (IBD) and irritable bowel syndrome (IBS).

Further diseases or disorders of possible relevance in this connection include obesity, morbid obesity, obesity-linked inflammation, obesity-linked gall bladder disease and obesity-induced sleep apnea.

In a still further aspect, the medicament in question is a medicament for use in inducing, in a subject in need thereof, pancreatic islet neogenesis (e.g. for promoting formation of new β-cells in the islets of the pancreas).

In a still further aspect, the medicament in question is a medicament for use in inducing, in a subject in need thereof, survival of β-cells in the pancreatic islets (e.g. for preventing loss of β-cells in the pancreatic islets).

In yet another aspect, the medicament in question is a medicament for use in preventing, in a subject in need thereof, β-cell apoptosis in the pancreatic islets (e.g. for preventing loss of β-cells in the pancreatic islets).

In a further aspect, the medicament in question is a medicament for use in reducing, in a subject in need thereof, haemoglobin b1Ac (glycosylated haemoglobin; HbA1c) levels in the blood.

A further aspect of the invention relates to the use of a peptide conjugate of the invention in the manufacture of a medicament for the treatment, in a subject in need thereof, of one or more of the following conditions, diseases or disorders:

type 1 diabetes, type 2 diabetes, pre-diabetes, Insulin resistance syndrome, impaired glucose tolerance (IGT), disease states associated with elevated blood glucose levels, hyperglycemia, hypertension, atherogenic dyslipidemia, arteriosclerosis (e.g. atherosclerosis), coronary heart disease, peripheral artery disease, stroke, microvascular disease, gastric disease, metabolic syndrome, cancer (e.g. colon cancer), inflammatory bowel disease (IBD) and irritable bowel syndrome (IBS).

A peptide conjugate of the invention may further be used in:
the manufacture of a medicament for inducing pancreatic islet neogenesis in a subject in need thereof;
the manufacture of a medicament for preventing β-cell apoptosis in the pancreatic islets in a subject in need thereof; or
the manufacture of a medicament for reducing haemoglobin b1Ac (glycosylated haemoglobin; HbA1c) levels in the blood of a subject in need thereof.

Among related, additional aspects of the invention are corresponding methods of treatment of conditions, diseases or disorders among those mentioned above. Thus, one such additional aspect of the invention relates to a method for treatment, in a subject in need thereof, of one or more of the following diseases or disorders:

type 1 diabetes, type 2 diabetes, pre-diabetes, Insulin resistance syndrome, impaired glucose tolerance (IGT), disease states associated with elevated blood glucose levels, hyperglycemia, hypertension, atherogenic dyslipidemia, arteriosclerosis (e.g. atherosclerosis), coronary heart disease, peripheral artery disease, stroke, microvascular disease, gastric disease, metabolic syndrome, cancer (e.g. colon cancer), inflammatory bowel disease (IBD) and irritable bowel syndrome (IBS), the method comprising administering to the subject a therapeutically effective amount of a peptide conjugate or pharmaceutically acceptable salt or solvate thereof according to the invention.

Again, further conditions, diseases or disorders of possible relevance in the context of methods of treatment according to the invention include obesity, morbid obesity, obesity-linked inflammation, obesity-linked gall bladder disease and obesity-induced sleep apnea.

A further aspect of the present invention relates to a method for inducing pancreatic islet neogenesis in a subject in need thereof, the method comprising administering to the subject a therapeutically effective amount of a peptide conjugate or pharmaceutically acceptable salt or solvate thereof according to the invention.

An additional aspect of the invention relates to a method for promoting β-cell survival in the pancreatic islets in a subject in need thereof, the method comprising administering to the subject a therapeutically effective amount of a peptide conjugate or pharmaceutically acceptable salt or solvate thereof according to the invention.

An additional aspect of the invention relates to a method for reducing or preventing β-cell apoptosis in the pancreatic islets in a subject in need thereof, the method comprising administering to the subject a therapeutically effective amount of a peptide conjugate or pharmaceutically acceptable salt or solvate thereof according to the invention.

Another aspect of the invention relates to a method for reducing haemoglobin b1Ac (glycosylated haemoglobin; HbA1c) levels in the blood of a subject in need thereof, the method comprising administering to the subject a therapeutically effective amount of a peptide conjugate or pharmaceutically acceptable salt or solvate thereof according to the invention.

Still further aspects of the present invention relate to the following:

A method of treatment, in a subject in need thereof, of a disease state associated with elevated blood glucose levels;

A method for lowering blood glucose levels in a subject in need thereof;

A method of stimulating Insulin release in a subject in need thereof;

A method for regulating gastric emptying in a subject in need thereof; and

A method for lowering plasma lipid levels in a subject in need thereof.

In each of the latter methods of the invention, the method comprises administering to the subject a therapeutically effective amount of a peptide conjugate or pharmaceutically acceptable salt or solvate thereof according to the invention.

The term "therapeutically effective amount" as employed in the context of the above-described methods of treatment or other therapeutic intervention according to the invention refers to an amount that is sufficient to cure, ameliorate, alleviate or partially arrest the clinical manifestations of the particular disease, disorder or condition that is the object of the treatment or other therapeutic intervention in question. An amount adequate to accomplish this is defined as a therapeutically effective amount. The administered amount and the method of administration can be tailored to achieve optimal efficacy. An amount effective for a given purpose will depend, inter alia, on the severity of the disease, disorder or condition that is the object of the particular treatment or other therapeutic intervention, on the body weight and general condition of the subject in question, on diet, on possible concurrent medication, and on other factors well known to those skilled in the medical arts. Determination of an appropriate dosage size and dosing regimen most appropriate for administration of a peptide conjugate or pharmaceutically acceptable salt or solvate thereof according to the invention to a human may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are well known to the skilled person.

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e. not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. "Treatment" in some embodiments may be an intervention performed with the intention of preventing the development of, or altering the pathology of, a condition, disease or disorder. Accordingly, "treatment" may refer both to therapeutic intervention or to prophylactic or preventive measures. A subject (e.g. a human) in need of treatment may thus be a subject already suffering from the disease or disorder in question, or a subject in which the disorder is to be prevented. The term "treatment" thus includes inhibition or reduction of an increase in severity of a pathological state or symptoms (e.g. weight gain or hyperglycemia) relative to the absence of treatment, and is not necessarily meant to imply complete cessation of the relevant disease, disorder or condition.

The term "agonist" as employed in the context of the invention refers to a substance (ligand) that activates the receptor type in question.

The term "GLP-1 receptor agonist" as employed in the context of the invention (sometimes termed elsewhere "GLP-1 agonist") refers to a substance (ligand) that activates a GLP-1 receptor, such as the human GLP-1 receptor. Substances that activate the human GLP-1 receptor include the native GLP-1 peptide hormones GLP-1(7-37), GLP-1(7-36) amide, oxyntomodulin, exendin-3, exendin-4, glucagon, gastric inhibitory polypeptide (GIP), and functional peptide analogues and derivatives thereof.

The term "antagonist" as employed in the context of the invention refers to a substance (ligand) that blocks, neutralizes or counteracts the effect of another substance (ligand) that functions as an agonist towards the receptor type in question.

In the context of the invention, a subject in need of the particular treatment or other therapeutic intervention referred to in connection with the various aspects of the invention described above is preferably a mammal, and more particularly, is a human.

An additional aspect of the invention relates to a pharmaceutical composition comprising a peptide conjugate, or pharmaceutically acceptable salt or solvate thereof, according to the invention, together with a pharmaceutically acceptable carrier, excipient or vehicle.

Synthesis of Peptide Conjugates

The peptide conjugates of the invention may be manufactured by standard synthetic methods, by use of recombinant expression systems, or by any other suitable method. Thus, the conjugates may be synthesized in a number of ways, including, e.g., methods which comprise:

(a) synthesizing the peptide conjugate by means of standard solid-phase or liquid-phase methodology, either stepwise or by fragment assembly, and isolating and purifying the final peptide conjugate product;

(b) expressing a nucleic acid construct that encodes the peptide conjugate in a host cell and recovering the expression product from the host cell culture; or (c) effecting cell-free in vitro expression of a nucleic acid construct that encodes the peptide conjugate, and recovering the expression product;

or by any combination of methods of (a), (b) or (c) to obtain fragments of the peptide conjugate, subsequently ligating the fragments to obtain the peptide conjugate, and recovering the peptide conjugate.

It may often be preferable to synthesize the conjugates of the invention by means of solid-phase or liquid-phase peptide synthesis. In this connection, reference may be made to WO 98/11125 or, inter alia, Fields, G. B. et al., "Principles and Practice of Solid-Phase Peptide Synthesis"; in: *Synthetic Peptides*, Gregory A. Grant (ed.), Oxford University Press ($2^{nd}$ edition, 2002) and the synthesis examples herein.

One or more of the amino acid side chains in the compound of the invention may be further conjugated to a lipophilic substituent. The lipophilic substituent may be covalently bonded to an atom in the amino acid side chain, or alternatively may be conjugated to the amino acid side chain by a spacer. The amino acid may be part of the peptide Z, or part of the peptide Y.

Without wishing to be bound by theory, it is thought that the lipophilic substituent binds albumin in the blood stream, thus shielding the compounds of the invention from enzymatic degradation which can enhance the half-life of the compounds. The spacer, when present, is used to provide a spacing between the compound and the lipophilic substituent.

The lipophilic substituent may be attached to the amino acid side chain or to the spacer via an ester, a sulphonyl ester, a thioester, an amide or a sulphonamide. Accordingly it will be understood that preferably the lipophilic substituent includes an acyl group, a sulphonyl group, an N atom, an O atom or an S atom which forms part of the ester, sulphonyl ester, thioester, amide or sulphonamide.

Preferably, an acyl group in the lipophilic substituent forms part of an amide or ester with the amino acid side chain or the spacer.

The lipophilic substituent may include a hydrocarbon chain having 4 to 30 C atoms. Preferably it has at least 8 or 12 C atoms, and preferably it has 24 C atoms or fewer, or 20 C atoms or fewer. The hydrocarbon chain may be linear or branched and may be saturated or unsaturated. It will be understood that the hydrocarbon chain is preferably substituted with a moiety which forms part of the attachment to the amino acid side chain or the spacer, for example an acyl group, a sulphonyl group, an N atom, an O atom or an S atom. Most preferably the hydrocarbon chain is substituted with acyl, and accordingly the hydrocarbon chain may be part of an alkanoyl group, for example palmitoyl, caproyl, lauroyl, myristoyl or stearoyl.

Accordingly, the lipophilic substituent may have the formula shown below:

A may be, for example, an acyl group, a sulphonyl group, NH, N-alkyl, an O atom or an S atom, preferably acyl. n is an integer from 3 to 29, preferably at least 7 or at least 11, and preferably 23 or less, more preferably 19 or less.

The hydrocarbon chain may be further substituted. For example, it may be further substituted with up to three substituents selected from $NH_2$, OH and COOH. If the hydrocarbon chain is further substituted, preferably it is further substituted with only one substituent. Alternatively or additionally, the hydrocarbon chain may include a cycloalkane or heterocycloalkane, for example as shown below:

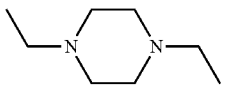

Preferably the cycloalkane or heterocycloalkane is a six-membered ring. Most preferably, it is piperidine.

Alternatively, the lipophilic substituent may be based on a cyclopentanophenanthrene skeleton, which may be partially or fully unsaturated, or saturated. The carbon atoms in the skeleton each may be substituted with Me or OH. For example, the lipophilic substituent may be cholyl, deoxycholyl or lithocholyl.

As mentioned above, the lipophilic substituent may be conjugated to the amino acid side chain by a spacer. When present, the spacer is attached to the lipophilic substituent and to the amino acid side chain. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may have the formula:

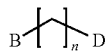

wherein B and D are each independently selected from acyl, sulphonyl, NH, N-alkyl, an O atom or an S atom, preferably from acyl and NH. Preferably, n is an integer from 1 to 10, preferably from 1 to 5. The spacer may be further substituted with one or more substituents selected from $C_{1-6}$ alkyl, $C_{0-6}$ alkyl amine, $C_{0-6}$ alkyl hydroxy and $C_{0-6}$ alkyl carboxy.

Alternatively, the spacer may have two or more repeat units of the formula above. B, D and n are each selected independently for each repeat unit. Adjacent repeat units may be covalently attached to each other via their respective B and D moieties. For example, the B and D moieties of the adjacent repeat units may together form an ester, a sulphonyl ester, a thioester, an amide or a sulphonamide. The free B and D units at each end of the spacer are attached to the amino acid side chain and the lipophilic substituent as described above.

Preferably the spacer has five or fewer, four or fewer or three or fewer repeat units. Most preferably the spacer has two repeat units, or is a single unit.

The spacer (or one or more of the repeat units of the spacer, if it has repeat units) may be, for example, a natural or unnatural amino acid. It will be understood that for amino acids having functionalized side chains, B and/or D may be a moiety within the side chain of the amino acid. The spacer may be any naturally occurring or unnatural amino acid. For example, the spacer (or one or more of the repeat units of the spacer, if it has repeat units) may be Gly, Pro, Ala, Val, Leu, Ile, Met, Cys, Phe, Tyr, Trp, His, Lys, Arg, Gln, Asn, α-Glu, γ-Glu, Asp, Ser Thr, Gaba, Aib, bAla, 5-aminopentanoyl, 6-aminohexanoyl, 7-aminoheptanoyl, 8-aminooctanoyl, 9-aminononanoyl or 10-aminodecanoyl.

For example, the spacer may be a single amino acid selected from γ-Glu, Gaba, b-Ala and α-Gly.

The lipophilic substituent may be conjugated to any amino acid side chain in the compounds of the invention. Preferably, the amino acid side chain includes an carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. Preferably, the lipophilic substituent is conjugated to Lys or Cys. However, any amino acid shown as Lys in the formulae provided herein may be replaced by Dbu, Dpr or Orn where a lipophilic substituent is added.

An example lipophilic substituent and spacer is shown in the formula below:

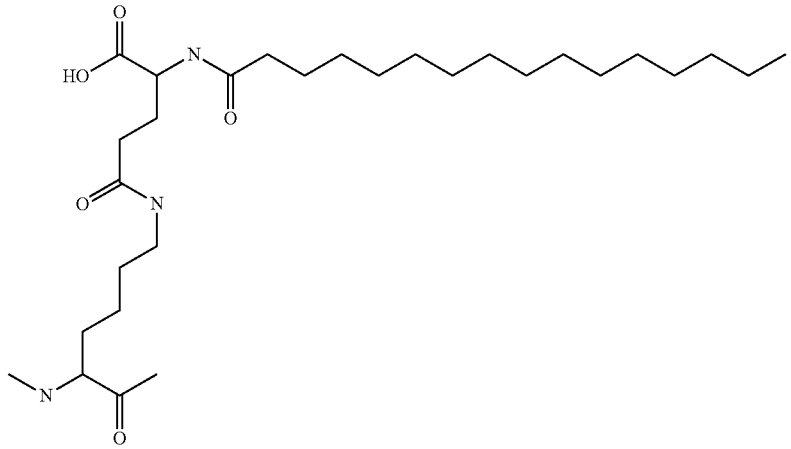 [SMILES: CCCCCCCCCCCCCCCC(=O)NC(CCC(=O)NCCCCC(NC)C(C)=O)C(=O)O]

Here, a Lys from the compound of the present invention (e.g. from X) is covalently attached to γ-Glu (the spacer) by via an amide moiety. Palmitoyl is covalently attached to the γ-Glu spacer via an amide moiety.

Alternatively or additionally, one or more amino acid side chains in the compound of the invention may be conjugated to a polymeric moiety, for example, in order to increase solubility and/or half-life in vivo (e.g. in plasma) and/or bioavailability. Such modification is also known to reduce clearance (e.g. renal clearance) of therapeutic proteins and peptides.

The polymeric moiety is preferably water soluble (amphiphilic or hydrophilic), non-toxic, and pharmaceutically inert. Suitable polymeric moieties include polyethylene glycol (PEG), homo- or co-polymers of PEG, a monomethyl-substituted polymer of PEG (mPEG), or polyoxyethylene glycerol (POG). See, for example, *Int. J. Hematology* 68:1 (1998); *Bioconjugate Chem.* 6:150 (1995); and *Crit. Rev. Therap. Drug Carrier Sys.* 9:249 (1992).

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57; Tsukada, et al. (1984), J. Natl. Cancer Inst., vol 73: 721-729; and Pratesi, et al. (1985), Br. J. Cancer, vol. 52: 841-848).

The polymeric moiety may be straight-chain or branched. It may have a molecular weight of 500-40,000 Da, for example 500-10,000 Da, 1000-5000 Da, 10,000-20,000 Da, or 20,000-40,000 Da.

A compound may comprise two or more such moieties, in which case the total molecular weight of all such moieties will generally fall within the ranges provided above.

The polymeric moiety may be coupled (by covalent linkage) to an amino, carboxyl or thiol group of an amino acid side chain. Preferred examples are the thiol group of Cys residues and the epsilon amino group of Lys residues, and the carboxyl groups of Asp and Glu residues may also be used.

The skilled reader will be well aware of suitable techniques which can be used to perform the coupling reaction. For example, a PEG moiety carrying a methoxy group can be coupled to a Cys thiol group by a maleimido linkage using reagents commercially available from Nektar Therapeutics AL. See also WO 2008/101017, and the references cited above for details of suitable chemistry.

Therapeutic Uses

In the following, it will be understood that reference to the use of a peptide conjugate of the invention also encompasses use of a pharmaceutically acceptable salt or solvate thereof.

The peptide conjugates of the invention may provide an attractive treatment option for metabolic diseases or disorders, including diabetes, in particular type 1 and/or type 2 diabetes, and possibly obesity.

Diabetes comprises a group of metabolic diseases characterized by hyperglycemia resulting from defects in Insulin secretion, Insulin action, or both. Acute signs of diabetes include excessive urine production, resulting compensatory thirst and increased fluid intake, blurred vision, unexplained weight loss, lethargy, and changes in energy metabolism. The chronic hyperglycemia of diabetes is associated with macro- and microvascular complications that can lead to long-term damage, dysfunction, and—in some cases—ultimately failure of various organs, particularly the eyes (notably in the form of diabetic retinopathy), kidneys (in the form of diabetic nephropathy), nerves (in the form of diabetic neuropathy), heart and blood vessels. Diabetes may be subdivided into three classes, viz. type 1 diabetes, type 2 diabetes and gestational diabetes, on the basis on pathogenetic characteristics.

Type 1 diabetes accounts for 5-10% of all diabetes cases and is caused by auto-immune destruction of Insulin-secreting pancreatic β-cells.

Type 2 diabetes accounts for 90-95% of diabetes cases and is a result of a complex set of metabolic disorders. Type 2 diabetes is the consequence of endogenous Insulin production and/or whole-body Insulin sensitivity becoming insufficient to maintain plasma glucose levels below the diagnostic thresholds.

Gestational diabetes refers to any degree of glucose intolerance identified during pregnancy.

A condition known as pre-diabetes is also recognized. It includes, e.g., impaired fasting glucose levels and impaired glucose tolerance, and refers generally to those states that occur when blood glucose levels are elevated, but are below levels that are established for the clinical diagnosis for diabetes.

A large proportion of subjects with type 2 diabetes and pre-diabetes are at increased risk of morbidity and mortality due to the high prevalence of additional metabolic risk factors, including abdominal obesity (excessive fat tissue around the abdominal internal organs), atherogenic dyslipidemia (blood fat disorders, including high triglyceride levels, low HDL cholesterol levels and/or high LDL cholesterol levels, which foster plaque build-up in artery walls), elevated blood pressure (hypertension), a prothrombotic state (e.g. high Fibrinogen or Plasminogen activator inhibitor-1 levels in the blood), and a proinflammatory state (e.g., elevated C-reactive protein levels in the blood).

Conversely, obesity confers an increased risk of developing, for example, pre-diabetes, type 2 diabetes, certain types of cancer, obstructive sleep apnea and gall-bladder disease.

Dyslipidemia is associated with increased risk of cardiovascular disease. High Density Lipoprotein (HDL) is of clinical importance since an inverse correlation exists between plasma HDL concentrations and risk of atherosclerotic disease. The major part of cholesterol stored in atherosclerotic plaques originates from Low Density Lipoproteins (LDL), and hence elevated concentrations of LDL are closely associated with atherosclerosis. The HDL/LDL ratio is a parameter employed is assessing clinical risk of atherosclerosis and coronary atherosclerosis in particular.

Without being bound by any particular theory, it appears that the peptide conjugates of the invention may unexpectedly combine the physiological effects of GLP-1 receptor agonists with those of Gastrin peptides vide supra in a manner such that the observed activity may be significantly greater than that observed when employing a corresponding additive (non-conjugated) combination of the individual peptide components. It is consequently believed that the peptide conjugates of the invention may be of particular benefit in the treatment of pre-diabetes, diabetes (notably type 1 and/or type 2 diabetes) and diabetes-related conditions, diseases or disorders such as those discussed above, including treatment to promote pancreatic islet β-cell formation (islet neogenesis), and thereby Insulin production, that will be beneficial with respect to regulation of blood glucose concentrations. Peptide conjugates of the invention may therefore be of value, inter alia, in limiting or arresting disease progression in type 1 and/or type 2 diabetes.

The peptides of the present invention may further be useful for promoting survival and inhibiting apoptosis of β-cells in the pancreatic islets. Effects of GLP-1 and Gastrin includes effects on β-cell proliferation and maturation but also prevention of β-cell apoptosis and enhanced neogenesis, thus the effects of the peptides of the invention may include such effects and thereof effects on improved insulin and glucose regulation.

The peptide conjugates of the present invention may thus be useful as pharmaceutical agents for treatment of Insulin resistance, glucose intolerance, pre-diabetes, elevated fasting glucose levels, type 1 and/or type 2 diabetes, hypertension and/or dyslipidemia (or a combination of these metabolic risk factors), atherosclerosis, arteriosclerosis, coronary heart disease, peripheral artery disease and stroke. They may also be useful in preventing weight gain, promoting weight loss, reducing excess body weight and/or treating obesity (e.g. by control of appetite, feeding, food intake, calorie intake, and/ or energy expenditure), including morbid obesity, as well as associated diseases, disorders and health conditions, including, but not limited to, obesity-linked inflammation, obesity-linked gallbladder disease and obesity-induced sleep apnea. Effects of the peptide conjugates of the invention on these conditions may be mediated in whole or in part via an effect on body weight, or may be independent thereof.

Pharmaceutical Compositions

In the following, it will be understood that reference to the inclusion of one or more of a peptide conjugate of the invention in a pharmaceutical composition also encompasses inclusion of a pharmaceutically acceptable salt or solvate of a peptide conjugate of the invention.

The peptide conjugates of the present invention may be formulated as pharmaceutical compositions which are suited for administration with or without storage, and which typically comprise a therapeutically effective amount of at least one peptide conjugate of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, Pa., USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration. Pharmaceutically acceptable carriers or diluents include those used in formulations suitable for e.g. oral, intraviteral, rectal, vaginal, nasal, topical, enteral or parenteral (including subcutaneous, intramuscular, intravenous, intradermal and transdermal) administration or administration by inhalation. The formulations may conveniently be presented in unit dosage form and may be prepared by any of the methods well known in the art of pharmaceutical formulation.

Subcutaneous or transdermal modes of administration may be particularly suitable for the peptide conjugates of the invention.

A further aspect of the invention relates to devices, dosage forms and packages used to deliver the pharmaceutical formulations of the present invention. Thus, at least one peptide conjugate or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

A still further aspect of the invention relates to oral formulations and administration. Formulations for oral may rely on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidant such as cysteine, disintegrator, binder, thickener, buffering agent, sweetening agent, flavoring agent, perfuming agent, etc.

Dosages

A typical dosage of a peptide conjugate of the invention as employed in the context of the present invention may be in the range from about 0.001 to about 100 mg/kg body weight per day, such as from about 0.01 to about 50 mg/kg body weight per day, e.g. from about 0.05 to about 10 mg/kg body weight per day, administered in one or more doses, such as from one to three doses. As already indicated to some extent above, the exact dosage employed will depend, inter alia, on: the nature and severity of the disease or disorder to be treated; the sex, age, body weight and general condition of the subject to be treated; possible other, concomitant disease or disorder that is undergoing or is to undergo treatment; as well as other factors that will be known to a medical practitioner of skill in the art.

Combination Therapy

As noted above, it will be understood that reference in the following to a peptide conjugate of the invention also extends to a pharmaceutically acceptable salt or solvate thereof as well as to a composition comprising more than one different peptide conjugate of the invention.

A peptide conjugate of the invention may be administered as part of a combination therapy together with another active agent for the treatment of the disease or disorder in question, e.g. diabetes, obesity, metabolic syndrome, dyslipidemia or hypertension, and in such cases, the two active agents may be given together or separately, e.g. as constituents in the same pharmaceutical composition or formulation, or as separate formulations.

Thus a peptide conjugate of the invention may be used in combination with an anti-diabetic agent of known type, including, but not limited to, Metformin, a sulfonylurea, a glinide, a DPP-IV inhibitor, a glitazone, or Insulin or an Insulin analogue. In a preferred embodiment, the peptide conjugate of the invention is administered in combination with Insulin or an analogue thereof, a DPP-IV inhibitor, sulfonylurea or Metformin, particularly sulfonylurea or Metformin, for achieving adequate glycemic control. In a more preferred embodiment, the peptide conjugate is administered in combination with Insulin or an Insulin analogue for achieving adequate glycemic control. Examples of appropriate Insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™; Exendin-4) and liraglutide (Victoza™)

A peptide conjugate of the invention may also be used in combination with an anti-obesity agent of known type, including, but not limited to, Peptide YY or an analogue thereof, Neuropeptide Y (NPY) or an analogue thereof, a cannabinoid receptor 1 antagonist, a lipase inhibitor, Human prolslet Peptide (HIP), a Melanocortin receptor 4 agonist or a Melanin concentrating hormone receptor 1 antagonist.

A peptide conjugate of the invention may further be used in combination with an anti-hypertension agent of known type, including, but not limited to, an angiotensin-converting enzyme inhibitor, an Angiotensin II receptor blocker, a diuretic, a beta-blocker or a calcium channel blocker.

A peptide conjugate of the invention may still further be used in combination with an anti-dyslipidemia agent of known type, including, but not limited to, a statin, a fibrate, a niacin and/or a cholesterol absorption inhibitor.

A peptide conjugate of the invention may also be used in combination with a proton pump inhibitor (i.e. a pharmaceutical agent possessing pharmacological activity as an inhibitor $H^+/K^+$-ATPase) of known type, including, but not limited to, an agent of the benzimidazole derivative type or of the imidazopyridine derivative type, such as Omeprazole™, Lansoprazole™, Dexlansoprazole™ Esomeprazole™, Pantoprazole™, Rabeprazole™, Zolpidem™, Alpidem™, Saripidem™ or Necopidem™.

A peptide conjugate of the invention may, moreover, be used in combination with an anti-inflammatory agent of known type, including, but not limited to:
steroids and corticosteroids, such as beclomethasone, methylprednisolone, betamethasone, prednisone, dexamethasone, and hydrocortisone;
non-steroidal antiinflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);

COX II inhibitors, such as rofecoxib and celecoxib; preparations of interferon beta (e.g. interferon beta-1a or interferon beta-1b);
and certain other compounds, such as 5-aminosalicylic acid and prodrugs and pharmaceutically acceptable salts thereof.

Metformin has also been demonstrated to have anti-inflammatory properties [see Haffner et al., *Diabetes* 54: 1566-1572 (2005)] and as such may also be useful in the present context Each of the cited publications and patent applications are incorporated herein by reference in its entirety The following examples demonstrate certain specific embodiments of the present invention. The following examples were carried out using standard techniques, which are well known and routine to those of skill in the art, except where otherwise described in detail. It is to be understood that these examples are for illustrative purposes only and do not purport to be wholly definitive as to conditions or scope of the invention. As such, they should not be construed in any way as limiting the scope of the present invention.

EXAMPLES

Abbreviations employed in the examples include:
NMP: N-methylpyrrolidone
DCM: dichloromethane
DMF: N,N-dimethylformamide
HATU: 2-(7-aza-1H-benzotriazole-1-yl)-1,1,3,3-tetramethyluronium hexafluorophosphate
DIPEA: diisopropylethylamine
EtOH: ethanol
$Et_2O$: diethyl ether
Peg3: 8-amino-3,6-dioxaoctanoyl
8Aoc: 8-aminooctanoyl
DBF: 4-(2-aminoethyl)-6-dibenzofuranpropanoyl
TFA: trifluoroacetic acid
MeCN: acetonitrile
HPLC: high performance liquid chromatography
MS: mass spectrometry
IBMX: 3-isobutyl-1-methylxanthine
BSA: bovine serum albumin
cAMP: cyclic adenosine monophosphate
DMEM: Dulbecco's Modified Eagle Medium
FCS: fetal calf serum
HEPES: N-2-hydroxyethylpiperazine-N'-2-ethanesulfonic acid
p-ERK: phosphorylated extracellular regulated kinase
PBS: phosphate-buffered saline
Boc: t-Butoxycarbonyl
NEP: N-methylpyrrolidone
Liraglutide: [Arg34,Lys(Hexadecanoyl-isoGlu)26]GLP-1 (7-37)

Example 1

Synthesis of Compounds and Peptide Properties

Materials and Methods
Unless otherwise specified, reagents and solvents employed in the following were available commercially in standard laboratory reagent or analytical grade, and were used without further purification.
General Procedure for Synthesis of Peptide Conjugates of the Invention
Solid phase peptide synthesis was performed on a CEM Liberty Peptide Synthesizer using standard Fmoc chemistry. TentaGel™ S Ram resin (1 g; 0.25 mmol/g) was swelled in NMP (10 ml) prior to use and transferred between tube and reaction vessel using DCM and NMP. Pseudoprolines, which are dipeptides employed to minimize aggregation during peptide synthesis, such as Fmoc-Phe-Thr(ψ-Me,Me-Pro)-OH and Fmoc-Asp-Ser(ψ-Me,Me-Pro)-OH, were used where appropriate, and the non-natural amino acids forming the Peg3, 8Aoc and DBF linker moieties (vide supra) were employed as Fmoc-protected amino acids (i.e. Fmoc-Peg3-OH, Fmoc-8Aoc-OH and Fmoc-DBF-OH, respectively), and without any changes to the general procedure.

Coupling:

An Fmoc-amino acid in NMP/DMF/DCM (1:1:1; 0.2 M; 5 ml) was added to the resin in a CEM Discover microwave unit together with HATU/NMP (0.5 M; 2 ml) and DIPEA/NMP (2.0 M; 1 ml). The coupling mixture was heated to 75° C. for 5 min while nitrogen was bubbled through the mixture. The resin was then washed with NMP (4×10 ml).

Deprotection:

Piperidine/NMP (20%; 10 ml) was added to the resin for initial deprotection, and the mixture was microwave-heated (40° C.; 30 sec.). The reaction vessel was drained and a second portion of piperidine/NMP (20%; 10 ml) was added and heated (75° C.; 3 min) again. The resin was then washed with NMP (6×10 ml).

Cleavage:

The resin was washed with EtOH (3×10 ml) and $Et_2O$ (3×10 ml) and dried to constant weight at room temperature (r.t.). The crude peptide was cleaved from the resin by treatment with TFA/ethanedithiol (95/5, 40 ml, 2 h; r.t.). Most of the TFA was removed under reduced pressure, and the crude peptide was precipitated and washed three times with $Et_2O$ and dried to constant weight at room temperature.

Purification and Characterisation:

The crude peptide was purified to greater than 90% purity by preparative reverse phase HPLC using a PerSeptive Biosystems VISION Workstation equipped with a suitable column and a fraction collector, and run with a gradient of buffer A (0.1% TFA, aq.) and buffer B (0.1% TFA, 90% MeCN, aq.). Fractions were analysed by analytical HPLC and MS, and relevant fractions were pooled and lyophilised. The final product was characterised by HPLC and MS.

Synthesis Example

Exendin-4(1-39)-Peg3-Peg3-[Gln1,Leu15]Gastrin17 (Compound 1) was synthesized on a CEM Liberty Peptide Synthesizer using TentaGel S Ram resin (0.67 g; 0.23 mmol/g) and Fmoc chemistry as described above. Fmoc-8-amino-3,6-dioxaoctanoic acid and pseudoprolines Fmoc-Phe-Thr(ψ-Me,Me-Pro)-OH and Fmoc-Ser(tBu)-Ser(ψ-Me,Me-Pro)-OH were employed.

The peptide was cleaved from the resin as described above, and the purification was performed on a Gemini-NX column (5×25 cm; 10 μm; C18) with a 35 ml/min flow of a mixture of buffer A (0.1% TFA; aq.) and buffer B (0.1% TFA; 90% MeCN; aq.). The product was eluted with a linear gradient from 20% to 50% buffer B over 47 min, and fractions (9 ml) were collected with a fraction collector. Relevant fractions were analysed by analytical HPLC and MS, pooled and lyophilised to give a white powder (122 mg), which was analysed by analytical HPLC as being 58% pure.

The product was purified again on a Luna column (1×25 cm; 5 μm; C8) with a 4 ml/min flow of a mixture of buffer A (0.1% TFA; aq.) and buffer B (0.1% TFA; 90% MeCN; aq.). The product was eluted with a linear gradient from 20% to 50% buffer B over 47 min, and fractions (2 ml) were collected with a fraction collector. Relevant fractions were analysed by analytical HPLC and MS, pooled and lyophilised to a give white powder (63 mg), which was analysed by analytical HPLC as being 82% pure.

Another portion of Compound 1 was synthesized using TentaGel S Ram resin (0.70 g; 0.23 mmol/g) and otherwise the same conditions as described above for synthesis and cleavage.

Purification was performed on a Gemini-NX column (5×25 cm; 10 μm; C18) with a 35 ml/min flow of a mixture of buffer A (0.1% TFA; aq.) and buffer B (0.1% TFA; 90% MeCN; aq.). The product was eluted with a linear gradient from 20% to 50% buffer B over 47 min, and fractions (9 ml) were collected with a fraction collector. Relevant fractions were analysed by analytical HPLC and MS, pooled and lyophilised to give a white powder (113 mg), which was analysed by analytical HPLC as being 57% pure.

The product was purified again on a Luna column (1×25 cm; 5 μm; C8) with a 4 ml/min flow of a mixture of buffer A (0.1% TFA; aq.) and buffer B (0.1% TFA; 90% MeCN; aq.). The product was eluted with a linear gradient from 20% to 55% buffer B over 47 min, and fractions (2 ml) were collected with a fraction collector. Relevant fractions were analysed by analytical HPLC and MS, pooled and lyophilised to give a white powder (29 mg), which was analysed by analytical HPLC as being 77% pure.

The products from the first synthesis (63 mg; 82%) and second synthesis (29 mg; 77%) were combined and purified once more on a Kromasil column (1×25 cm; 10 μm; C8) with a 4 ml/min flow of a mixture of buffer A (0.1% TFA; aq.) and buffer B (0.1% TFA; 90% MeCN; aq.). The product was eluted with a linear gradient from 25% to 65% buffer B over 47 min, and fractions (2 ml) were collected with a fraction collector. Relevant fractions were analysed by analytical HPLC and MS, pooled and lyophilised to give a white powder (33 mg), which was analysed by analytical HPLC as being 94% pure. The mass was 6553.39 Da as determined by MS (Calc. 6553.06 Da).

Exendin-4(1-28)-Peg3-Peg3-[Leu4]Gastrin6 (Compound 33) was synthesized on a CEM Liberty Peptide Synthesizer using TentaGel S Ram resin (0.55 g; 0.23 mmol/g) and Fmoc chemistry as described above. Fmoc-8-amino-3,6-dioxaoctanoic acid and pseudoproline Fmoc-Phe-Thr(ψ-Me,Me-Pro)-OH were employed.

The peptide was cleaved from the resin as described above, and the purification was performed on a Gemini-NX column (5×25 cm; 10 μm; C18) with a 35 ml/min flow of a mixture of buffer A (0.1% TFA; aq.) and buffer B (0.1% TFA; 90% MeCN; aq.). The product was eluted with a linear gradient from 25% to 55% buffer B over 47 min, and fractions (9 ml) were collected with a fraction collector. Relevant fractions were analysed by analytical HPLC and MS, pooled and lyophilised to give a white powder (70 mg), which was analysed by analytical HPLC as being 90% pure. The mass was 4364.08 Da as determined by MS (Calc. 4364.11 Da).

[Glu9,Leu14,Phe25,Tyr13]Exendin-4(1-27)-[Leu4]Gastrin6 (Compound 101) was synthesized on a CEM Liberty Peptide Synthesizer using TentaGel S Ram resin (1.15 g; 0.25 mmol/g) and Fmoc chemistry as described above using Fmoc-Phe-Thr(ψ-Me,Me-Pro)-OH. NEP was used instead of NMP during coupling and deprotection.

The peptide was cleaved from the resin as described above, and the purification was performed on a Gemini-NX column (5×25 cm; 10 μm; C18) with a 35 ml/min flow of a mixture of buffer A (0.1% TFA; aq.) and buffer B (0.1% TFA; 90% MeCN; aq.). The product was eluted with a linear gradient from 20% to 50% buffer B over 47 min, and fractions (9 ml) were collected with a fraction collector. Relevant fractions were analysed by analytical HPLC and MS, pooled and lyophilised to give a white powder (50 mg), which was analysed by analytical HPLC as being 85% pure. The mass was 3952.00.08 Da as determined by MS (Calc. 3951.97 Da).

GLP-1(7-36)-Peg3-Peg3-[Gln1,Leu15]Gastrin17 (Compound 42) was synthesized on a CEM Liberty Peptide Synthesizer using TentaGel S Ram resin (1.16 g; 0.23 mmol/g) and Fmoc chemistry as described above. Fmoc-8-amino-3,6-dioxaoctanoic acid and pseudoproline Fmoc-Ser(tBu)-Ser (Psi Me, Me pro)-OH were employed.

The peptide was cleaved from the resin as described above, and the purification was performed on a Gemini-NX column (5×25 cm; 10 µm; C18) with a 35 ml/min flow of a mixture of buffer A (0.1% TFA; aq.) and buffer B (0.1% TFA; 90% MeCN; aq.). The product was eluted with a linear gradient from 25% to 45% buffer B over 47 min, and fractions (9 ml) were collected with a fraction collector. Relevant fractions were analysed by analytical HPLC and MS, pooled and lyophilised to give a white powder (172 mg), which was analysed by analytical HPLC as being 86% pure. The mass was 5664.72 Da as determined by MS (Calc. 5664.70 Da).

[Arg34,Lys(Hexadecanoyl-isoGlu)26]GLP-1(7-37)-Peg3-Peg3-[Leu4]Gastrin6 (Compound 107) was synthesized on a CEM Liberty Peptide Synthesizer using TentaGel S Ram resin (1.30 g; 0.25 mmol/g) and Fmoc chemistry as described above. NEP was used instead of NMP during coupling and deprotection. Fmoc-8-amino-3,6-dioxaoctanoic acid and pseudoproline Fmoc-Phe-Thr(ψ-Me,Me-Pro)-OH were employed as well as Fmoc-Lys(Dde)-OH at the point of attachment for the acylation.

The N-terminal of the solid-phase attached peptide was Boc protected using $Boc_2O$ (330 mg) and DIPEA (54 µl) in DCM. Then the Dde protection group was cleaved using hydrazine hydrate/NEP (4%; 2×15 min), and the resin was washed with NEP (8×2 min), DIEA/NEP (10%; 5×5 min) and NEP (8×2 min). The synthesis was completed on a CEM Liberty Peptide Synthesizer as described above using Fmoc-Glu-OtBu and hexadecanoic acid. NEP was used instead of NMP during coupling and deprotection.

The peptide was cleaved from the resin as described above, and the purification was performed on a Gemini-NX column (5×25 cm; 10 µm; C18) with a 35 ml/min flow of a mixture of buffer A (0.1% TFA; aq.) and buffer B (0.1% TFA; 90% MeCN; aq.). The product was eluted with a linear gradient from 30% to 70% buffer B over 47 min, and fractions (9 ml) were collected with a fraction collector. Relevant fractions were analysed by analytical HPLC and MS, pooled and lyophilised to give a white powder (60 mg), which was analysed by analytical HPLC as being 88% pure. The mass was 4819.95 Da as determined by MS (Calc. 4819.45 Da).

Example 2

Activation ($EC_{50}$) of GLP-1 Receptor and Gastrin CCK-B Receptor In Vitro by Peptide Conjugates of the Invention Materials and Methods
Human GLP-1 Receptor (GLP-1R) Efficacy Assay:

In vitro effects of peptide conjugates of the invention were assessed by measuring the induction of cAMP following stimulation of the receptor by GLP-1(7-36), Exendin-4(1-39) or tested conjugates of the invention using the FlashPlate™ cAMP kit from Perkin-Elmer. Briefly, HEK293 cells expressing the human GLP-1 R (stable cell line generated through transfection of the cDNA for GLP-1 R and selection of stable clones) were seeded at 40,000 cells/well in 96-well microtiter plates coated with 0.01% poly-L-lysine, and grown for 1 day in culture in 100 µl growth medium [DMEM, 10% FCS, Penicillin (100 IU/ml), Streptomycin (100 µg/ml)]. On the day of analysis, growth medium was removed and the cells were washed once with 200 µl Tyrode buffer [Tyrode's Salts (9.6 g/l), 10 mM HEPES, pH 7.4]. Cells were incubated in 100 µl Tyrode buffer containing increasing concentrations of test compounds, 100 µM IBMX, and 0.1% BSA for 15 min at 37° C. The reaction was stopped by addition of 25 µl 0.5 M HCl and incubated on ice for 60 min. For further methodological details, see WO 2008/152403.

CCK-B Receptor (CCK-B R) Efficacy Assay:

To test binding and activation of CCK-B R we produced stable cell lines expressing one of the human or mouse CCK receptors in a manner similar to that for production of the hGLP-1 R cell lines were generated (vide supra). In brief, we used HEK293 cells for transfection of the cDNA for human or mouse CCK-A R or CCK-B R [hCCK-A R (gene identity: L19315), hCCK-B R(NM__176875), mCCK-A R(NM__009827) and mCCK-B R(NM__007627)] all cloned into the transfection plasmid pIRES-neo2dNGFR. The cells were grown according to standard protocol in growth medium and transfected with the plasmids using Lipofectamin (Invitrogen). The cells stably expressing CCK receptors were selected using G418 in the growth medium (only cells that have taken up and incorporated the cDNA expression plasmid survive) and propagated. Stocks of cells were frozen for later use.

In vitro effects of peptide conjugates of the invention were estimated by measuring p-ERK (using the AlphaScreen™ SureFire p-ERK assay) in HEK293 cells stably expressing the human and mouse CCK-B R (high-affinity Gastrin receptor), respectively. The Gastrin receptor efficacy assays (AlphaScreen™ SureFire p-ERK assay) were performed as follows:

Day 1: Seeding of Cells

The CCK-B R expressing cells in question were seeded at 20,000 cells/well in 100 µl growth medium [DMEM, 10% FCS, Penicillin (100 IU/ml), Streptomycin (100 µg/ml)] in a 96-well plate coated with poly-D-lysine. The cells were incubated in an incubator (37° C., 5% $CO_2$) for two days.

Day 3: Change to Serum-Free Medium

The growth medium was changed to 80 µl of serum-free medium [DMEM, Penicillin (100 IU/ml), Streptomycin (100 µg/ml)] per well, and incubation of the cells was continued for 19 hours in the incubator (37° C., 5% $CO_2$).

Day 4: Peptide Conjugate Stimulation and AlphaScreen™ SureFire p-ERK Assay

1. After 19 hours, 20 µl of serum-free medium containing one of 5 different concentrations of peptide conjugate was added (performed in triplicate for each concentration), and the cells were incubated for 5 min. at room temperature.
2. The stimulation medium was discarded by quickly turning the plate upside down, and 60 µl 1× lysis buffer (from the SureFire assay kit) was added per well.
3. The plate was shaken on a plate-shaker for 5 min and then placed on ice.
4. SureFire P-ERK assay: 4 µl of each supernatant was transferred to a 384 well proxiplate (Perkin Elmer).
5. 4 µl of each of the two control lysates (unstimulated and stimulated) were added to the proxiplate in duplicate.
6. 60 parts reaction buffer, 10 parts activation buffer, 1 part acceptor beads and 1 part donor beads were mixed (reaction buffer+activation buffer+beads). 7 µl of the latter reaction buffer+activation buffer+beads per well were added in the proxiplate, the mix being resuspended carefully before addition to the wells.
7. The plate was incubated for 2 hours in a dark box in a 22° C. incubator.
8. The plate was analyzed on an Envision™ light-emission plate reader (Perkin-Elmer) using the appropriate reading program (Perkin-Elmer).

The peptide conjugates of the invention were tested in the above-described assays (i.e. human GLP-1 R activation efficacy, human CCK-B R activation efficacy and mouse CCK-B R activation efficacy).

Human GLP-1(7-36) and Exendin-4(1-39) were used as positive controls in the human GLP-1 receptor (hGLP-1R) activation efficacy assay, and h[Gln1,Leu15]Gastrin17 and CCK-8 (consisting of the C-terminal 8 active amino acid residues of CCK) were used as positive controls in the human CCK-B receptor (hCCK-B R) efficacy assay and the mouse CCK-B receptor (mCCK-B R) assay.

In the present CCK receptor activation study, h[Gln1, Leu15]Gastrin17 (having the sequence HQGPWLEEEEE-AYGWLDF-NH$_2$) was used as a control compound. The glutamine (Gln) residue may rearrange to some extent to PyroGlu, but without loss of receptor binding activity.

The results (EC$_{50}$ values, in mol/l) are summarized in Tables 1, 1a and 2, below.

TABLE 1 in vitro efficacy (EC$_{50}$, mol/l) of compounds (peptide conjugates) of the invention in activation of hGLP-1 R, hCCK-B R and mCCK-B R.

| Cpd No. | Peptide conjugate | hGLP-1 R EC$_{50}$ | hCCK-B R EC$_{50}$ | mCCK-B R EC$_{50}$ |
|---|---|---|---|---|
| 1 | Exendin-4(1-39)-Peg3-Peg3-[Gln1,Leu15]Gastrin17 | $5.68 \times 10^{-10}$ | $1.90 \times 10^{-8}$ | $5.40 \times 10^{-8}$ |
| 33 | Exendin-4(1-28)-Peg3-Peg3-[Leu4]Gastrin6 | $7.74 \times 10^{-10}$ | $3.08 \times 10^{-8}$ | $7.15 \times 10^{-8}$ |
| 37 | GLP-1(7-36)-[Gln1,Leu15]Gastrin17 | $1.45 \times 10^{-10}$ | $2.59 \times 10^{-8}$ | $7.31 \times 10^{-8}$ |
| 38 | GLP-1(7-36)-K-[Gln1,Leu15]Gastrin17 | $8.42 \times 10^{-11}$ | $7.73 \times 10^{-8}$ | $1.14 \times 10^{-7}$ |
| 39 | GLP-1(7-36)-AAA-[Gln1,Leu15]Gastrin17 | $1.14 \times 10^{-10}$ | $1.88 \times 10^{-8}$ | $5.41 \times 10^{-8}$ |
| 40 | GLP-1(7-36)-SKK-[Gln1,Leu15]Gastrin17 | $1.16 \times 10^{-10}$ | $1.56 \times 10^{-8}$ | $5.86 \times 10^{-8}$ |
| 41 | GLP-1(7-36)-Peg3-SKK-[Gln1,Leu15]Gastrin17 | $9.26 \times 10^{-11}$ | $8.76 \times 10^{-9}$ | $5.11 \times 10^{-8}$ |
| 42 | GLP-1(7-36)-Peg3-Peg3-[Gln1,Leu15]Gastrin17 | $7.78 \times 10^{-11}$ | $8.20 \times 10^{-9}$ | $5.83 \times 10^{-8}$ |
| 43 | GLP-1(7-36)-8Aoc-SKK-[Gln1,Leu15]Gastrin17 | $1.56 \times 10^{-10}$ | $5.19 \times 10^{-8}$ | $8.25 \times 10^{-8}$ |
| 44 | GLP-1(7-36)-DBF-SKK-[Gln1,Leu15]Gastrin17 | $1.37 \times 10^{-10}$ | $2.57 \times 10^{-8}$ | $8.69 \times 10^{-8}$ |
| 45 | GLP-1(7-36)-8Aoc-8Aoc-[Gln1,Leu15]Gastrin17 | $1.22 \times 10^{-10}$ | $1.28 \times 10^{-8}$ | $7.14 \times 10^{-8}$ |
| Control | GLP-1(7-36) | $1.66 \times 10^{-11}$ | | |
| Control | Exendin-4(1-39) | $1.63 \times 10^{-10}$ | | |
| Control | h[Gln1,Leu15]Gastrin17 | | $4.69 \times 10^{-9}$ | $1.82 \times 10^{-8}$ |
| Control | CCK-8 | | $6.1 \times 10^{-9}$ | $1.63 \times 10^{-7}$ |

TABLE 1a

In vitro efficacy (EC$_{50}$, mol/l) of compounds (peptide conjugates) of the invention in activation of hGLP-1 R, hCCK-B R and mCCK-B R.

| Cpd. No. | Peptide conjugate | hGLP-1 R EC$_{50}$ | hCCK-B R EC$_{50}$ | mCCK-B R EC$_{50}$ |
|---|---|---|---|---|
| 1 | Exendin-4(1-39)-Peg3-Peg3-[Gln1,Leu15]Gastrin17 | $2.7 \times 10^{-11}$ | $8.0 \times 10^{-9}$ | $5.4 \times 10^{-8}$ |
| 33 | Exendin-4(1-28)-Peg3-Peg3-[Leu4]Gastrin6 | $2.8 \times 10^{-11}$ | $1.1 \times 10^{-8}$ | $7.1 \times 10^{-8}$ |

TABLE 2

In vitro efficacy (EC$_{50}$, mol/l) of further compounds (peptide conjugates) of the invention in activation of hGLP-1 R and hCCK-B R.

| Cpd. No. | Peptide conjugate | hGLP-1 R EC$_{50}$ | hCCK-B R EC$_{50}$ |
|---|---|---|---|
| 55 | Exendin-4(1-28)-Peg3-Peg3-[Leu3]Gastrin5 | $4.2 \times 10^{-11}$ | $7.4 \times 10^{-9}$ |
| 56 | Exendin-4(1-28)-Peg3-Peg3-[Ala1,Leu4]Gastrin6 | $2.2 \times 10^{-11}$ | $9.1 \times 10^{-9}$ |
| 57 | Exendin-4(1-28)-Peg3-Peg3-[Ala2,Leu4]Gastrin6 | $3.3 \times 10^{-11}$ | $7.2 \times 10^{-9}$ |
| 58 | Exendin-4(1-27)-Peg3-Peg3-[Leu4]Gastrin6 | $3.3 \times 10^{-11}$ | $96 \times 10^{-9}$ |
| 59 | Exendin-4(1-28)-Peg3-Peg3-[Leu2]Gastrin4 | $2.5 \times 10^{-11}$ | $9.00 \times 10^{-9}$ |
| 60 | [Leu14]Exendin-4(1-28)-Peg3-Peg3-[Leu4]Gastrin6 | $4.1 \times 10^{-11}$ | $6.3 \times 10^{-9}$ |
| 61 | [Orn12]Exendin-4(1-28)-Peg3-Peg3-[Leu4]Gastrin6 | $2.8 \times 10^{-11}$ | $5.8 \times 10^{-9}$ |
| 62 | [Orn27]Exendin-4(1-28)-Peg3-Peg3-[Leu4]Gastrin6 | $3.1 \times 10^{-11}$ | $5.6 \times 10^{-9}$ |
| 63 | [Phe25]Exendin-4(1-28)-Peg3-Peg3-[Leu4]Gastrin6 | $4.1 \times 10^{-11}$ | $8.5 \times 10^{-9}$ |
| 64 | [Asp28]Exendin-4(1-28)-Peg3-Peg3-[Leu4]Gastrin6 | $6.1 \times 10^{-11}$ | $3.3 \times 10^{-9}$ |
| 65 | [Tyr13]Exendin-4(1-28)-Peg3-Peg3-[Leu4]Gastrin6 | $4.6 \times 10^{-11}$ | $1.2 \times 10^{-8}$ |
| 66 | [Orn20]Exendin-4(1-28)-Peg3-Peg3-[Leu4]Gastrin6 | $3.8 \times 10^{-11}$ | $1.5 \times 10^{-8}$ |
| 67 | Exendin-4(1-28)-Peg3-[Leu4]Gastrin6 | $5.0 \times 10^{-11}$ | $1.0 \times 10^{-8}$ |
| 68 | Exendin-4(1-28)-[Leu4]Gastrin6 | $6.1 \times 10^{-11}$ | $1.4 \times 10^{-8}$ |
| 69 | Exendin-4(1-27)-[Leu4]Gastrin11 | $1.0 \times 10^{-10}$ | $4.3 \times 10^{-9}$ |
| 70 | Exendin-4(1-27)-Peg3-[Leu4]Gastrin6 | $1.4 \times 10^{-11}$ | $5.3 \times 10^{-9}$ |

TABLE 2-continued

In vitro efficacy (EC$_{50}$, mol/l) of further compounds (peptide conjugates) of the invention in activation of hGLP-1 R and hCCK-B R.

| Cpd. No. | Peptide conjugate | hGLP-1 R EC$_{50}$ | hCCK-B R EC$_{50}$ |
|---|---|---|---|
| 71 | Exendin-4(1-27)-Peg3-[Leu3]Gastrin5 | $2.9 \times 10^{-11}$ | $4.1 \times 10^{-9}$ |
| 72 | Exendin-4(1-26)-Peg3-[Leu3]Gastrin5 | $1.4 \times 10^{-9}$ | $3.2 \times 10^{-9}$ |
| 73 | Exendin-4(1-27)-Peg3-[Leu2]Gastrin4 | $4.1 \times 10^{-11}$ | $8.1 \times 10^{-9}$ |
| 74 | [Tyr13,Leu14]Exendin-4(1-27)-Peg3-Peg3-[Leu4]Gastrin6 | $5.0 \times 10^{-11}$ | $8.4 \times 10^{-9}$ |
| 75 | [Tyr13,Phe25]Exendin-4(1-27)-Peg3-Peg3-[Leu4]Gastrin6 | $3.5 \times 10^{-11}$ | $8.4 \times 10^{-9}$ |
| 76 | [Leu14,Phe25]Exendin-4(1-27)-Peg3-Peg3-[Leu4]Gastrin6 | $2.6 \times 10^{-11}$ | $7.9 \times 10^{-9}$ |
| 77 | [Tyr13,Leu14,Phe25]Exendin-4(1-27)-Peg3-Peg3-[Leu4]Gastrin6 | $4.4 \times 10^{-11}$ | $9.1 \times 10^{-9}$ |
| 78 | Side chain-cyclo([Lys12,Glu16]Exendin-4(1-28)-Peg3-Peg3-[Leu4]Gastrin6 | $2.5 \times 10^{-11}$ | $5.9 \times 10^{-9}$ |
| 79 | Side chain-cyclo([Glu16,Lys20]Exendin-4(1-28)-Peg3-Peg3-[Leu4]Gastrin6 | $2.6 \times 10^{-11}$ | $5.3 \times 10^{-9}$ |
| 80 | Side chain-cyclo([Lys20,Glu24]Exendin-4(1-28)-Peg3-Peg3-[Leu4]Gastrin6 | $3.2 \times 10^{-11}$ | $4.0 \times 10^{-9}$ |
| 81 | [Lys16]Exendin-4(1-28)-Peg3-Peg3-[Leu4]Gastrin6 | $3.2 \times 10^{-11}$ | $1.5 \times 10^{-8}$ |
| 82 | Exendin-4(1-28)-Peg3-K-Peg3-[Leu4]Gastrin6 | $2.8 \times 10^{-11}$ | $2.14 \times 10^{-8}$ |
| 83 | Exendin-4(1-28)-[Thr4]Gastrin6 | $4.4 \times 10^{-11}$ | $5.8 \times 10^{-8}$ |
| 84 | Exendin-4(1-28)-[Phe4]Gastrin6 | $4.4 \times 10^{-11}$ | $1.4 \times 10^{-7}$ |
| 85 | [Leu14]Exendin-4(1-28)-[1Nal3,Leu4]Gastrin6 | $4.0 \times 10^{-11}$ | $2.7 \times 10^{-7}$ |
| 86 | [Leu14]Exendin-4(1-28)-[Nle4]Gastrin6 | $5.2 \times 10^{-11}$ | $2.4 \times 10^{-8}$ |
| 87 | [Leu14]Exendin-4(1-28)-[Leu4,[3-(3-Pyridyl)-Ala]6]Gastrin6 | $2.8 \times 10^{-11}$ | $2.0 \times 10^{-8}$ |
| 88 | [Glu9,Leu14,Phe25,Tyr13]Exendin-4(1-27)-Peg3-Peg3-[Leu4]Gastrin6 | $4.6 \times 10^{-11}$ | $2.0 \times 10^{-8}$ |
| 89 | [Leu14,Phe25,Tyr13]Exendin-4(1-27)-Peg3-Peg3-[Leu4,Phe3]Gastrin6 | $2.3 \times 10^{-11}$ | $1.2 \times 10^{-6}$ |
| 90 | [Glu9,Leu14,Phe25,Tyr13]Exendin-4(1-27)-Peg3-Peg3-[Leu4,Phe3]Gastrin6 | $3.2 \times 10^{-11}$ | $1.3 \times 10^{-6}$ |
| 91 | [Arg27,Leu14,Phe25,Tyr13]Exendin-4(1-27)-Peg3-[Leu4]Gastrin6 | $6.8 \times 10^{-11}$ | $1.8 \times 10^{-8}$ |
| 92 | [Arg12,27,Leu14,Lys16,Phe25,Tyr13]Exendin-4(1-27)-Peg3-[Leu4]Gastrin6 | $1.7 \times 10^{-10}$ | $2.6 \times 10^{-8}$ |
| 93 | [Arg12,27,Leu14,Lys20,Phe25,Tyr13]Exendin-4(1-27)-Peg3-[Leu4]Gastrin6 | $5.8 \times 10^{-11}$ | $2.6 \times 10^{-8}$ |
| 94 | [Arg12,27,Leu14,Lys24,Phe25,Tyr13]Exendin-4(1-27)-Peg3-[Leu4]Gastrin6 | $1.3 \times 10^{-10}$ | $3.6 \times 10^{-8}$ |
| 95 | [Arg12,Leu14,Phe25,Tyr13]Exendin-4(1-27)-Peg3-[Leu4]Gastrin6 | $7.9 \times 10^{-11}$ | $1.4 \times 10^{-8}$ |
| 96 | [Glu9,Leu14,Phe25,Tyr13]Exendin-4(1-27)-[Leu2]Gastrin4 | $1.2 \times 10^{-9}$ | $2.11 \times 10^{-7}$ |
| 97 | [Glu9,Leu14,Phe25,Tyr13]Exendin-4(1-27)-Peg3-[Leu2]Gastrin4 | $6.0 \times 10^{-11}$ | $1.3 \times 10^{-8}$ |
| 98 | [Glu9,Leu14,Phe25,Tyr13]Exendin-4(1-27)-Orn-Peg3-[Leu2]Gastrin4 | $4.6 \times 10^{-11}$ | $1.0 \times 10^{-8}$ |
| 99 | [Glu9,Leu14,Phe25,Tyr13]Exendin-4(1-27)-Peg3-Orn-[Leu2]Gastrin4 | $4.1 \times 10^{-11}$ | $5.1 \times 10^{-8}$ |
| 100 | [Glu9,Leu14,Phe25,Tyr13]Exendin-4(1-27)-Orn-Orn-[Leu2]Gastrin4 | $1.1 \times 10^{-10}$ | $8.6 \times 10^{-7}$ |
| 101 | [Glu9,Leu14,Phe25,Tyr13]Exendin-4(1-27)-[Leu4]Gastrin6 | $1.1 \times 10^{-10}$ | $3.0 \times 10^{-8}$ |
| 102 | [Glu9,Leu14,Phe25,Tyr13]Exendin-4(1-27)-Peg3-[Leu4]Gastrin6 | $9.1 \times 10^{-11}$ | $5.4 \times 10^{-8}$ |
| 103 | [Glu9,Leu14,Phe25,Tyr13]Exendin-4(1-27)-Orn-Peg3-[Leu4]Gastrin6 | $1.2 \times 10^{-10}$ | $1.0 \times 10^{-7}$ |
| 104 | [Glu9,Leu14,Phe25,Tyr13]Exendin-4(1-27)-Peg3-Orn-[Leu4]Gastrin6 | $8.7 \times 10^{-11}$ | $8.8 \times 10^{-9}$ |
| 105 | [Glu9,Leu14,Phe25,Tyr13]Exendin-4(1-27)-Orn-Orn-[Leu4]Gastrin6 | $1.1 \times 10^{-10}$ | $1.6 \times 10^{-8}$ |

TABLE 3

In vitro efficacy (EC$_{50}$, mol/l) of GLP-1 compounds (peptide conjugates) of the invention in activation of hGLP-1 R, hCCK-B R and mCCK-B R. (Only included in the GLP-1 application)

| Cpd. No. | Peptide conjugate | hGLP-1 R EC50 | hCCK-B R EC50 | mCCK-B R EC50 |
|---|---|---|---|---|
| 37 | GLP-1(7-36)-[Gln1,Leu15]Gastrin17 | $3.0 \times 10^{-11}$ | $2.6 \times 10^{-8}$ | $7.3 \times 10^{-8}$ |
| 38 | GLP-1(7-36)-K-[Gln1,Leu15]Gastrin17 | $3.0 \times 10^{-11}$ | $7.7 \times 10^{-8}$ | $1.1 \times 10^{-7}$ |
| 39 | GLP-1(7-36)-AAA-[Gln1,Leu15]Gastrin17 | $3.4 \times 10^{-11}$ | $1.9 \times 10^{-8}$ | $5.4 \times 10^{-8}$ |
| 40 | GLP-1(7-36)-SKK-[Gln1,Leu15]Gastrin17 | $3.1 \times 10^{-11}$ | $1.6 \times 10^{-8}$ | $5.9 \times 10^{-8}$ |
| 41 | GLP-1(7-36)-Peg3-SKK-[Gln1,Leu15]Gastrin17 | $2.3 \times 10^{-11}$ | $8.8 \times 10^{-9}$ | $5.1 \times 10^{-8}$ |
| 42 | GLP-1(7-36)-Peg3-Peg3-[Gln1,Leu15]Gastrin17 | $2.8 \times 10^{-11}$ | $8.2 \times 10^{-9}$ | $5.8 \times 10^{-8}$ |
| 43 | GLP-1(7-36)-8Aoc-SKK-[Gln1,Leu15]Gastrin17 | $4.9 \times 10^{-11}$ | $5.2 \times 10^{-8}$ | $8.3 \times 10^{-8}$ |
| 44 | GLP-1(7-36)-DBF-SKK-[Gln1,Leu15]Gastrin17 | $5.3 \times 10^{-11}$ | $2.6 \times 10^{-8}$ | $8.7 \times 10^{-8}$ |
| 45 | GLP-1(7-36)-8Aoc-8Aoc-[Gln1,Leu15]Gastrin17 | $4.2 \times 10^{-11}$ | $1.3 \times 10^{-8}$ | $7.1 \times 10^{-8}$ |
| Control | GLP-1(7-36) | $1.7 \times 10^{-11}$ | N.T. | N.T. |
| Control | Exendin-4(1-39) | $2.4 \times 10^{-11}$ | N.T. | N.T. |
| Control | h[Gln1,Leu15]Gastrin17 | N.T | $4.7 \times 10^{-9}$ | $1.8 \times 10^{-8}$ |
| Control | CCK-8 | N.T | $6.3 \times 10^{-9}$ | $1.6 \times 10^{-7}$ |
| Control | h[Leu15]Gastrin17 | N.T | $2.4 \times 10^{-9}$ | N.T |
| 106 | [Lys(Hexadecanoyl-isoGlu)34]GLP-1(7-37)-Peg3-Peg3-[Leu4]Gastrin6 | $4.9 \times 10^{-11}$ | $1.8 \times 10^{-8}$ | |
| 107 | [Arg34,Lys(Hexadecanoyl-isoGlu)26]GLP-1(7-37)-Peg3-Peg3-[Leu4]Gastrin6 | $1.4 \times 10^{-10}$ | $2.9 \times 10^{-8}$ | |
| 108 | [Arg26,34,Lys(Hexadecanoyl-isoGlu)36]GLP-1(7-37)-Peg3-Peg3-[Leu4]Gastrin6 | $1.1 \times 10^{-10}$ | $7.8 \times 10^{-8}$ | |
| 109 | [Lys(Hexadecanoyl-isoGlu)26]GLP-1(7-37)-Peg3-Peg3-[Leu4]Gastrin6 | $9.9 \times 10^{-11}$ | $2.6 \times 10^{-8}$ | |
| 110 | [Arg26,34,Gly8,Lys(Hexadecanoyl-isoGlu)36]GLP-1(7-37)-Peg3-Peg3-[Leu4]Gastrin6 | $1.2 \times 10^{-10}$ | $2.9 \times 10^{-8}$ | |
| 111 | [Aib8,Arg34,Lys(Hexadecanoyl-isoGlu)26]GLP-1(7-37)-Peg3-Peg3-[Leu4]Gastrin6 | $8.8 \times 10^{-11}$ | $5.9 \times 10^{-8}$ | |
| 112 | [Aib8,Arg34]GLP-1(7-37)-Peg3-Peg3-[Leu4]Gastrin6 | $4.3 \times 10^{-11}$ | $4.2 \times 10^{-8}$ | |
| 113 | [Arg34]GLP-1(7-37)-Peg3-Peg3-[Leu4]Gastrin6 | $2.7 \times 10^{-11}$ | $2.4 \times 10^{-8}$ | |

NT: Not tested

Results

The results summarized in Tables 1, 1a, 2 and 3 above indicate that generally all of the peptide conjugates of the invention are potent agonists of all of the three receptors in question, and that they exhibit closely similar levels of efficacy.

Example 3

Screening of Compound 73 on 92 Selected Peptide GPCRs

Compound 73 was selected for testing on a large selection of peptide receptors of the GPCR type, in order to discover any receptor promiscuity early on. The receptors are of the class A and B GPCR families and the assay was carried out at Millipore using their GPCR screening platform. Each GPCR was activated by its control peptide ligand (known activator of the respective receptors) or by Compound 73 at 100 nM concentration. Agonism on a receptor is given as % of the control peptide (that gives 100% activation by definition). Only the expected GLP-1 receptor and the CCKB (CCK2) receptor was activated significantly (100 and 95%, respectively) by Compound 73 showing that the peptide is specific for these two receptors.

Example 4

Pharmacokinetic (PK) of Compound 1 and 33 in Mice

Method

Three C57BI mice were given 100 nmol of compound 1 or 33 per kg as i.v. or s.c. bolus, and plasma samples were collected up to 240 min post-dose. Samples were collected from three mice at each time point. The plasma samples were analyzed for the presence of compound 33 using LC/MS/MS (10-1000 nM).

Results

TABLE 4

PK parameters after i.v. and s.c. administration of 100 nmol/kg to mice

| Parameter | Unit | Compound 33 | | Compound 1 | |
|---|---|---|---|---|---|
| | | s.c. | i.v. | s.c. | i.v. |
| $t_{1/2\lambda}$ | hr | 3.4 | 2.8 | 0.45 | 0.28 |
| F | % | 100% | — | 97% | — |

Figure 1B:
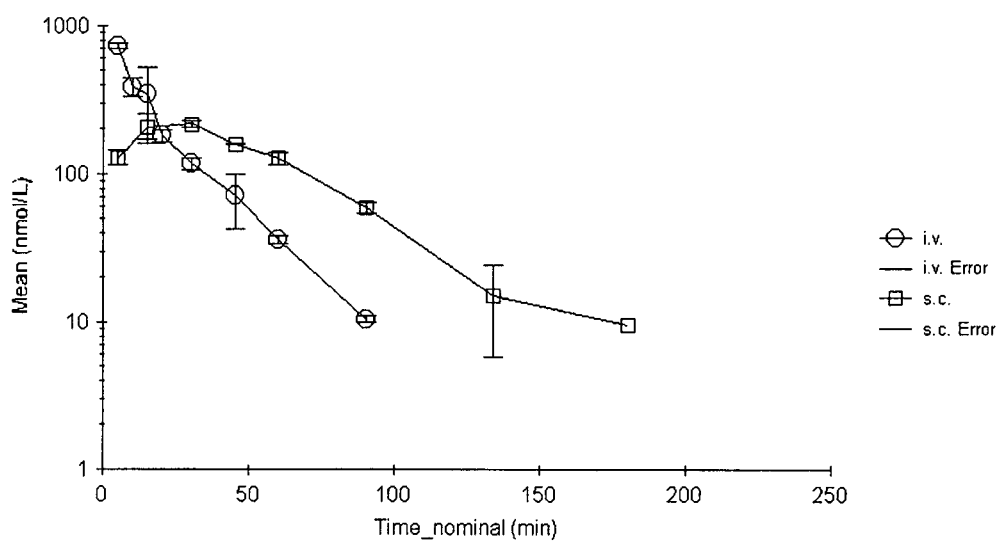

Both compounds exhibited an excellent bioavailability (F) after sc administration, with compound 33 showing a superior PK profile likely due to a longer half-life (FIG. 1A, 1B and Table 4).

Example 5

PK of Compound 33 and 74-80

Method

Two C57BI mice were given a single subcutaneous dose of 100 nmol/kg of each peptide. Blood samples were taken after 5 and 30 min and after 1, 2, 4, 6, 16 and 24 hour. At each time point, samples from two mice were taken. Plasma samples were analyzed after solid phase extraction (SPE) by liquid chromatography mass spectrometry (LC-MS/MS).

TABLE 5

T½ after s.c. administration of 100 nmol/kg to mice

| Compound | $t_{1/2}$ (h) |
|---|---|
| 33 | 2.0 |
| 74 | 3.6 |
| 76 | 2.3 |
| 77 | 3.1 |
| 75 | 2.5 |
| 78 | 2.0 |
| 79 | 1.5 |
| 80 | 1.9 |

Figure 2:
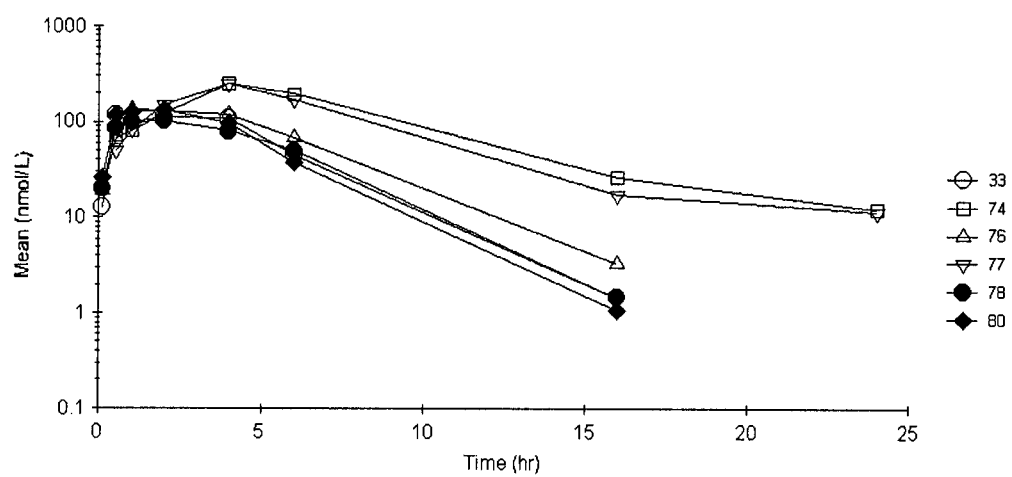
FIG. 2. Mean plasma concentration versus time (log-linear) after s.c. administration of 100 nmol compound/kg of Compound 33, 74, 76, 77, 78 and 80 to mice. n=2/datapoint.

The peptides show promising T½ profiles, with compound 74 and 77 being superior to the rest with respect to half-life and exposure (Table 5 and FIG. 2).

Example 6

In Vivo Activity of Peptide Conjugates of the Invention in Db/Db Mice

Materials and Methods

The db/db mouse model has previously been used to assess the β-cell preserving effects of potential therapeutic candidates [Rolin, B. et al., *Am. J. Physiol. Endocrinol. Metab.* 283: E745-E752 (2002)]. Several studies have demonstrated a correlation between pancreatic Insulin content and β-cell mass [Rolin, B. et al. (loc.cit.); Suarez-Pinzon, W. L. et al., *Diabetes* 54: 2596-2601 (2005); Suarez-Pinzon W. L. et al., *Diabetes* 57: 3281-3288 (2008)].

In the present study, 6 week old db/db (BKS.Cg-m+/+Lepr$^{db}$/J) female mice (Taconic Europe A/S, Lille Skensved, Denmark) were acclimatized to their new environment and given ad libitum access to normal chow and water. Mice were housed in pairs in a light-, temperature- and humidity-controlled room. The progression of diabetes was followed for 2 weeks by monitoring blood glucose levels, and then before treatment the diabetic mice were randomized according to their blood glucose levels into treatment groups (n=10/group). Animals were then mock-injected subcutaneously (sc) with 100 μl vehicle (once daily) for a period of three days to acclimatize the animals to handling and injections. Following randomization and mock injection, animals were then treated (sc, twice daily) for 16 days with combinations of h[Leu15]Gastrin17 (1, 10 and 50 nmol/kg) and Exendin-4(1-39) (1, 10 and 50 nmol/kg), or with Compound 1 (peptide conjugate of the invention) [i.e. Exendin-4(1-39)-Peg3-Peg3-[Gln1,Leu15]Gastrin17] (1, 10 and 50 nmol/kg), or with vehicle (PBS buffer; injection volume 5 ml/kg). Daily injections took place between 8:00 and 9:00 hours, and between 15:00 and 16:00 hours, with fresh solutions prepared immediately before dosing.

Blood samples (200 μl) were obtained from the orbital plexus and placed in EDTA coated tubes before dosing (day 1), and at day 8 and day 16 of the treatment. Each blood sample was centrifuged, and plasma (100 μl) was stored at −80° C. for later analysis. Blood samples for blood glucose determinations were taken from the tail vein. Following the last day of dosing, all animals were sacrificed (day 16) by $CO_2$ anesthesia, followed by cervical dislocation. The pancreas from each animal was immediately isolated, weighed, and stored for later analysis of Insulin content.

Measurements

Whole blood glucose concentration (mM) was determined by the immobilized glucose oxidase method (Elite Autoanalyser, Bayer, Denmark). Plasma C-peptide was determined using a rat C-peptide radioimmunoassay kit (Linco/Millipore, kit RCP-21K). Pancreatic Insulin content was determined using a rat Insulin radioimmunoassay kit (Linco/Millipore, kit R1-13).

Results

Figure 3:
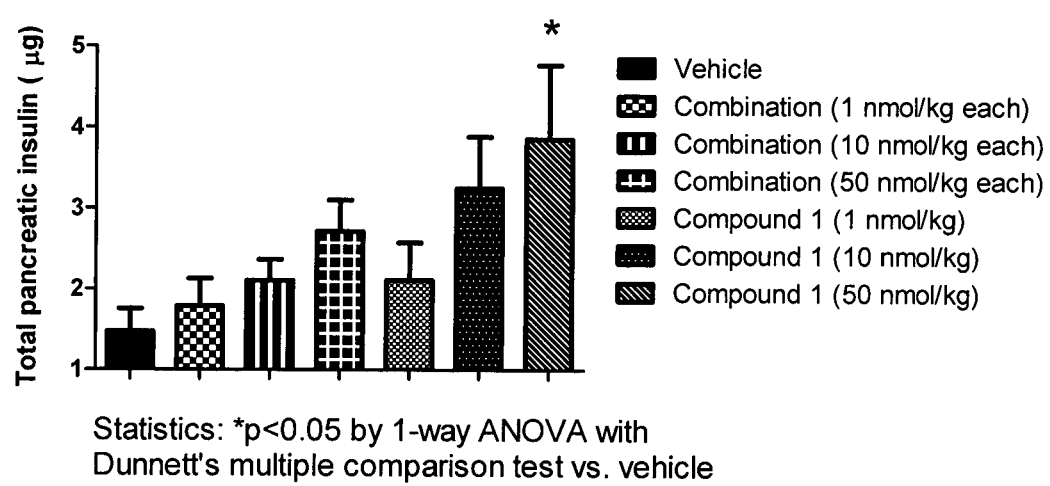
FIG. 3 presents data for total pancreatic insulin content (in μg) in db/db diabetic mice following administration of (i) three concentrations (1, 10 and 50 nmol/kg) of Compound 1 of the invention [Exendin-4(1-39)-Peg3-Peg3-[Gln1,Leu15] Gastrin17; vide infra], (ii) three corresponding concentrations of a 1:1 additive combination of the Exendin-4(1-39) and h[Leu15]Gastrin17 peptides (1, 10 and 50 nmol/kg of each peptide) and (iii) vehicle.

As is clearly apparent from FIG. 3, a markedly higher content of pancreatic Insulin was seen in animals treated with the peptide conjugate of the invention (Compound 1) compared to that in animals treated with a simple combination of Exendin-4(1-39) and h[Leu15]Gastrin17 or treated with vehicle.

It thus appears that the effect on pancreatic Insulin levels arising as a result of the covalent coupling or linkage (conjugation) of the Exendin-4 moiety and the Gastrin moiety in the peptide conjugate of the invention may be unexpectedly greater than that achieved when employing a corresponding, additive combination of the two, individual peptide components.

Example 7

Six Week Study

Protocol 125 db/db (BKS.Cg-m+/+Lepr$^{db}$/J) female mice (6 weeks at arrival) were obtained from Taconic Europe A/S.

At day −4 blood was collected from semi-fasted animals for determination of baseline plasma C-peptide, plasma insulin, blood glucose, and HbA1c levels. Animals were then stratified into 5 treatment groups of n=20 based on baseline plasma C-peptide and HbA1c levels. Animals were injected s.c. with 100 μl of vehicle twice daily for at least 3 days to acclimatize the animals to handling and experimental procedures.

Then animals were injected s.c. twice daily with peptides or vehicle for a total of 42 days according to Table 6. The daily injections took place between 08:00-09:00 h and 15:00-16:00 h with freshly prepared solutions. The last day of dosing was day 42 in the morning.

TABLE 6

Groups and doses

| Groups | Substance | Route | Dose (nmol/kg/day) |
|---|---|---|---|
| Group 1 | Vehicle (PBS) | SC twice daily | — |
| Group 2 | Exendin-4 | | 2 × 25 |
| Group 3 | Exendin-4 + Gastrin17 | | 2 × 25 + 2 × 25 |
| Group 4 | Compound 33 | | 2 × 25 |

The study was terminated on day 42. Animals were semi-fasted, and they received the final dose in the morning. Blood was sampled for determination of plasma C-peptide, plasma insulin, blood glucose, and HbA1c. After the blood sampling, animals were euthanized using $CO_2$ followed by cervical dislocation. The pancreas was isolated, weighed, divided into 3 pieces, and transferred to tubes containing 2 ml of cold acidic alcohol and analyzed for insulin content.

Figure 4:
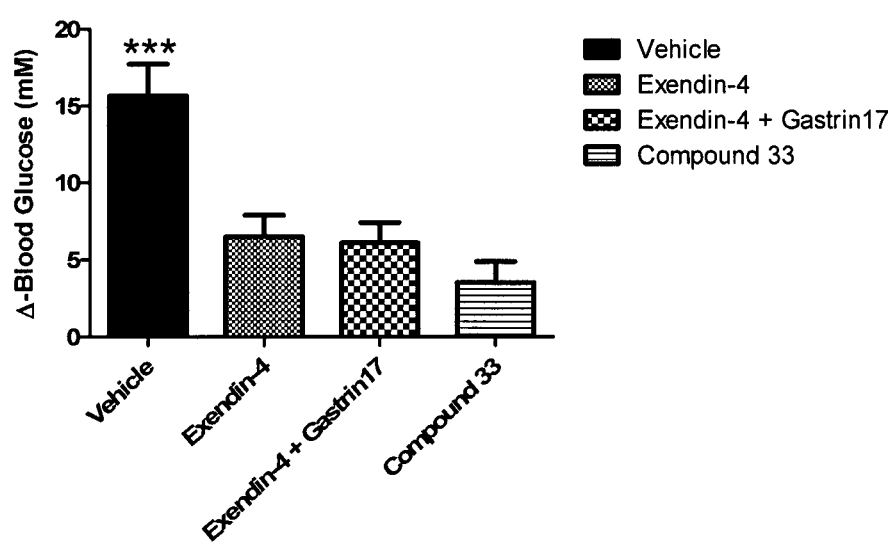
FIG. 4. Δ-Blood glucose in mice. Data were analyzed using Kruskal-Wallis test followed by Dunn's multiple comparison test,***p<0.001. Comparison of Compound 33, Exendin-4a combination of Exendin-4(1-39) and h[Leu15]Gastrin17 and Vehicle respectively; n=16-19 per group.
Figure 5:
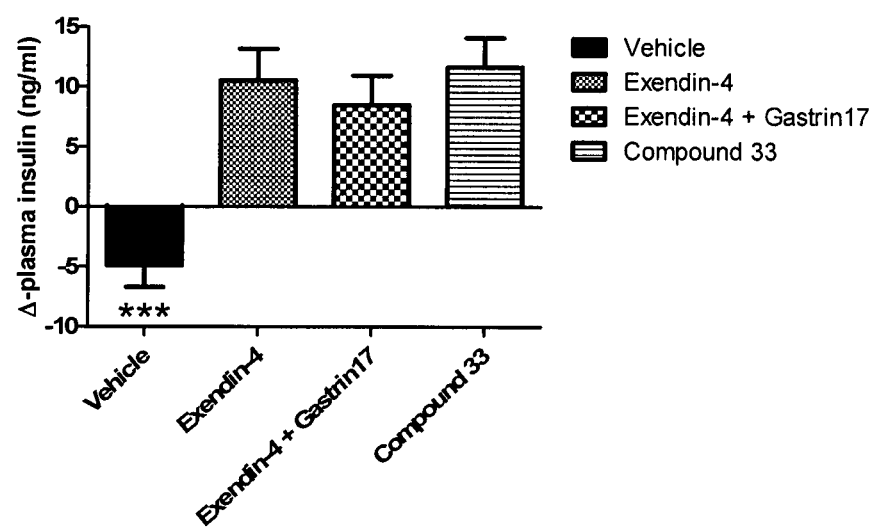
FIG. 5. Δ-Plasma insulin in mice. Data were analyzed using Kruskal-Wallis test followed by Dunn's multiple comparison test, ***p<0.001. Comparison of Compound 33, Exendin-4, a combination of Exendin-4(1-39) and h[Leu15] Gastrin17 and Vehicle respectively; n=16-19 per group.
Figure 6:
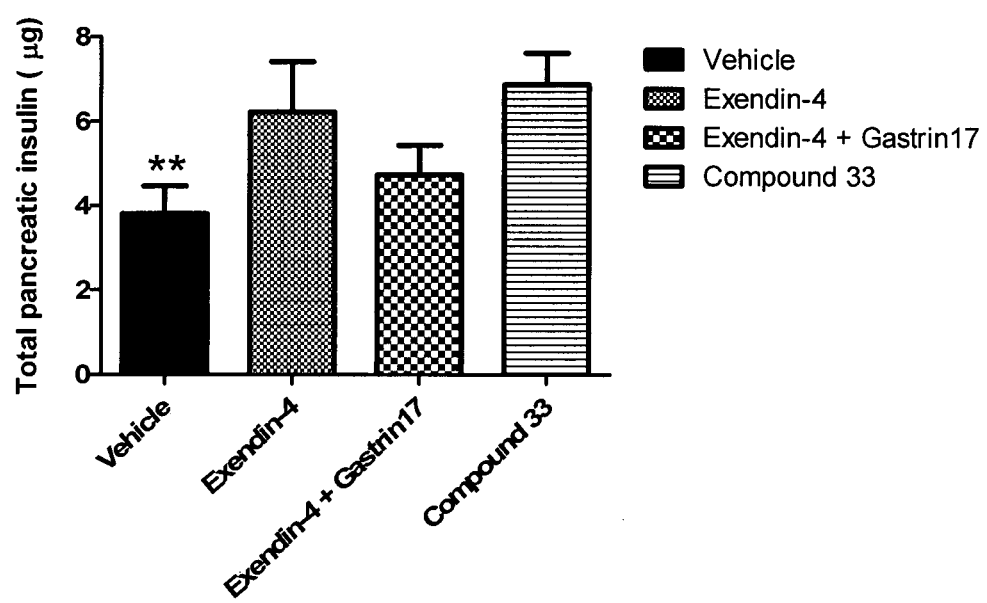
FIG. 6. Pancreatic insulin content in mice. Data were analyzed using Kruskal-Wallis test followed by Dunn's multiple comparison test, **p<0.01. Comparison of Compound 33, Exendin-4, a combination of Exendin-4(1-39) and h[Leu15] Gastrin17 and Vehicle respectively; n=16-19 per group.

Compound 33 lowered blood glucose levels (FIG. 4) and elevated plasma insulin concentrations relative to vehicle in the db/db mice (FIG. 5). In addition, treatment with Compound 33 caused a statistically significant reduction in HbA1c levels compared to vehicle-treated and Gastrin17+Exendin-4 treated animals (FIG. 6). These results suggest that Compound 33 improved glycemic control in the diabetic mice.

Figure 7:
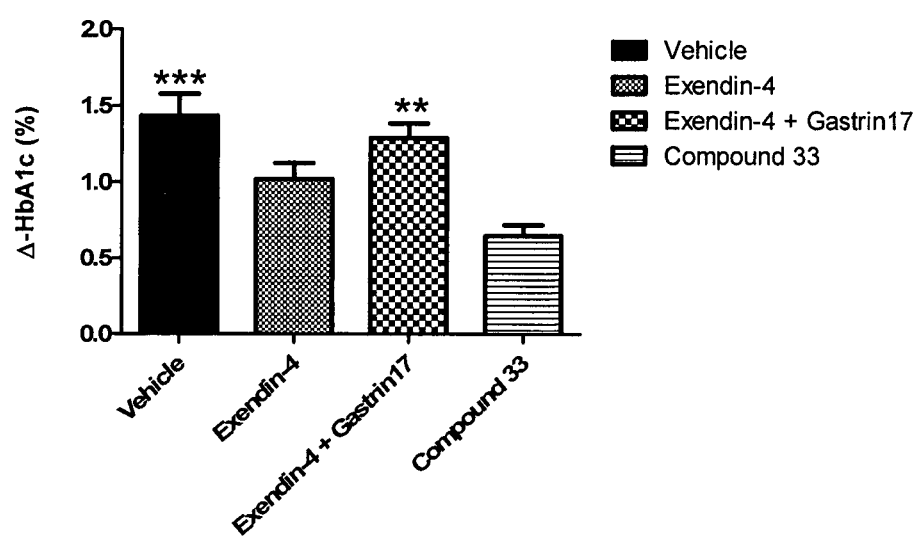
FIG. 7. Δ-HbA1c in mice. Data were analyzed using Kruskal-Wallis test followed by Dunn's multiple comparison test, **p<0.01, mp<0.001. Comparison of Compound 33, Exendin-4, a combination of Exendin-4(1-39) and h[Leu15] Gastrin17 and Vehicle respectively; n=16-19 per group.
Figure 8:
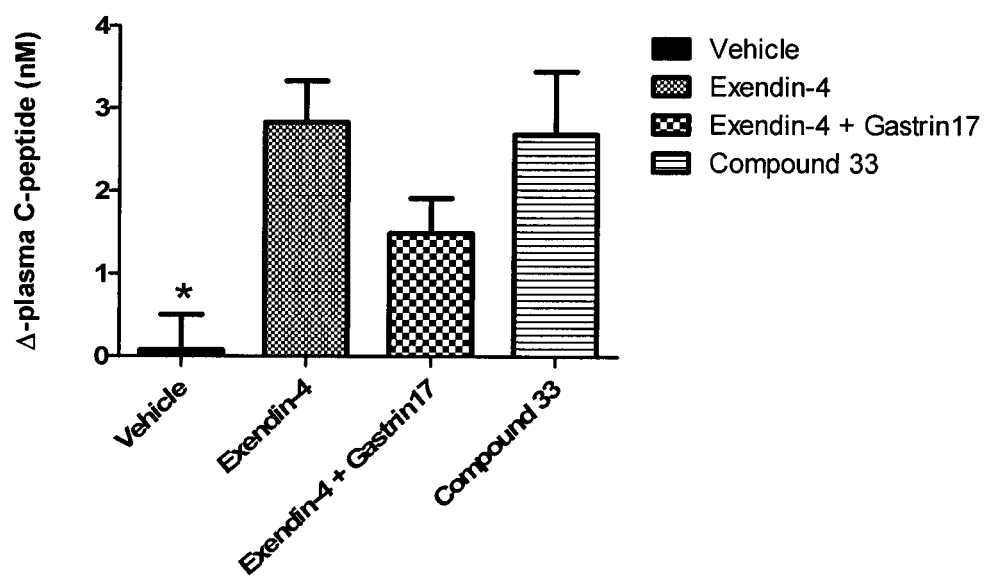
FIG. 8. Δ-plasma C peptide in mice. Data were analyzed using Kruskal-Wallis test followed by Dunn's multiple comparison test, *p<0.05. Comparison of Compound 33, Exendin-4, a combination of Exendin-4(1-39) and h[Leu15]Gastrin17 and Vehicle respectively; n=16-19 per group.

Also, Compound 33 caused a statistically significant increase in pancreatic insulin content relative to vehicle (FIG. 7). In addition both Compound 33 and Exendin-4 caused a significant increase in the delta C-peptide level in plasma, indicating an improved pancreatic function in all groups (FIG. 8).

Co-administration of Exendin-4 and Gastrin was not superior to Exendin-4 in improving glycemic control in the db/db mice. Thus, in the doses used in this study there was no synergistic effect of Exendin-4 and Gastrin on glycemia.

Our data show that the peptide conjugate Compound 33 increases the pancreatic insulin content and improves glycemic control in the db/db mice significantly as evident by the decrease in HbA1c.

Example 8

Drug Holiday Study

Protocol 150 male db/db mice were obtained at an age of 5-6 weeks. The animals were housed (5 mice/cage) under controlled conditions (20-22° C., 55-85% humidity) following a 12:12-hrs light/dark cycle with light on at 05.00 AM. The animals were fed ad libitum with standard Altromin No. 1324 diet and had free access to acidified tap water. At the time of study start the animals were 8-9 weeks old. All animals were acclimatized and handled daily minimum one week prior to the experiment.

Blood Samples:

Before treatment start, and on day 93 (before termination) in fasted mice (17 hrs) a blood sample (150 µl) was obtained from orbital plexus with an EDTA coated micro-pipette. Blood samples were taken into EDTA coated tubes and kept on ice. The blood sample was centrifuged and the resulting plasma (at least 50 µl) was stored (at −80° C.) for later analysis of C-peptide and insulin level. Also, on day −10/12 (before treatment start), and day 93 (before termination) a blood sample (50 µl) obtained from orbital plexus was analyzed for BG (sticks) and HbA1c.

Stratification

On days −6 to −4 before the first drug dose, fasted animals (17 hrs) were subjected to an oral glucose tolerance test (OGTT, see below). The area under the blood glucose concentration curve obtained over a 240-minute period ($AUC_{0-240}$; unit: mM*min) was used to stratify animals into 5 groups (A-E) of 26 animals each in order to obtain similar glucose tolerances in both groups. After the first 50 days of dosing (period 1) a second OGTT were performed. On the basis of this second OGTT test, each group of mice was stratified by AUC (as above) into two sub-groups displaying similar glucose tolerances.

Dosing:

The animals were given one daily (QD) subcutaneous (SC) dose of vehicle (2*n=26), Exendin-4 (n=26) or Compound33 (n=26) and dosed according to Table 6 for a period of 50 days. Dosing was performed between 02.00 and 03.00 PM every day, with an injection volume of 5 ml/kg. After 50 days of dosing the animals were stratified into 7 groups as illustrated in Table 1. This dosing regimen was continued for 40 days until animals were sacrificed on day 93.

Oral Glucose Tolerance Test (OGTT):

OGTT was performed on days −6/4, 50, 65, 78 and 91 of the treatment period on animals fasted overnight (17 hours) after the last injection of vehicle or compound. Blood samples were taken from the tip of the tail and blood glucose measured. To prevent confounding food intake, the animals were kept fasted during all OGTTs. Immediately after the initial blood sample (t=0, fasting blood glucose level) an oral dose (1 g/kg) of glucose (Glucose-monohydrat, SAD 500 g/l), dissolved MQ water was given (5 ml/kg, 0.2 g/ml), and the animals were returned to their home cages (t=0). Then, BG levels were measured at t=15, 30, 60, 120, and 240 minutes.

Fasting Blood Glucose:

To further monitor the diabetic status of the animals, fasting blood glucose levels were measured after 8 hours of fasting on day 0, 37, 44, 58, 72, and 85. To minimize stress, animals were fasted during the day (from 06.00 AM when habitual consumption of food was low), and fasting blood glucose was determined at 02.00 PM.

TABLE 6

Study groups

| Substance Period 1 | Substance Period 2 | Route | Dose (nmol/kg/day) |
|---|---|---|---|
| Vehicle | Vehicle | SC once daily | 0 + 0 |
| Vehicle | Exendin-4 | | 0 + 100 |
| Vehicle | Compound 33 | | 0 + 100 |
| Vehicle | Liraglutide | | 0 + 100 |
| Exendin-4 | Exendin-4 | | 100 + 100 |
| Exendin-4 | Vehicle | | 100 + 0 |
| Liraglutide | Liraglutide | | 100 + 100 |
| Liraglutide | Vehicle | | 100 + 0 |
| Compound 33 | Compound 33 | | 100 + 100 |
| Compound 33 | Vehicle | | 100 + 0 |

Vehicle: PBS: Phosphate buffered saline Gibco (#70011, pH = 7.4).

Figure 9:
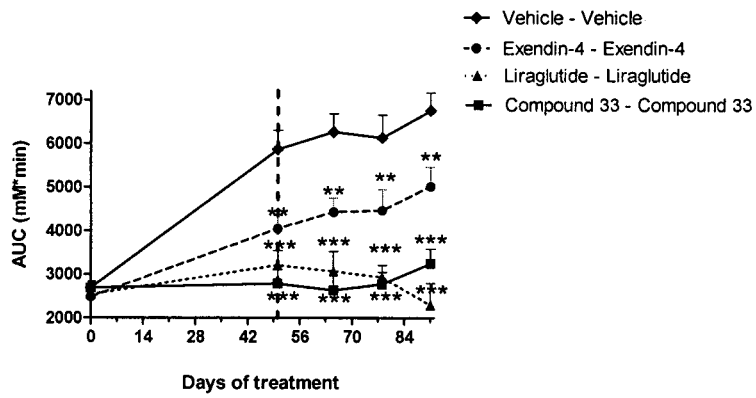
FIG. 9. Effect of SC administration of Exendin-4, Liraglutide or Compound 33 on glucose tolerance as measured by the Area Under the Curve (AUC) following a glucose load in db/db mice. Three treatment regimens were applied (A) Prevention, (B) Treatment, or (C) Holiday. Data are given as mean with SEM (n=8-13/group). Statistic: Data was compared by 2-way ANOVA followed by Bonferroni's post-test: *p<0.05; p<0.01; *p<0.001 vs. vehicle.
Figure 9:
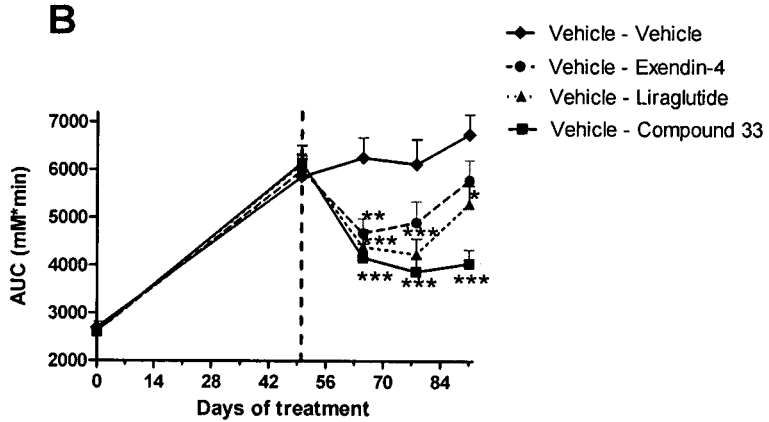
Figure 9:
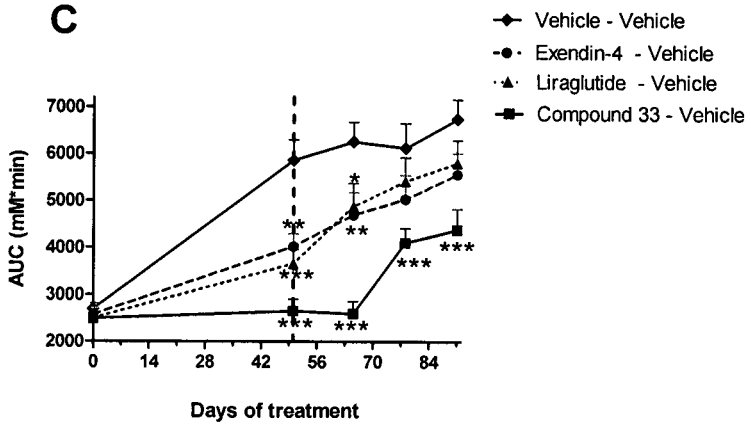
Figure 10:
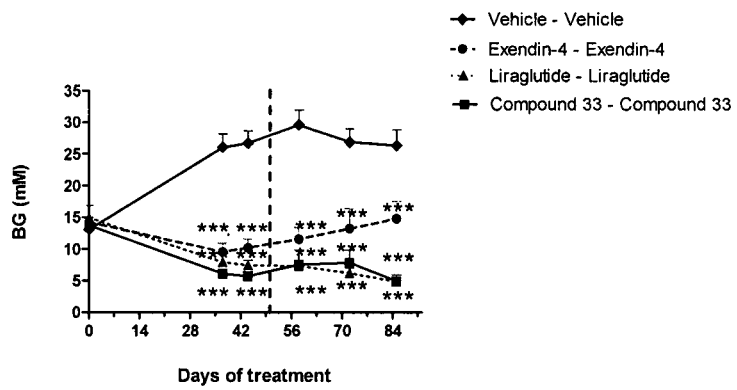
FIG. 10. Effect of SC administration of Exendin-4, Liraglutide or Compound 33 on 8 h fasting blood glucose in db/db mice. Three treatment regimens were applied (A) Prevention, (B) Treatment or (C) Holiday. Data are given as mean with SEM (n=8-13/group). Statistic: Data was compared by 2-way ANOVA followed by Bonferroni's post-test: *p<0.05; p<0.01; *p<0.001 vs. vehicle.
Figure 10:
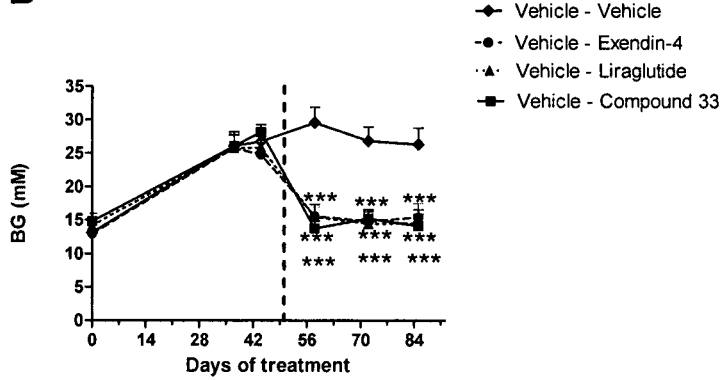
Figure 10:
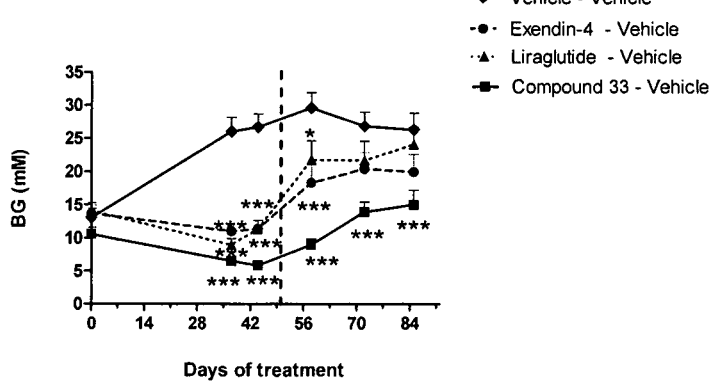
Figure 11:
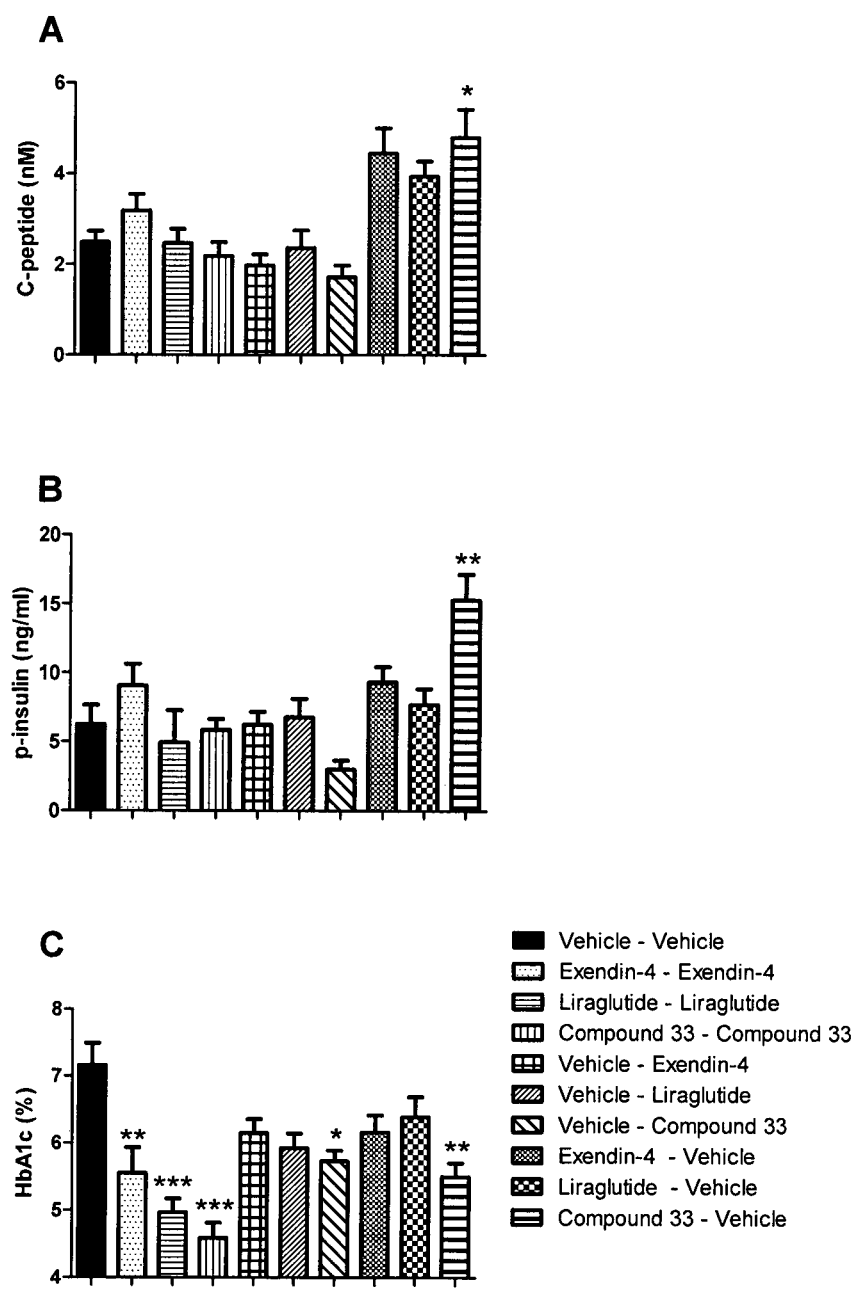
FIG. 11. Effect of SC administration of Exendin-4, Liraglutide or Compound 33 on terminal (day −93) values of (A) plasma C-peptide, (B) plasma insulin, or (C) HbA1c (%). Data are given as mean with SEM (n=8-13/group). Statistic: Data was compared by 1-way ANOVA Kruskal-Wallis test followed by Dunn's MC test: mp<0.001, **p<0.01, *p<0.05 vs. vehicle.

The GLP-1-Gastrin dual agonist Compound 33 lowered the area under the glucose curve (AUC) following an oral glucose challenge test and also the fasting blood glucose was decreased compared to vehicle control regardless if the treatment paradigm was prevention, treatment or holiday (FIGS. 9+10). Also, plasma levels of insulin and C-peptide and blood levels of HbA1c were significantly lower in mice treated with Compound 33 compared to those treated with vehicle control (FIG. 11). These data shows that Compound 33 improves glycemic control in diabetic db/db mice, and to a greater extent than does both Exendin-4 and Liraglutide. Notably, the effect of the compounds on glycemic control was sustained for several days after treatment was stopped, most pronounced in the mice treated with Compound 33.

The invention claimed is:

1. A peptide conjugate or pharmaceutically acceptable salt thereof having the formula $$R^1-Z_a-L_a-Y_a-R^2 \quad (I)$$

wherein $R^1$ is H, $C_{1-4}$ alkyl, acetyl, formyl, benzoyl or trifluoroacetyl;

$R^2$ is OH or $NH_2$;

$Z_a$ is a peptide sequence having the formula IVa

His-Gly-Glu-Gly-Thr-Phe-Thr-Ser-Z9-Leu-Ser-Z12-Gln-Met-Glu-Z16-Glu-Ala-Val-Arg-Leu-Phe-Ile-Glu-Trp-Leu-Z27-Z28 (IVa)

wherein

Z9 is selected from Glu and Asp;
Z12 is selected from Lys and Orn;
Z16 is selected from Glu and Lys;
Z27 is selected from Lys and Orn;
Z28 is selected from Asn and Asp or is absent;

$L_a$ is a sequence having the formula IVb

L1-L2-L3-L4 (IVb)

wherein

L1 is selected from Peg3, Gln, Cys, Lys and Orn or is absent;
L2 is selected from Peg3, Gln, Cys, Lys and Orn or is absent;
L3 is selected from Peg3, Gln, Cys, Lys and Orn or is absent;
L4 is selected from Peg3, Gln, Cys, Lys and Orn or is absent;

$Y_a$ is a peptide sequence having the formula IVc

Y12-Y13-Trp-Leu-Asp-Phe (IVc)

wherein

Y12 is Tyr or is absent; and
Y13 is Gly or is absent.

2. The peptide conjugate or pharmaceutically acceptable salt thereof according to claim 1, wherein Z12 is Lys and Z16 is Glu, and wherein said residues form an intramolecular bridge.

3. The peptide conjugate or pharmaceutically acceptable salt thereof according to claim 2, wherein the intramolecular bridge is a lactam ring.

4. The peptide conjugate or pharmaceutically acceptable salt thereof according to claim 1, wherein $Z_a$ has at least 85% identity to native exendin-4, e.g. at least 90 or 95%.

5. The peptide conjugate or pharmaceutically acceptable salt thereof according to claim 1, wherein the peptide of formula I is selected from the group consisting of:

Exendin-4(1-28)-[Leu4]Gastrin6,
Exendin-4(1-28)-K-[Leu4]Gastrin6, and
Exendin-4(1-28)-Peg3-Peg3-[Leu4]Gastrin6.

6. The peptide conjugate or pharmaceutically acceptable salt thereof according to claim 5, wherein the peptide of formula I is selected from the group consisting of:

Exendin-4(1-28)-Peg3-Peg3-[Leu3]Gastrin5,
Exendin-4(1-27)-Peg3-Peg3-[Leu4]Gastrin6,
Exendin-4(1-28)-Peg3-Peg3-[Leu2]Gastrin4,
[Orn12]Exendin-4(1-28)-Peg3-Peg3-[Leu4]Gastrin6,
[Orn27]Exendin-4(1-28)-Peg3-Peg3-[Leu4]Gastrin6,
[Asp28]Exendin-4(1-28)-Peg3-Peg3-[Leu4]Gastrin6,
Exendin-4(1-28)-Peg3-[Leu4]Gastrin6,
Exendin-4(1-28)-[Leu4]Gastrin6,
Exendin-4(1-27)-Peg3-[Leu4]Gastrin6,
Exendin-4(1-27)-Peg3-[Leu3]Gastrin5,
Exendin-4(1-27)-Peg3-[Leu2]Gastrin4,
[Lys16]Exendin-4(1-28)-Peg3-Peg3-[Leu4]Gastrin6, and
Exendin-4(1-28)-Peg3-K-Peg3-[Leu4]Gastrin6.

7. A method of treating a disease or disorder selected from the group consisting of: type 1 diabetes, type 2 diabetes, pre-diabetes, Insulin resistance syndrome, impaired glucose tolerance (IGT), disease states associated with elevated blood glucose levels, hyperglycemia, hypertension, atherogenic dyslipidemia, arteriosclerosis (e.g. atherosclerosis), coronary heart disease, peripheral artery disease, stroke, microvascular disease, gastric disease, metabolic syndrome, cancer (e.g. colon cancer), inflammatory bowel disease (IBD) and irritable bowel syndrome (IBS), in a subject in need thereof, the method comprising administering to said subject a therapeutically effective amount of a peptide conjugate or pharmaceutically acceptable salt thereof according to claim 1.

8. A method according to claim 7, wherein said subject is a human.

9. A pharmaceutical composition comprising a peptide conjugate, or pharmaceutically acceptable salt thereof, according to claim 1, together with a pharmaceutically acceptable carrier, excipient or vehicle.

10. A method for promoting weight loss in an individual in need thereof, said method comprising administering to said individual a therapeutically effective amount of a peptide conjugate or pharmaceutically acceptable salt thereof according to claim 1.

11. A method of improving circulating glucose levels, glucose tolerance and/or circulating cholesterol levels, lowering circulating LDL levels, and/or increasing HDL/LDL ratio in an individual in need thereof, said method comprising administering to said individual a therapeutically effective amount of a peptide conjugate or pharmaceutically acceptable salt thereof according to claim 1.

12. The method according to claim 7, wherein the compound is administered as part of a combination therapy with an agent for treatment of a condition selected from the group consisting of: diabetes, obesity, dyslipidaemia, or hypertension.

13. The method according to claim 12 wherein the agent for treatment of diabetes is selected from the group consisting of: metformin, a sulfonylurea, a glinide, a DPP-IV inhibitor, a glitazone, insulin and an insulin analogue.

14. The method according to claim 12 wherein the agent for treatment of obesity is selected from the group consisting of a glucagon-like peptide receptor 1 agonist, peptide YY or analogue thereof, cannabinoid receptor 1 antagonist, lipase inhibitor, melanocortin receptor 4 agonist, and melanin concentrating hormone receptor 1 antagonist.

15. The method according to claim 12 wherein the agent for treatment of hypertension is selected from the group consisting of an angiotensin-converting enzyme inhibitor, angiotensin II receptor blocker, diuretic, beta-blocker, and calcium channel blocker.

16. The method according to claim 12 wherein the agent for treatment of dyslipidaemia is selected from the group consisting of a statin, a fibrate, a niacin and a cholesterol absorption inhibitor.

17. The method of improving circulating glucose levels, glucose tolerance and/or circulating cholesterol levels, lowering circulating LDL levels, and/or increasing HDL/LDL ratio in an individual in need thereof, said method comprising administering to said individual a therapeutically effective amount of a peptide conjugate or pharmaceutically acceptable salt thereof according to claim 1, wherein a drug holiday dosage regimen is used.

18. A process for manufacturing a compound according to claim 1, wherein said manufacture is by peptide synthesis or recombinant synthesis.

19. A device comprising at least one peptide conjugate, or pharmaceutically acceptable salt thereof, according to claim 1, for delivery of the peptide conjugate to a subject.

20. A kit comprising at least one peptide conjugate, or pharmaceutically acceptable salt thereof, according to claim 1, and further comprising packaging or instructions for use.

21. The method of claim 10, wherein the compound is administered as part of a combination therapy with an agent for treatment of a condition selected from the group consisting of diabetes, obesity, dyslipidaemia, and hypertension.

22. The method of claim 21, wherein the agent for treatment of diabetes is selected from the group consisting of metformin, a sulfonylurea, a glinide, a DPP-IV inhibitor, a glitazone, insulin, and an insulin analogue.

23. The method of claim 21, wherein the agent for treatment of obesity is selected from the group consisting of a glucagon-like peptide receptor 1 agonist, peptide YY and analogues thereof, cannabinoid receptor 1 antagonist, lipase inhibitor, melanocortin receptor 4 agonist, and melanin concentrating hormone receptor 1 antagonist.

24. The method of claim 21, wherein the agent for treatment of hypertension is selected from the group consisting of an angiotensin-converting enzyme inhibitor, angiotensin II receptor blocker, diuretic, beta-blocker, and calcium channel blocker.

25. The method of claim 11, wherein the compound is administered as part of a combination therapy with an agent for treatment of a condition selected from the group consisting of diabetes, obesity, dyslipidaemia, and hypertension.

26. The method of claim 25, wherein the agent for treatment of diabetes is selected from the group consisting of metformin, a sulfonylurea, a glinide, a DPP-IV inhibitor, a glitazone, insulin, and an insulin analogue.

27. The method of claim 25, wherein the agent for treatment of obesity is selected from the group consisting of a glucagon-like peptide receptor 1 agonist, peptide YY and analogues thereof, cannabinoid receptor 1 antagonist, lipase inhibitor, melanocortin receptor 4 agonist, and melanin concentrating hormone receptor 1 antagonist.

28. The method of claim 25, wherein the agent for treatment of hypertension is selected from the group consisting of an angiotensin-converting enzyme inhibitor, angiotensin II receptor blocker, diuretic, beta-blocker, and calcium channel blocker.

29. The method of claim 25, wherein the agent for treatment of dyslipidaemia is selected from the group consisting of a statin, a fibrate, a niacin, and a cholesterol absorption inhibitor.

30. The process according to claim 19, wherein said manufacture is by peptide synthesis.

31. The process according to claim 18, wherein said manufacture is by recombinant synthesis.

\* \* \* \* \*